United States Patent
Rolfe et al.

(10) Patent No.: US 7,208,222 B2
(45) Date of Patent: Apr. 24, 2007

(54) ASSEMBLED NON-RANDOM FOAMS

(75) Inventors: Jonathan L. Rolfe, North Easton, MA (US); Mark P. Amrich, Tynsborough, MA (US); Joseph A. Buturlia, Boxford, MA (US); Robert Cairns, Chester, NH (US); Robert Lynch, Newburyport, MA (US); Michael Gerry, Woburn, MA (US)

(73) Assignee: Viasys Healthcare Inc., Wilmington, MA (US)

( * ) Notice: Subject to any disclaimer, the term of this patent is extended or adjusted under 35 U.S.C. 154(b) by 142 days.

(21) Appl. No.: 10/898,659

(22) Filed: Jul. 23, 2004

(65) Prior Publication Data

US 2005/0112397 A1 May 26, 2005

Related U.S. Application Data

(60) Provisional application No. 60/584,786, filed on Jul. 1, 2004, provisional application No. 60/551,163, filed on Mar. 8, 2004, provisional application No. 60/505,087, filed on Sep. 23, 2003, provisional application No. 60/490,061, filed on Jul. 24, 2003.

(51) Int. Cl.
*B32B 3/26* (2006.01)

(52) U.S. Cl. .................. 428/304.4; 428/131; 428/134; 428/137; 428/138; 428/310.5

(58) Field of Classification Search ............. 428/304.4, 428/131, 134, 137, 138, 310.5
See application file for complete search history.

(56) References Cited

U.S. PATENT DOCUMENTS 3,584,972 A  6/1971  Bratkovich et al.

(Continued)

FOREIGN PATENT DOCUMENTS

CA  2 445 523  11/2002

(Continued)

OTHER PUBLICATIONS

Bobyn, JD et al., Characterization of a New Porous Tantalum Biomaterial for Reconstructive Orthopedics, 1999; Annual Meeting of the American Academy or Orthopedic Surgeons.

(Continued)

*Primary Examiner*—Jennifer McNeil
*Assistant Examiner*—Gordon R. Baldwin
(74) *Attorney, Agent, or Firm*—Baker & Hostetler LLP

(57) ABSTRACT

A porous structure having a plurality of bonded sheets each sheet having at least one aperture that partially overlaps an aperture of at least one other sheet. A method of producing a porous structure including stacking a plurality of sheets each sheet having a multiplicity of apertures, and bonding each sheet to its adjoining sheet. An open-pore network structure having a multiplicity of sheets each having a repeatable pattern. At least a portion of each sheet is bonded to the web of an adjacent sheet. The porous area of at least one of the sheets is askew to the porous area of at least another of the sheets. An open-pore structure having a multiplicity of bonded sheets, each sheet having a repeatable pattern defining a multiplicity of perforations, and a plurality of apertures defined by the repeatable pattern, the apertures extending through the perforations of at least two adjacent plates.

9 Claims, 48 Drawing Sheets

U.S. PATENT DOCUMENTS

| | | |
|---|---|---|
| 3,677,795 A | 7/1972 | Bokros et al. |
| 3,855,638 A | 12/1974 | Pilliar |
| 3,905,777 A | 9/1975 | Lacroix |
| 3,933,473 A | 1/1976 | Dickson |
| 3,948,793 A | 4/1976 | Anderson |
| 4,051,598 A | 10/1977 | Sneer |
| 4,145,764 A | 3/1979 | Suzuki et al. |
| 4,156,296 A | 5/1979 | Johnson et al. |
| 4,392,828 A | 7/1983 | Ehrnford |
| 4,439,152 A | 3/1984 | Small |
| 4,542,539 A | 9/1985 | Rowe, Jr. et al. |
| 4,570,271 A | 2/1986 | Sump |
| 4,608,052 A | 8/1986 | Van Kampen et al. |
| 4,636,219 A | 1/1987 | Pratt et al. |
| 4,644,627 A | 2/1987 | Palazzo |
| 4,644,942 A | 2/1987 | Sump |
| 4,655,825 A | 4/1987 | Hard et al. |
| 4,660,755 A | 4/1987 | Farling et al. |
| 4,668,557 A | 5/1987 | Lakes |
| 4,716,064 A | 12/1987 | Holzl et al. |
| 4,722,756 A | 2/1988 | Hard |
| 4,728,364 A | 3/1988 | Bania |
| 4,794,979 A | 1/1989 | Gassner et al. |
| 4,837,089 A | 6/1989 | Araki et al. |
| 4,839,215 A * | 6/1989 | Starling et al. ............. 428/131 |
| 4,842,517 A | 6/1989 | Kawahara et al. |
| 4,863,474 A | 9/1989 | Brown et al. |
| 4,904,262 A | 2/1990 | Bensmann |
| 4,955,911 A | 9/1990 | Frey et al. |
| 4,957,819 A | 9/1990 | Kawahara et al. |
| 4,964,801 A | 10/1990 | Kawahara et al. |
| 4,976,738 A | 12/1990 | Frey et al. |
| 4,978,355 A | 12/1990 | Frey et al. |
| 4,990,394 A | 2/1991 | Shoher et al. |
| 5,024,670 A | 6/1991 | Smith et al. |
| 5,030,233 A | 7/1991 | Ducheyne |
| 5,035,713 A | 7/1991 | Friis |
| 5,037,273 A | 8/1991 | Krueger et al. |
| 5,037,438 A | 8/1991 | Davidson |
| 5,042,560 A | 8/1991 | Ahlers |
| 5,049,074 A | 9/1991 | Otani et al. |
| 5,061,914 A | 10/1991 | Busch et al. |
| 5,075,177 A | 12/1991 | Tanaka et al. |
| 5,085,953 A | 2/1992 | Akridge et al. |
| 5,108,432 A | 4/1992 | Gustavson |
| 5,108,435 A | 4/1992 | Gustavson et al. |
| 5,112,354 A | 5/1992 | Sires |
| 5,156,625 A | 10/1992 | Marchetti et al. |
| 5,167,502 A | 12/1992 | Kawahara et al. |
| 5,180,083 A | 1/1993 | Carlson |
| 5,227,148 A | 7/1993 | Akridge et al. |
| 5,240,672 A | 8/1993 | Yang |
| 5,248,386 A | 9/1993 | Dastolfo, Jr. et al. |
| 5,248,475 A | 9/1993 | Feldstein |
| 5,249,621 A | 10/1993 | Aghajanian et al. |
| 5,258,098 A | 11/1993 | Wagner et al. |
| 5,282,861 A | 2/1994 | Kaplan |
| 5,290,339 A | 3/1994 | Gallup et al. |
| 5,298,283 A | 3/1994 | Rocazella et al. |
| 5,343,202 A | 8/1994 | Bell |
| 5,348,788 A | 9/1994 | White |
| 5,380,328 A | 1/1995 | Morgan |
| 5,433,750 A | 7/1995 | Gradinger et al. |
| 5,439,744 A | 8/1995 | Claar et al. |
| 5,441,670 A | 8/1995 | Shimamune et al. |
| 5,443,510 A | 8/1995 | Shetty et al. |
| 5,445,688 A | 8/1995 | Gigliotti, Jr. et al. |
| 5,455,100 A | 10/1995 | White |
| 5,464,440 A | 11/1995 | Johansson |
| 5,496,372 A | 3/1996 | Hamamoto et al. |
| 5,503,655 A | 4/1996 | Joseph |
| 5,503,941 A | 4/1996 | Pruyn |
| 5,505,248 A | 4/1996 | Aghajanian et al. |
| 5,507,815 A | 4/1996 | Wagner et al. |
| 5,518,777 A | 5/1996 | Shimamune et al. |
| 5,519,225 A | 5/1996 | Mohr et al. |
| 5,522,894 A | 6/1996 | Draenert |
| 5,558,961 A | 9/1996 | Doeff et al. |
| 5,564,064 A | 10/1996 | Martin |
| 5,576,710 A | 11/1996 | Broderick et al. |
| 5,582,630 A | 12/1996 | Lam et al. |
| 5,616,478 A | 4/1997 | Chetverin et al. |
| 5,679,270 A | 10/1997 | Thornton et al. |
| 5,702,449 A | 12/1997 | McKay |
| 5,732,469 A | 3/1998 | Hamamoto et al. |
| 5,759,400 A | 6/1998 | Fanning |
| 5,766,263 A | 6/1998 | Grundei et al. |
| 5,780,765 A | 7/1998 | Dyben |
| 5,807,406 A | 9/1998 | Brauker et al. |
| 5,843,289 A | 12/1998 | Lee et al. |
| 5,865,237 A | 2/1999 | Schorghuber et al. |
| 5,922,029 A | 7/1999 | Wagner et al. |
| 5,961,554 A | 10/1999 | Janson et al. |
| 5,984,971 A | 11/1999 | Faccioli et al. |
| 6,001,568 A | 12/1999 | Chetverin et al. |
| 6,008,430 A | 12/1999 | White |
| 6,010,336 A | 1/2000 | Shimotoso et al. |
| 6,048,204 A | 4/2000 | Klardie et al. |
| 6,049,054 A | 4/2000 | Panchison et al. |
| 6,051,117 A | 4/2000 | Novak et al. |
| 6,066,176 A | 5/2000 | Oshida |
| 6,087,024 A | 7/2000 | Whinnery et al. |
| 6,087,553 A | 7/2000 | Cohen et al. |
| 6,113,982 A | 9/2000 | Claar et al. |
| 6,120,539 A | 9/2000 | Eldridge et al. |
| 6,123,899 A | 9/2000 | Setzer et al. |
| 6,148,515 A | 11/2000 | Suzuki et al. |
| 6,152,982 A | 11/2000 | Froes et al. |
| 6,162,310 A | 12/2000 | Tseng |
| 6,193,762 B1 | 2/2001 | Wagner et al. |
| 6,197,251 B1 | 3/2001 | Hashimoto et al. |
| 6,206,924 B1 | 3/2001 | Timm |
| 6,214,049 B1 | 4/2001 | Gayer et al. |
| 6,234,242 B1 | 5/2001 | Sehmbey et al. |
| 6,250,362 B1 | 6/2001 | Rioja et al. |
| 6,264,724 B1 | 7/2001 | Rosenfellner et al. |
| 6,275,371 B1 | 8/2001 | Yoshio et al. |
| 6,280,478 B1 | 8/2001 | Richter et al. |
| 6,296,667 B1 | 10/2001 | Johnson et al. |
| 6,309,595 B1 | 10/2001 | Rosenberg et al. |
| 6,312,473 B1 | 11/2001 | Oshida |
| 6,328,765 B1 | 12/2001 | Hardwick et al. |
| 6,357,332 B1 | 3/2002 | Vecchio |
| 6,358,345 B1 | 3/2002 | Tseng |
| 6,375,779 B1 | 4/2002 | Melquist et al. |
| 6,375,905 B1 | 4/2002 | Moini et al. |
| 6,379,816 B1 | 4/2002 | De Loose et al. |
| 6,397,450 B1 | 6/2002 | Ozmat |
| 6,411,248 B1 | 6/2002 | Barbour et al. |
| 6,423,095 B1 | 7/2002 | Van Hoeck et al. |
| 6,444,007 B1 | 9/2002 | Knott et al. |
| 6,444,166 B1 | 9/2002 | Garrett |
| 6,458,316 B1 | 10/2002 | Garrett |
| 6,471,993 B1 | 10/2002 | Shastri et al. |
| 6,494,914 B2 | 12/2002 | Brown et al. |
| 6,520,997 B1 | 2/2003 | Pekkarinen et al. |
| 6,533,065 B2 | 3/2003 | Zanker |
| 6,585,111 B1 | 7/2003 | Shervington et al. |
| 6,585,151 B1 | 7/2003 | Ghosh |
| 6,585,772 B2 | 7/2003 | Hunter et al. |
| 6,592,787 B2 | 7/2003 | Pickrell et al. |
| 6,599,322 B1 | 7/2003 | Amrich et al. |
| 6,610,904 B1 | 8/2003 | Thomas et al. |
| 6,620,332 B2 | 9/2003 | Amrich |

| | | |
|---|---|---|
| 6,652,586 B2 | 11/2003 | Hunter et al. |
| 6,659,162 B2 | 12/2003 | Frommeyer et al. |
| 6,660,224 B2 | 12/2003 | Lefebvre et al. |
| 6,673,075 B2 | 1/2004 | Santilli |
| 6,679,914 B1 | 1/2004 | Gabbay |
| 6,679,916 B1 | 1/2004 | Frankle et al. |
| 6,698,331 B1 | 3/2004 | Yu et al. |
| 6,737,053 B1 | 5/2004 | Goh et al. |
| 6,756,932 B1 | 6/2004 | Barker et al. |
| 6,827,743 B2 | 12/2004 | Eisermann et al. |
| 2001/0013166 A1 | 8/2001 | Yan |
| 2002/0106611 A1 | 8/2002 | Bhaduri et al. |
| 2002/0198589 A1 | 12/2002 | Leong |
| 2003/0014123 A1 | 1/2003 | Copf et al. |
| 2003/0065401 A1 | 4/2003 | Amrich et al. |
| 2003/0100948 A1 | 5/2003 | Goulet et al. |
| 2003/0125808 A1 | 7/2003 | Hunter et al. |
| 2003/0173459 A1 | 9/2003 | Fanucci et al. |
| 2003/0220696 A1 | 11/2003 | Levine et al. |
| 2003/0233149 A1 | 12/2003 | Hodorek |
| 2004/0067249 A1 | 4/2004 | Goulet et al. |
| 2004/0075023 A1 | 4/2004 | Assler et al. |
| 2004/0170946 A1 | 9/2004 | Lyren |
| 2004/0186553 A1 | 9/2004 | Yan |
| 2004/0193270 A1 | 9/2004 | DiMauro et al. |
| 2004/0210316 A1 | 10/2004 | King et al. |
| 2004/0220672 A1 | 11/2004 | Shadduck |
| 2004/0243241 A1 | 12/2004 | Istephanous et al. |
| 2004/0243246 A1 | 12/2004 | Lyren |

FOREIGN PATENT DOCUMENTS

| | | |
|---|---|---|
| EP | 0 577 178 A1 | 1/1994 |
| EP | 0 984 745 | 3/2000 |
| GB | 2 059 267 A | 4/1981 |
| GB | 2093701 A | 9/1982 |
| GB | 2 142 544 A | 1/1985 |
| JP | 3 049766 | 3/1991 |

OTHER PUBLICATIONS

R&F Products—RF Core Microwave Absorber; http://www.randf.com/rf_core.html; date printed by applicant: Dec. 28, 2004.

510 (k) Summary of Safety and Effectiveness, The Trabecular Metal Monoblock Cup Special 510(k) Premarket Notification, Jun. 12, 2002, Allendale, NJ.

Nebosky, Paul S., Jr., Abstract: Forming of Tantalum Foam, The AME Graduate Student Conference 2002, http://www.nd.edu/~npetroff/gsc02/abstracts/pnebosky.htm; date printed by applicant: Jul. 23, 2003.

Overview. http://www.implex.com/h1_2.html; date printed by applicant: Jul. 23, 2003.

Hedrocel Stability Characteristics, http://www.implex.com/images/h114.jpg; date printed by applicant: Jul. 23, 2003.

Hedrocel Physical Properties, http://www.implex.com/images/h112.jpg; date printed by applicant: Jul. 23, 2003.

Hedrocel Porous Tantalum, http://www.implex.com/images/h111.jpg; date printed by applicant: Jul. 23, 2003.

Hedrocel®—A Breakthrough Trabecular Metal that Welcomes Ingrowth; http://www.implex.com/h1_1.html; date printed by applicant: Jul. 23, 2003.

Article: Northwestern Memorial Hospital a Leader in State-of-the-Art Hip Replacements; http://wwwsearch.nmh.or/webpages/for_the_press/in_the_news/in_the_news_hedrocel.ht . . . ;Feb. 26, 2001.

Skeletech, Inc., Orthopaedics & Tissue Engineering, Technical Note, Bothell, WA ; publication date unknown.

International Search Report for PCT/US04/23514 dated Mar. 9, 2005.

* cited by examiner

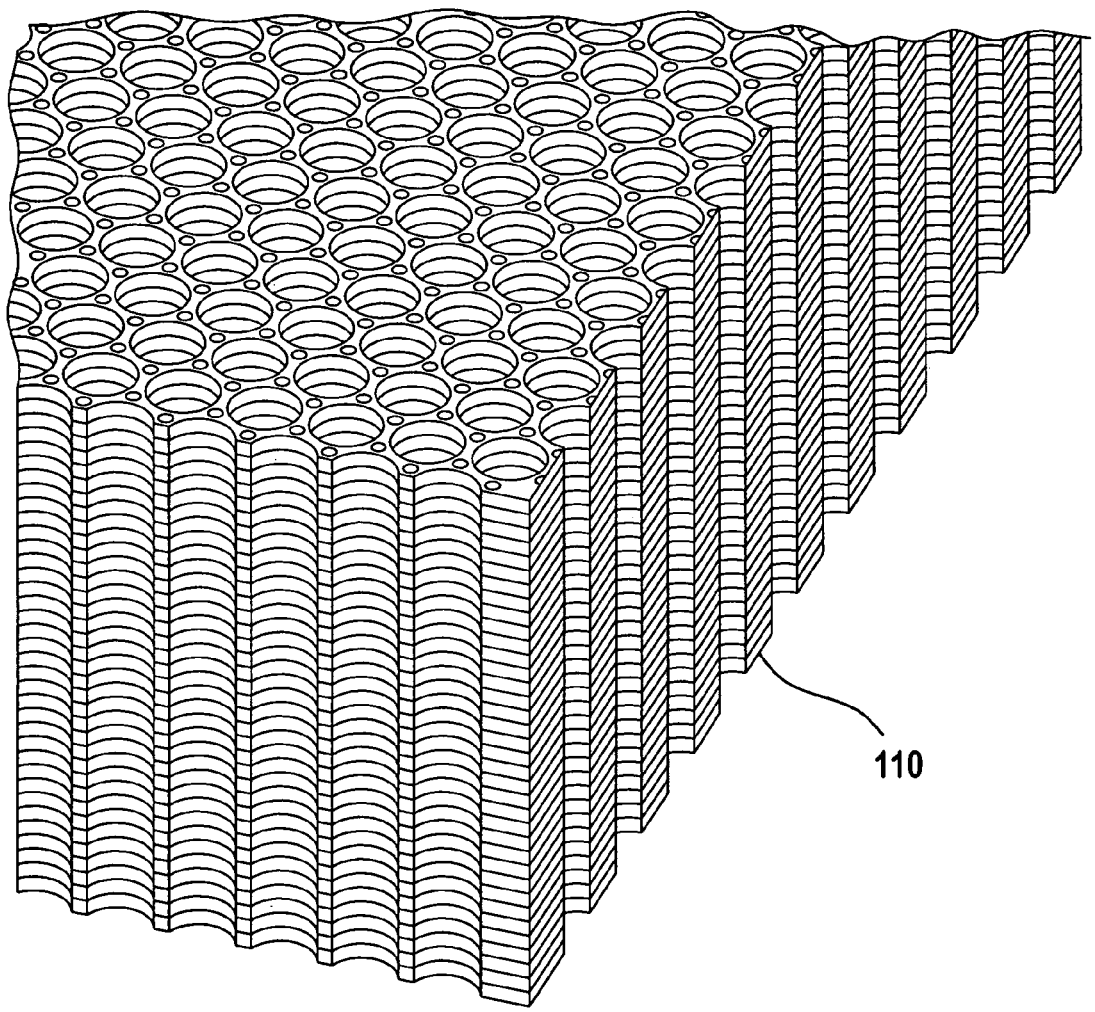
FIG. 1 D1

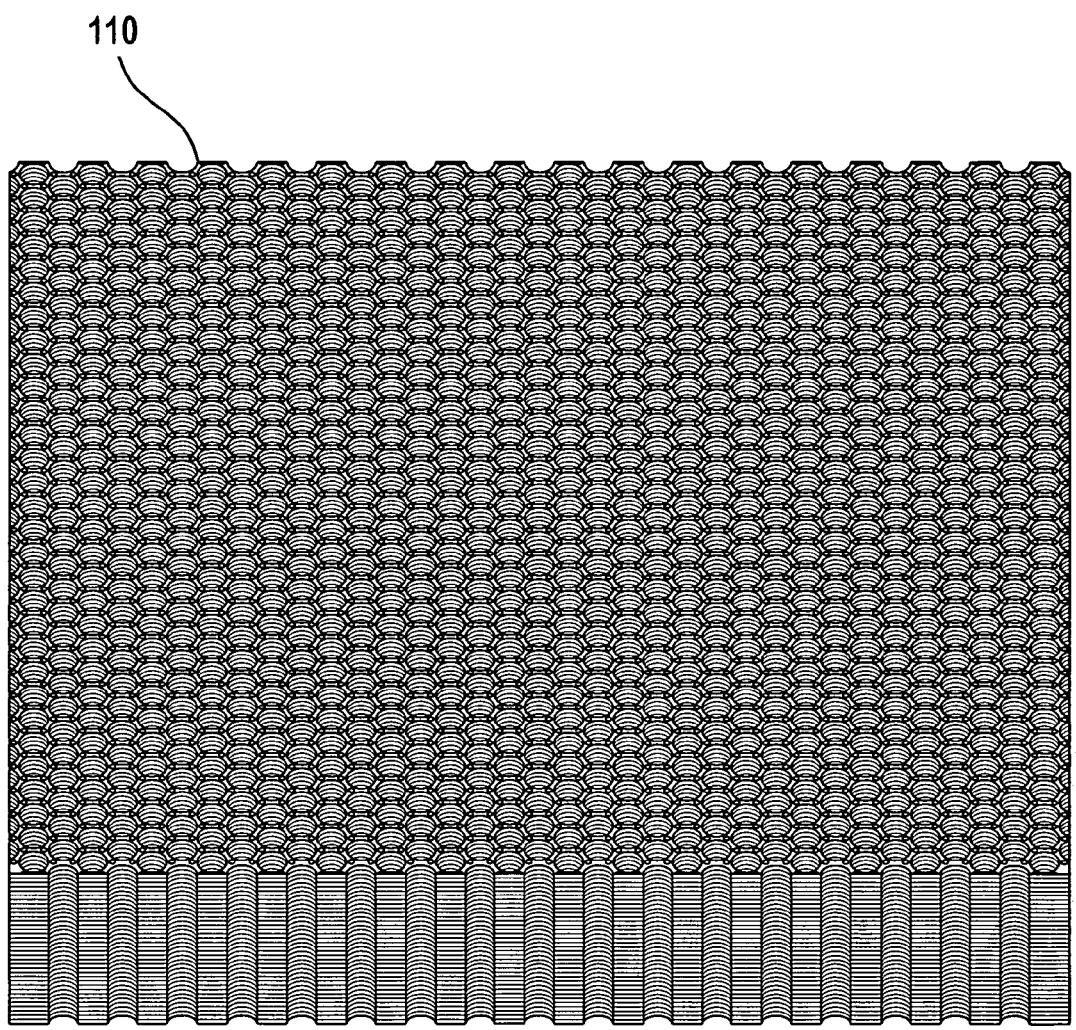
FIG. 1D2

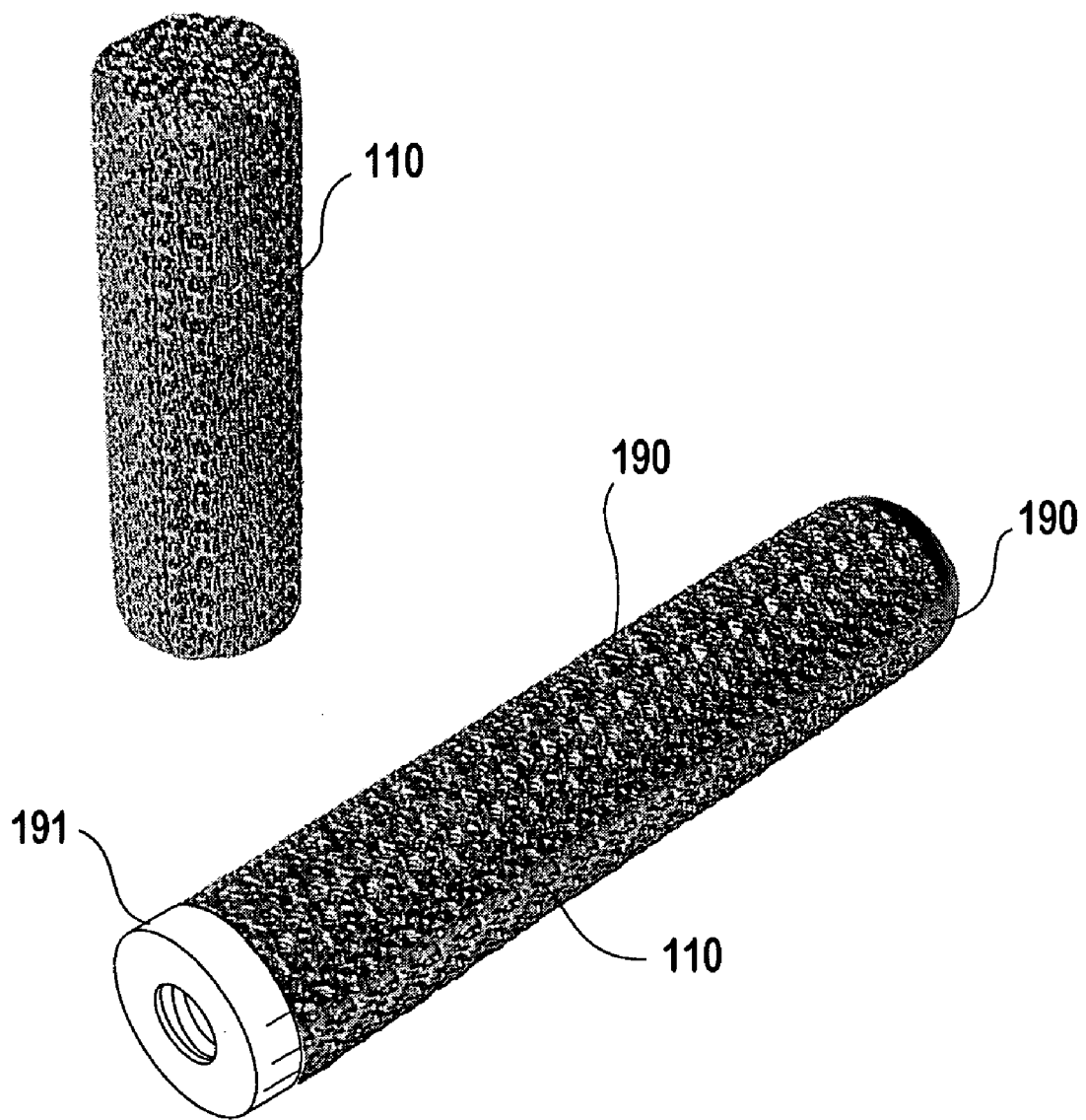
FIG. 1F1

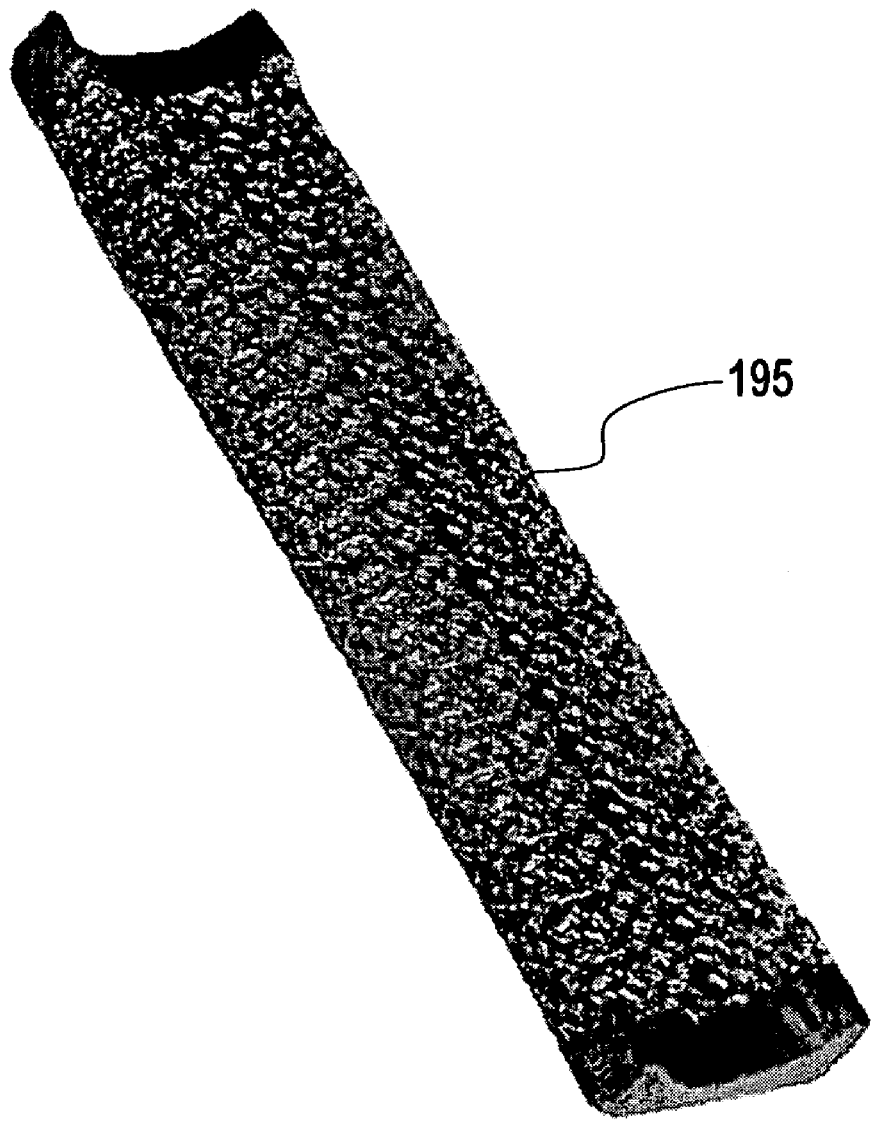
FIG. 1F2

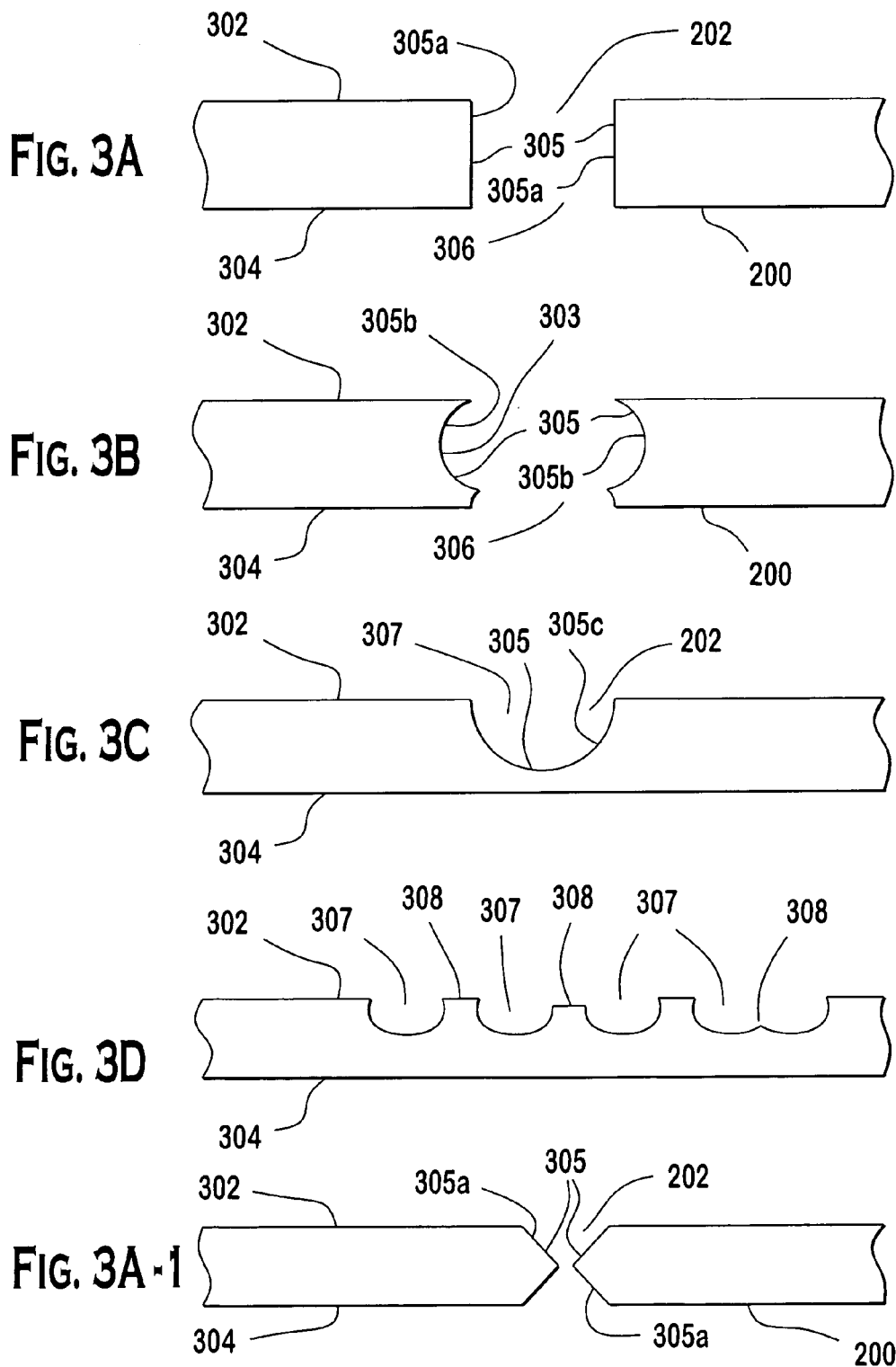

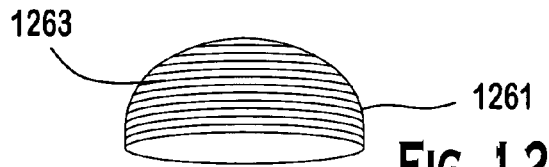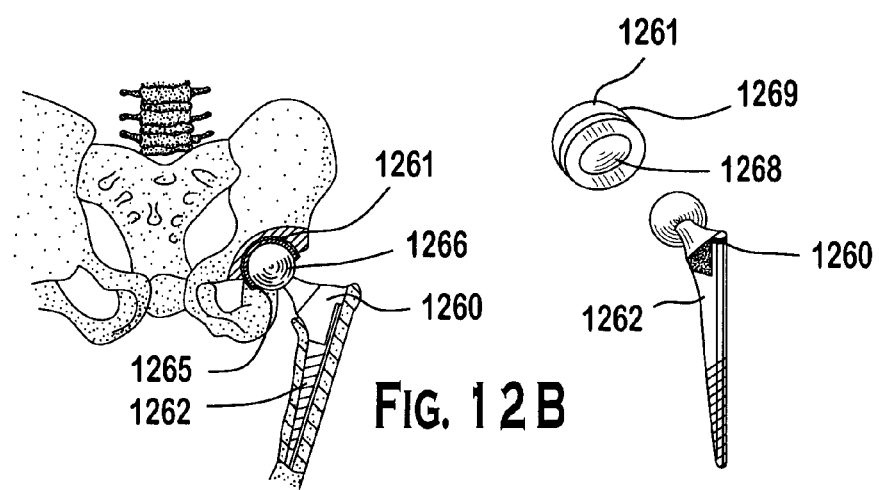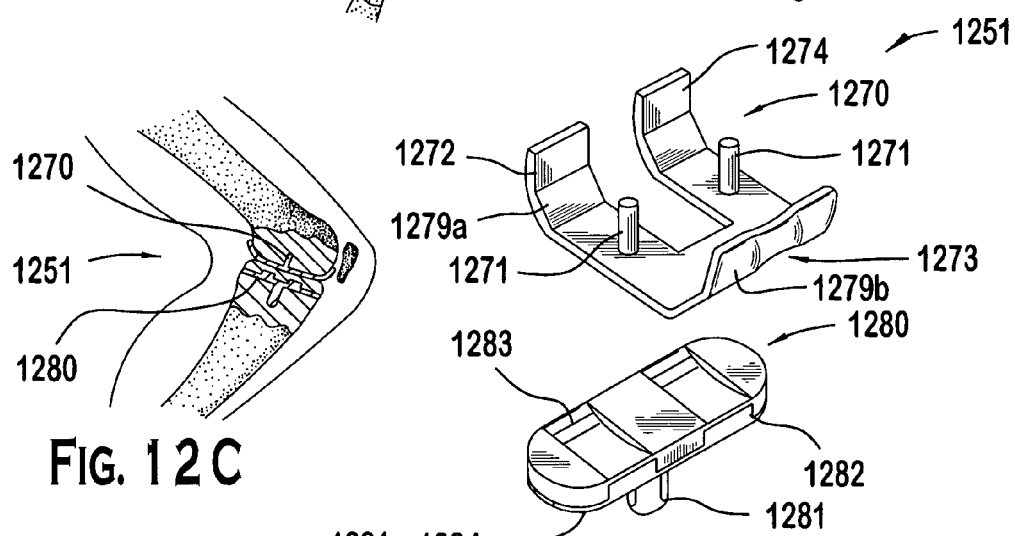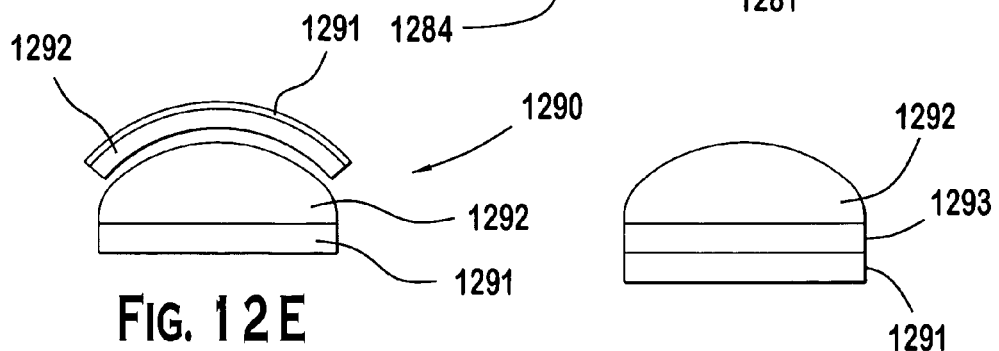

ASSEMBLED NON-RANDOM FOAMS

STATEMENT OF RELATED APPLICATIONS

This application claims priority to International PCT Application No. PCT/US04/23514, filed on Jul. 22, 2004, entitled "Assembled Non-Random Foams," which is hereby incorporated by reference. This application also claims priority to U.S. Provisional Application No. 60/584,786 filed on Jul. 1, 2004; 60/551,163, filed on Mar. 8, 2004; 60/505,087, filed on Sep. 23, 2003; and 60/490,061, filed on Jul. 24, 2003, all of which are hereby incorporated by reference in their entirety.

SUMMARY OF THE PREFERRED EMBODIMENTS

In one embodiment, the present invention is a porous structure having a plurality of bonded sheets each sheet having at least one aperture that partially overlaps at least one aperture of at least one other sheet. A preferred embodiment of the present invention is a porous structure having a plurality of bonded sheets having at least one aperture and having a transverse dimension and a longitudinal dimension that is no more than approximately four times the transverse dimension. In one embodiment, the structure is a cancellous structure. In one embodiment, the transverse and longitudinal dimensions are between approximately 100 microns and 5000 microns and preferably between 100 microns and 450 microns. In one embodiment, the longitudinal and transverse dimensions are sufficient to promote the ingrowth of tissue. Preferably the sheets have a multiplicity of apertures. In a further preferred embodiment the resulting three-dimensional structure has a porosity between 5% and 90%, or higher. In a still further preferred embodiment the sheets have a porosity of between 5% and 90%. In a preferred embodiment the porosity of the sheets is between 70% and 85%. The apertures can have any shape or dimension. In another embodiment, the porosity of the sheets is between 90% and 95% porosity. In another preferred embodiment, apertures in each sheet are defined by a regular repeatable pattern. In one embodiment, the regular repeatable pattern is pseudorandom. In yet another preferred embodiment, the apertures of at least one sheet are arranged in substantially the same regular repeating pattern as another sheet. In a still further preferred embodiment a first sheet is aligned askew to a second sheet. In a still further preferred embodiment, a first sheet is aligned offset to a second sheet.

In a still further preferred embodiment, the structure includes a refractory metal such as titanium, tantalum, zirconium, oxidized zirconium, hafnium, platinum, rhodium, niobium and alloys thereof. In other embodiments, the structure is cobalt-chrome or chrome-cobalt-molybdenum alloys. In another embodiment, the structure includes a material such as gold, aluminum, stainless steel and alloys thereof. In another preferred embodiment, the structure is porous in three-dimensions (e.g., fluid can flow through the structure in three dimensions). In another preferred embodiment, at least one aperture extends to an edge of at least one sheet or the structure. In another preferred embodiment the structure includes at least one edge that is substantially solid (e.g., with any aperture adjacent to the edge). In another preferred embodiment, the porous structure has a differential porosity. In another preferred embodiment, the porous structure has the differential porosity that is a stepped differential porosity. In another preferred embodiment, the porous structure has a graduated porosity. In another preferred embodiment, the porous structure has adjacent sheets with differing aperture-to-web ratios. In another preferred embodiment, the porous structure has a first sheet with a thickness that is different from a second sheet.

A preferred method of producing a porous structure includes designing one or more sheet patterns (e.g., a pattern of apertures and webs); applying the one or more patterns to a plurality of sheets; forming apertures in the plurality of sheets; stacking the plurality of sheets; and bonding the sheets; and post processing the sheets (e.g., each sheet or the bonded sheets). In a further preferred embodiment, the bonding method is chemical bonding. In a still further preferred embodiment, the bonding method is mechanical bonding. In a yet a further preferred embodiment, the bonding method is physical bonding or vacuum diffusion bonding. In one embodiment, the porous structure has a plurality of sheets in a preformed shape. Preferably the preformed shape is configured to connect to a solid material. In one embodiment the preformed shape is configured to connect to a component of a medical implant such as an orthopedic implant, a spinal implant, a dental implant a digital implant, an augmentation implant or an articulating implant.

In one embodiment, there is a composite material having a porous structure and a solid material. The porous structure and solid material are substantially similar or substantially dissimilar materials.

In one embodiment, there is a porous structure that includes at least one barrier layer that is preferably, solid, semi-solid and/or textured.

In one embodiment, the porous structure has at least one sheet that is textured. In a further embodiment, a first sheet is bonded to second sheet and the first sheet and second sheets are different materials. In one embodiment, a first textured sheet is bonded to a second non-textured sheet. Textured sheets are preferably configured to effect the surface roughness of the cancellous structure.

In one embodiment, the porous structure has a tissue engaging surface, a polymer engaging structure, and/or a compliant surface engaging structure. In one embodiment, the porous structure has at least one sheet that is polymer.

Preferably the porous structure has a textured sheet that is configured to effect the surface roughness of the porous structure. The porous structure preferably has a tissue engaging surface. In one embodiment, the porous structure is configured to accept bone ingrowth.

Preferably, the porous structure is configured to form a component of a medical implant. A preferred method of producing a porous structure includes a post processing step including machining the bonded plates. In another preferred embodiment the post-processing step includes etching (e.g., any type of etching including photochemical or wet etching). In another preferred embodiment, the post-processing step includes increasing the porosity of the porous structure.

In one embodiment the invention includes is a cancellous structure that includes a plurality of stacked sheets, each sheet having a multiplicity of webs and apertures. At least one web of each sheet of the cancellous structure is bonded to at least one web of an adjacent sheet. The bonded webs of the cancellous structure are configured to form at least one structural element and the apertures of adjacent sheets have an alignment configured to form a plurality of tortuous pores throughout the cancellous structure. Preferably the cancellous structure is configured to approximate at least one predetermined mechanical property. In one embodiment, the cancellous structure has at least one structural element that is a post, a beam or a scaffold.

In another preferred embodiment, a tissue engaging structure includes a plurality of stacked bonded sheets having a plurality of apertures. The apertures of the stacked sheets have an alignment configured to form a plurality of tortuous pores through the plurality of stacked sheets and, the plurality of apertures are dimensioned to accommodate tissue ingrowth. In some embodiments, the sheets are stacked in an aligned or misaligned orientation such that the plurality of apertures have an alignment configured to create tortuous pores.

In another embodiment, there is an orthopedic implant having a first and second tissue engaging bone substitute component. Each bone substitute has a plurality of sheets with a multiplicity of webs defining a multiplicity of apertures. The plurality of sheets preferably are bonded together to form an open pore structure. The orthopedic implant also has an elastic (e.g., polymer) component at least partially infused within a portion of the first and second tissue engaging bone substitute components. In one embodiment, the elastic component is polymer such as UHMWPE, PTFE, HDPE, hydroxyapetite, PEEK, polyglycolic acid, polylactic acid, polyoxyethylenes, and co-polymers thereof.

A preferred method of producing a cancellous structure includes stacking a plurality of sheets each sheet having a multiplicity of apertures and bonding each sheet to its adjoining sheet. In one embodiment, the bonding is chemical bonding, mechanical bonding, physical bonding, diffusion bonding, soldering and/or brazing. In one embodiment, the method includes post-processing the bonded sheets preferably by etching, increasing the porosity of the porous structure, and/or by infusing at least a portion of the plurality of sheets with polymer. In one embodiment, the infused polymer is UHMWPE, PTFE, HDPE, hydroxyapetite, PEEK, polyglycolic acid, polylactic acid, polyoxyethylenes, and/or co-polymers thereof. In one embodiment, the multiplicity of apertures are arranged in a regular repeating pattern and the stacking includes orienting the regular repeating pattern of a first of the plurality of sheets askew to the regular repeating pattern of a second of the plurality of sheets. In one embodiment of the method, the sheets comprise a refractory metal such as titanium, tantalum, zirconium, oxidized zirconium, hafnium, platinum, rhodium, niobium and alloys thereof. In another embodiment, the plurality of sheets are gold, aluminum, stainless steel and alloys thereof. In yet another embodiment, the plurality of sheets are cobalt-chrome or chrome-cobalt-molybdenum alloys. In one embodiment, the stacking includes assembling the sheets in a fixture that is not flat. In one embodiment the fixture is a rolled fixture. In one embodiment, the stacking includes assembling the sheets in a mold.

A preferred embodiment of the present invention includes, a porous structure having a lattice stacked to form the porous structure and a bond for securing the lattice.

Another preferred embodiment of the porous structure includes an open-pore network structure having a multiplicity of stacked sheets each having a web in a regular and/or irregular pattern and at least one web of each sheet is bonded to a web of an adjacent sheet and the web of at least one of stacked sheets is askew to the web of at least another of the stacked sheets. In one embodiment, the web is a serpentine web.

Yet another preferred embodiment includes an open-pore structure having a multiplicity of stacked bonded sheets, each sheet having a reticulated web defining a multiplicity of perforations, and a plurality of apertures defined by the web. In one embodiment, the apertures extending through the perforations of at least three adjacent plates.

BRIEF DESCRIPTION OF THE DRAWINGS

Reference is made to the accompanying drawings in which are shown illustrative embodiments of the invention, from which its novel features and advantages will be apparent.

In the drawings:

FIGS. 1A–1G show samples of porous structures according to the present invention.

FIGS. 3A–D show exemplary embodiments of porous sheets according to the present invention.

FIG. 3A-1 shows an exemplary embodiment of a porous sheet according to the present invention.

FIG. 6A-1 shows a method of forming a porous structure according to the present invention.

FIG. 6A-2 shows one embodiment of a series of open pore sheets, and an open pore structure of stacked sheets according to the present invention.

FIGS. 12B–E show hip and knee implants including a porous structure according to the present invention.

DESCRIPTION OF THE PREFERRED EMBODIMENTS

Figure 1B:
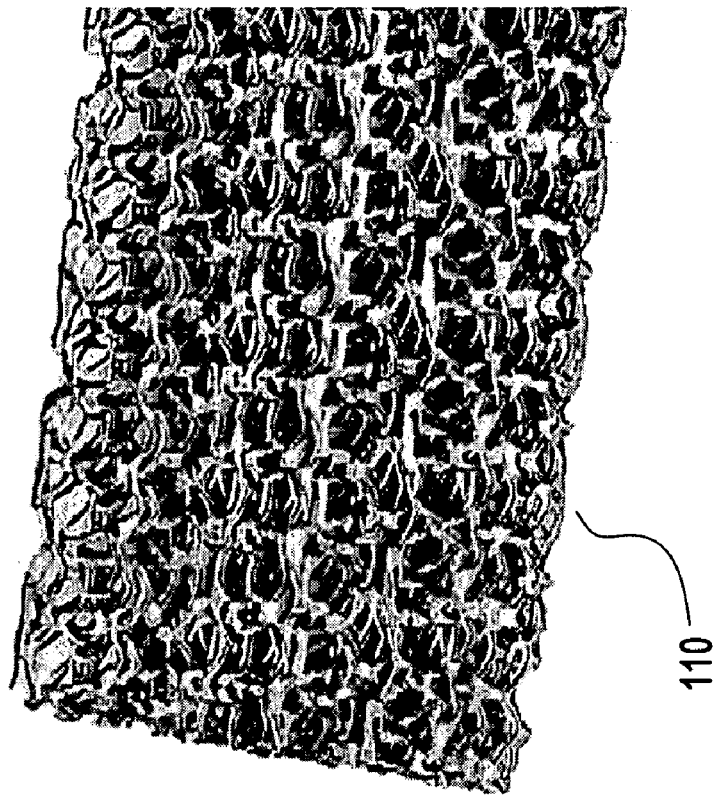

There is a need for lightweight open pore material with high strength that can be rapidly produced at very low cost. The structure of the present invention has applications as medical implants (e.g., implants with which tissue ingrowth is desired) including, spinal fusion and articulating devices, cancellous bone substitutes, trabecula bone substitutes, reconstructive trauma or aesthetic surgery implants and prosthetics for hips, knees, ankles, shoulders, fingers, toes, elbows or any other application that requires attachment to tissue such as bone or ligaments. In one embodiment of medical applications of the open pore structure of the present invention, such as in medical implants, the open pore structure of the present invention is preferably engineered to mimic one or more cell structures of the host material (e.g., cancellous bone, hard tissue, soft tissue, ligament).

The present invention is also useful for any application calling for high strength lightweight materials such as aerospace, construction and automotive applications.

Reference will now be made in detail to preferred embodiments of the present invention, examples of which are illustrated in the accompanying drawings. Wherever possible, the same reference numbers will be used throughout the drawings to refer to the same or like parts. To provide a thorough understanding of the present invention, numerous specific details of preferred embodiments are set forth including material types, dimensions, and procedures. Practitioners having ordinary skill in the art, will understand that the embodiments of the invention may be practiced without many of these details. In other instances, well-known devices, methods, and processes have not been described in detail to avoid obscuring the invention.

FIGS. 1A–1G illustrate a porous structure 110 of the present invention. Porous structure 110 is lightweight compared to a solid structure formed of the same materials and having the same dimensions. In one embodiment, porous structure 110 has a density that is approximately 15% to 50% that of a corresponding solid volume made from the same material. In one embodiment, porous structure 110 maintains a high dimensional stability under load. For example, the size, shape and porosity of porous structure 110 remains substantially unchanged under heavy load and/or machining (e.g. cold working).

In a preferred embodiment, porous structure 110 of the present invention is used wherever a prosthesis is to have contact with bone or tissue to stabilize the prosthesis and induce an integrated bond between the prosthesis and the host tissue.

Porous structure 110 preferably includes a plurality of stacked bonded sheets 200a–c (e.g., layers, foils, plates). Each sheet 200a–c (see, e.g., FIG. 2A–2C) preferably has at least one aperture 202 that partially overlaps an aperture 202 of at least one other sheet (e.g., of an adjacent or non-adjacent sheet) when two or more sheets 200a–c are stacked on one another. In a preferred embodiment, a resulting porous structure 110 includes a sponge-like highly porous three-dimensional lattice having tortuous pores 210 that propagate through structure 110. In one embodiment, at least some of apertures 202 are aligned in substantially perfect register to achieve a channel through at least a portion of the porous structure 110 (e.g., as shown in more detail below in FIGS. 1D2, 1E and 6B). In a preferred embodiment, web 204 of adjoining layers are aligned to achieve a structural element through at least a portion of porous structure 110 (e.g., as discussed in more detail below in connection with FIG. 6B). In one embodiment, web 204 is a serpentine web.

Materials for Forming Sheets and Structures

Figure 2A:
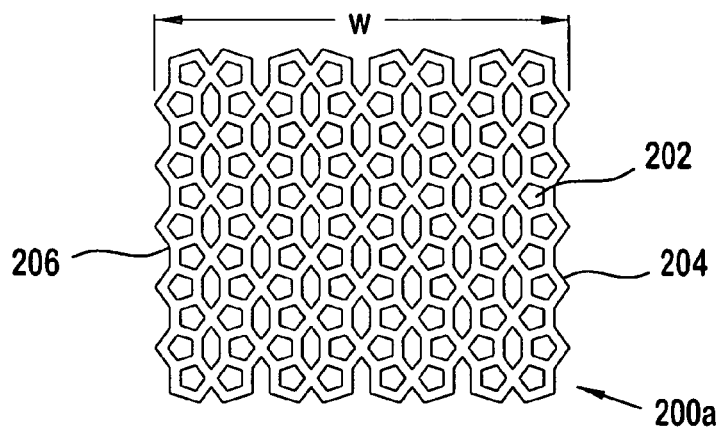
FIGS. 2A–C show porous sheets according to the present invention.
Figure 2B:
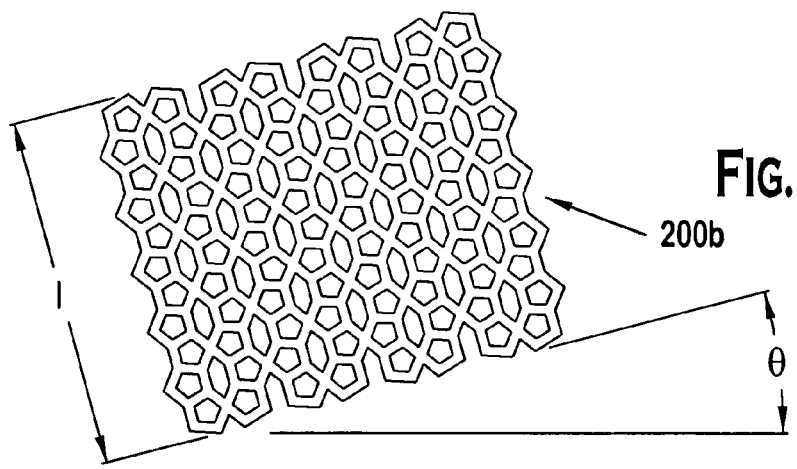
Figure 2C:
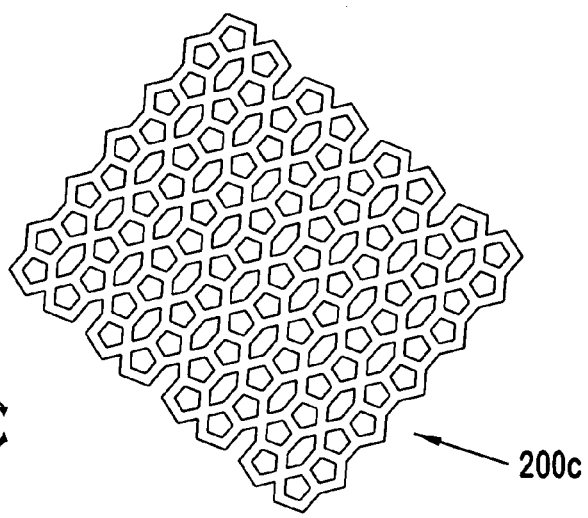

In FIG. 2A–2C, there is illustrated sheet 200a, 200b, and 200c. Sheets 200a–c may be formed from any of the materials that may be useful for constructing a porous structure. In one embodiment sheet 200a–c of porous structure 110 is of the same material. In other embodiments, two or more of sheets 200a–c of porous structure 110 are of different materials. In one embodiment, two or more sheets 200a–c of differing materials are bonded together to form porous structure 110. In some embodiments sheets 200a–c are made from non-metals such as ceramics, glass, polymer, paper or other manmade or natural materials. In one embodiment, porous structure 110 is formed by combining sheets of different materials (e.g., glass, ceramic, metal, polymer, or combinations thereof) to form a hybrid structure. In one embodiment one or more of sheets 200a–c are textured. For example, textured sheets are bonded to textured or non-textured sheets. In one embodiment, at least one of sheets 200a–c is a textured sheet configured to effect the surface roughness of porous structure 110.

In one embodiment, porous structure 110 can be made in any size from any metal or non-metal material. In some embodiments, porous structure 110 and/or sheets 200a–c (e.g., as shown in FIG. 2A–D) are made from base metals such as refractory metals (e.g., titanium, tantalum, zirconium, hafnium, platinum, rhodium, niobium and alloys thereof) gold, cobalt-chrome alloys, chrome-cobalt-molybdenum alloys, aluminum, stainless steel, any alloys thereof or any other metal or alloy that may be chosen for its bonding properties, chemical inertness, bio-compatibility, mechanical strength or properties that would render porous structure 110 (e.g., in the form of foam or sponge) made of such material a useful product for a particular application.

In some embodiments, porous structure 110 and/or sheet 200a–c are made from non-metals such as polymers (e.g., ultra high molecular weight polyethylene (UHMWPE), polytetrafluoroethylene (PTFE), high density polyethylene (HDPE), hydroxyapetite, polyether ether ketone (PEEK), polyglycolic acid, polylactic acid, polyoxyethylenes and similar materials and co-polymers thereof). In one embodiment, sheets 200a and/or structure 110 is formed from natural or synthetic, resorbable polymers preferably biocompatible resorbable polymers.

In one embodiment, sheet 200 and/or structure 110 is formed from woven or non-woven mesh.

In another embodiment, natural fibrous, protein-based or cellulosic materials such as papers, meshes, leathers, glass films can be made into sheets and thereafter formed into porous structure 110 according to the present invention. In one embodiment, sheets 200 and/or structure 110 is made from carbonaceous materials.

In one embodiment, porous structure 110 is oxidized or otherwise processed (e.g. as described in U.S. Patent Publication No. 2003/0125808) to include an oxidized coating on, for example, the base metals. The coating preferably includes oxidized zirconium. In one embodiment, porous structure 110 is combined with an antifriction surface (examples of which are discussed herein), by for example, coating, infusing or encapsulating.

Sheets 200a–c may also be of any width (w), length (l) or thickness (not illustrated). In one embodiment, the thickness of the individual sheets range from approximately 0.001 to approximately one (1) inch; preferably from approximately 0.001 to 0.25 inches; more preferably from 0.005 to 0.060 inches. In one embodiment, the preferred thickness is determined by the type of cell or tissue growth desired. For bone ingrowth, for example, the preferred thickness of sheets 200a–c is between 100 to 450 microns. In one embodiment, sheets 200a–c have a thickness of approximately 0.012 inches and preferably 0.015 inches. Sheets 200a–c are preferably of a substantially uniform thickness though sheets 200a–c of varying thickness are within the scope of this invention. In one embodiment, the length and width of sheets 200a–c are limited only by the size of the environment into which it is placed (e.g., a bonding fixture). In one embodiment sheet 200 is a two inch square sheet of metal (e.g., titanium) which is 0.015 inches thick.

In one embodiment, porous structure 110 is formed from polymer sheets. In embodiments of the present invention when sheets 200 are formed of a polymer, aperture 202 may be directly laser machined, CNC drilled, die-cut, stamped, or injection or compression molded, water jet machined or otherwise formed.

In one embodiment, porous structure 110 is formed from ceramic or glass frits. In embodiments when sheets 200 are formed of ceramic or glass frits, apertures 202 may be machined by laser, abrasive jet machined, or fired as a compact or sintered mass to the net shape or pattern 206.

As shown in FIG. 2A, sheet 200a preferably contains at least one aperture 202 and more preferably a multiplicity of apertures 202. Aperture 202 is defined by web 204. In one embodiment, apertures 202 are 10 microns to 1000 microns wide, preferably 25 microns to 1000 microns wide and more preferably 100 microns to 450 microns wide (e.g., for some bone graft applications). In a preferred embodiment, there are a multiplicity of apertures 202 and webs 204.

In one embodiment, webs 204 and apertures 202 are configured in a predetermined pattern 206. In one embodiment, webs 204 define pattern 206. In one embodiment pattern 206 is a network of geometric shapes. The geometric shapes may be regular or irregular and may include one or more angular or curved portions. The geometric shapes may be pentagons, hexagons, squares, parallelograms, rectangles, circles, ovals or any other regular or irregular geometric shape. For example, in FIG. 2A, sheet 200a includes a tessellation of hexagons and pentagons assembled in a network. In one embodiment, the selection of pentagons and hexagons promotes a desired open pore structure such that when sheets 200a–c are stacked (discussed in more detail below), it is unlikely that two apertures will precisely align on all sides. In another embodiment, pattern 206 is random or pseudo-random. In still another embodiment pattern 206 is a chaotic or fractal pattern. Aperture 202 may be of any geometric shape and may include one or more curved, straight, undercut or beveled portions and combinations thereof.

Figure 2D:
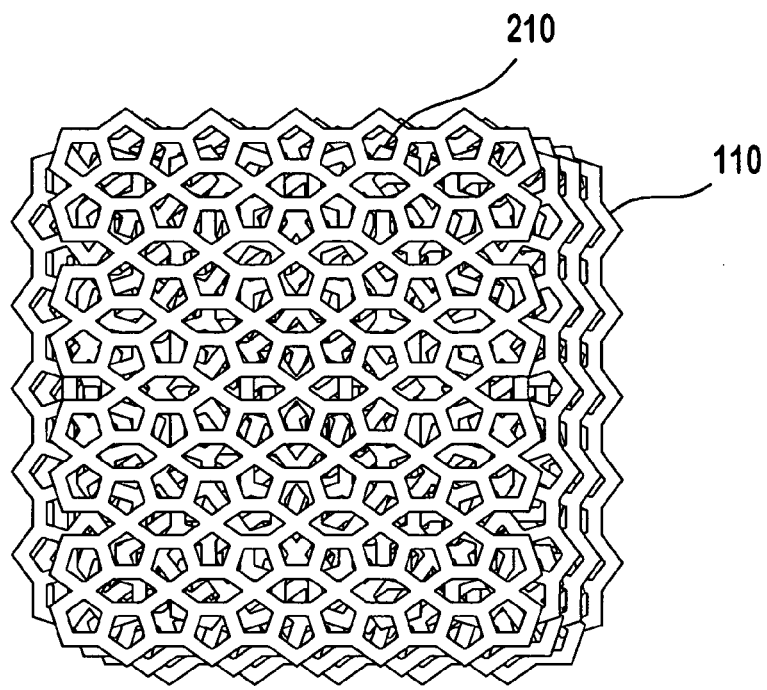
FIG. 2D is a top view of a porous structure formed from the porous sheets in FIGS. 2A–2C.
Figure 2E:
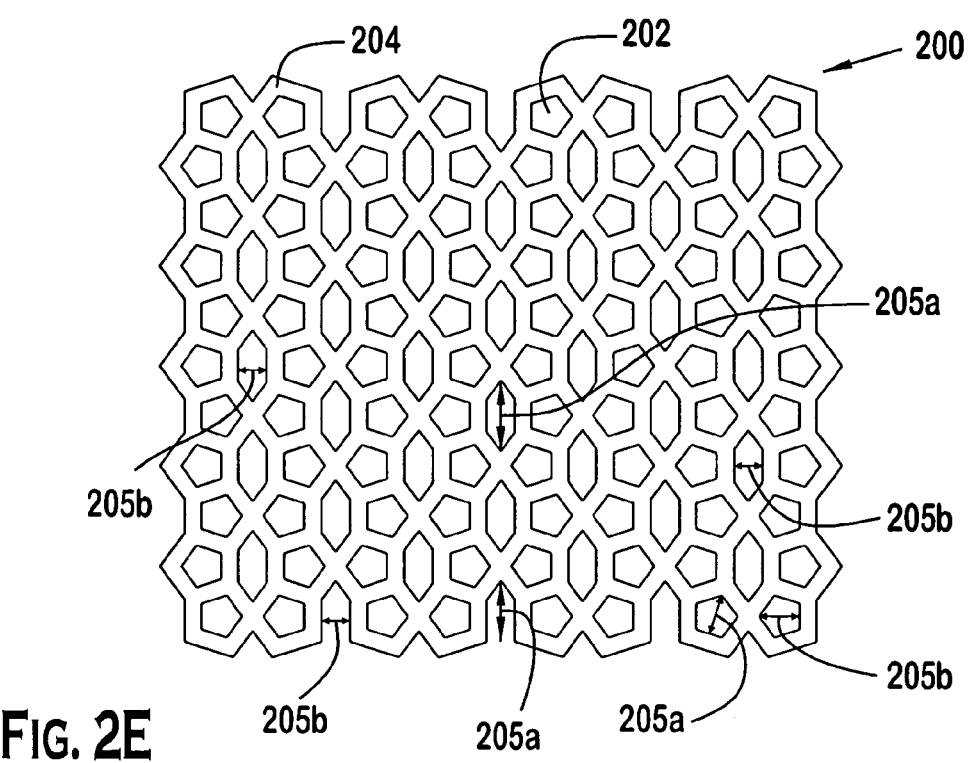
FIG. 2E shows a porous sheet according to the present invention.

In one embodiment, illustrated in FIG. 2E, webs 204 define apertures 202 having a longitudinal dimension 205a and a transverse dimension 205b. In one embodiment, longitudinal dimension 205a is different or equal to transverse dimension 205b. In one embodiment, longitudinal dimension 205a is up to 100 times or greater than the transverse dimension 205b. Preferably longitudinal dimension 205a is not greater than approximately four times the transverse dimension. In one embodiment, the transverse and longitudinal dimensions are between approximately 10 microns and approximately 5000 microns. Preferably the longitudinal dimension and transverse dimension are between approximately 100 microns and approximately 1000 microns and more preferably between approximately 100 microns and approximately 450 microns.

In one embodiment, sheets 200 are designed such that porous structure 110 is a biomimetic structure preferably mimicking the structure of tissue (e.g., bone). In one embodiment, sheet 200a–c and/or porous structure 110 is a hierarchical structure preferably resembling the hierarchical structures used in engineering to build rigid and lightweight solids. As an illustration one may consider a large complex structure that are preferably made of structural elements (e.g., three-dimensional pyramids or tetrahedrons) that are themselves made of structural elements (e.g., basic triangular structural elements).

In one embodiment, such structures are not scale-independently self-similar. In another embodiment, two-dimensional scale-independently self-similar structures (e.g., patterns) are stacked in a third dimension to produce a three-dimensional structure (e.g., porous structure 110). The Sierpinski Fractal is an example of a scale-independently self-similar object, which, when repeated or stacked into a third dimension, produces a series of hierarchical networks or hierarchical elements.

In one embodiment, aperture 202 perforates the entire thickness of sheet 200a. In another embodiment, aperture 202 partially perforates (i.e., does not penetrate through the entire thickness) sheet 200a. In one embodiment, sheet 200a contains various apertures 202 of a variety of penetration depths.

Figures 1, 6A:
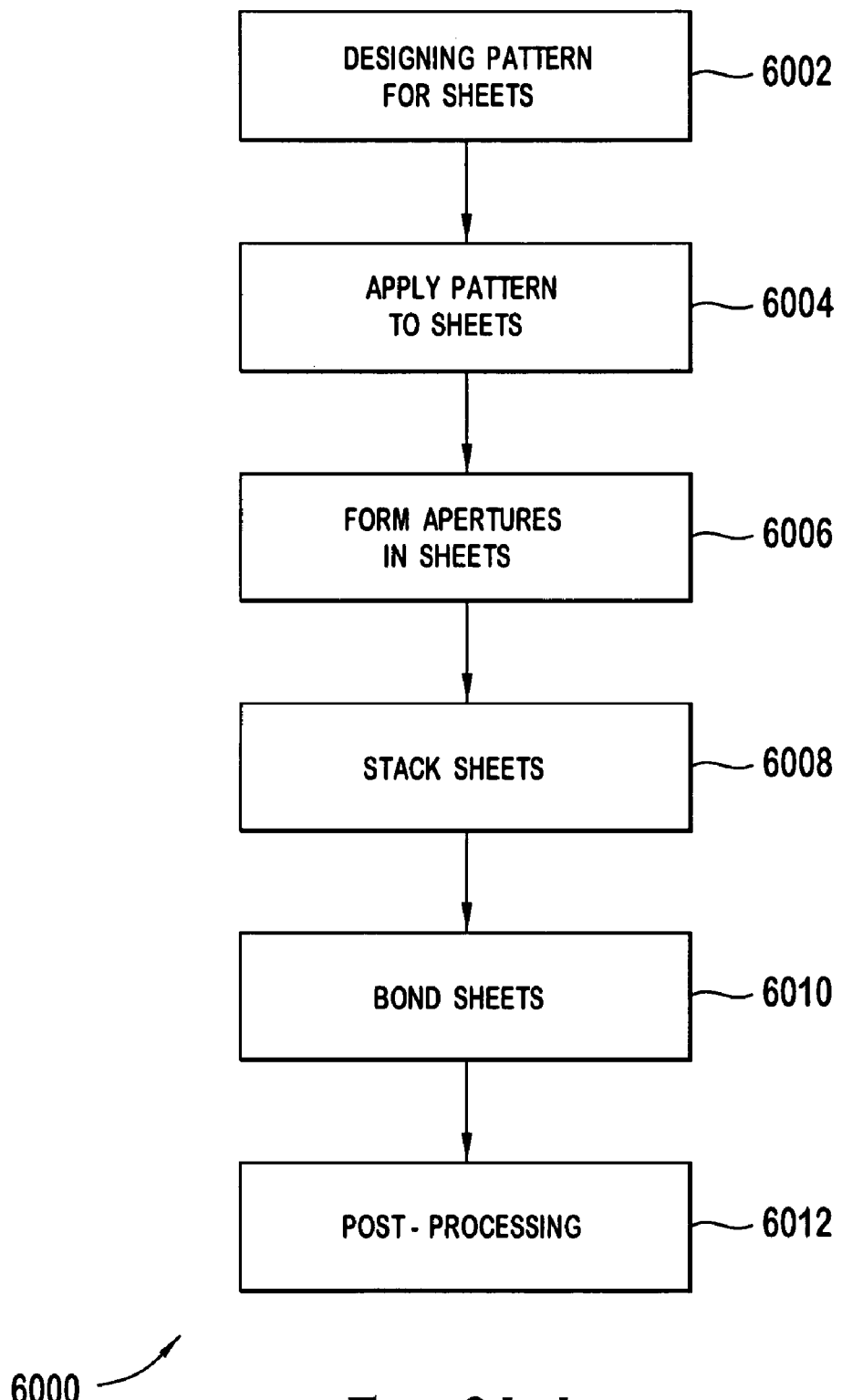

In one embodiment, (e.g., as illustrated in FIG. 3), sheet 200 has a first face 302 and a second face 304. In FIG. 3A, aperture 202 passes through sheet 200 such that passage 306 is extends from face 302 to face 304. In FIG. 3A, passage 306 include substantially straight walls 305a. In this embodiment, walls 305a in FIG. 3A also substantially perpendicular to faces 302 and 304. In one embodiment, walls 305a are at an angle that is obtuse or acute with respect to either face 302 or 304. Walls 305a, in one example, are a substantially a single surface (e.g., a single planar surface). In another embodiment, walls 305 have a plurality of surfaces. For example, in one embodiment, walls 305 are of intersecting planar surfaces (FIG. 3A-1).

In the embodiment illustrated in FIG. 3B, passage 306 include curved faces 305b. Curved faces 305b may be continuous from face 302 to face 304 or the may be discontinuous (e.g., having a point of inflection) as illustrated in FIG. 3B. The curved faces 305b illustrated in FIG. 3B have undercut portion 303. In one embodiment, curved face 305b include more than one undercut portion (e.g., at face 302 and at face 304).

In the embodiment illustrated in FIG. 3C, aperture 202 does not extend from face 302 to face 304. As illustrated in FIG. 3C, wall 305c may define an indentation 307 in one or both of the faces 302 or 304. Indentation 307 may have a curvilinear cross-section, a rectangular cross section, an undercut cross section, a cross section that combines a plurality of geometric shapes (e.g., curvilinear, undercut and rectangular), a cross section that is regular, irregular or any other geometric cross section.

In the embodiment in FIG. 3D, there are shown a plurality of indentations 307, some of which are intersecting one another. Indentations 307 preferably are oriented in varying spatial relation to one another. In one embodiment indentations 307 create mesas 308 at varying distances from face 302. This effect preferably is achieved with curved faces and/or straight faces 305a, 305b or 305c as shown in FIGS. 3A–3C. The faces can be oriented at any angle to the face into which indentation 307 is made.

By varying the shape of aperture 202, and by varying the face (e.g., 302 or 304) into which the indentation or aperture is made, one is able to specify a multitude of combinations of pores between and through adjacent sheets 200. Some of these combinations are illustrated below.

Figure 1A:
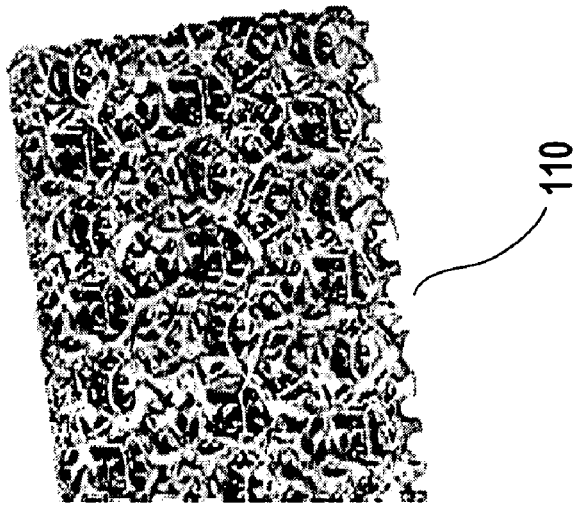
Figure 1C:
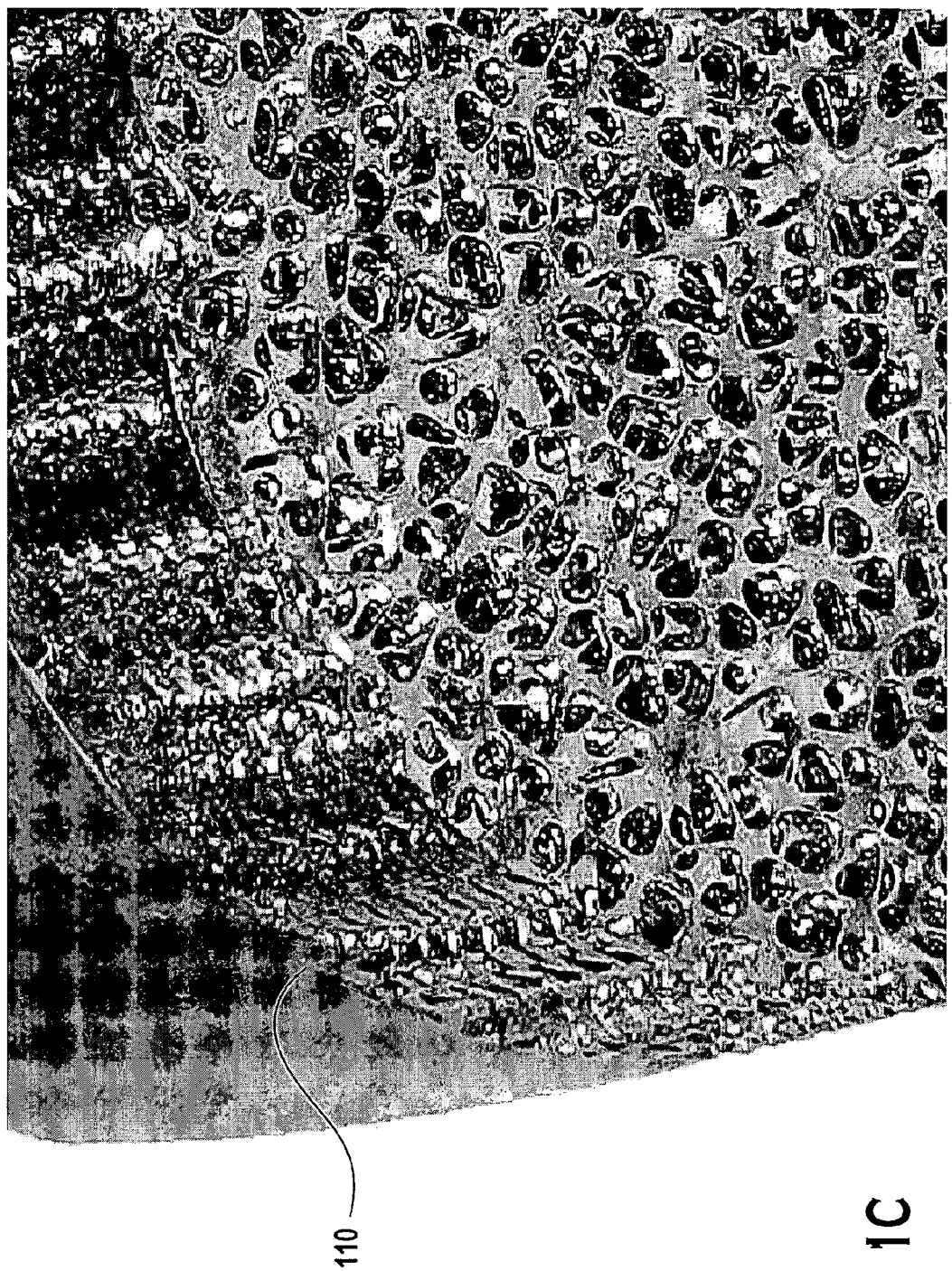
Figure 1E:
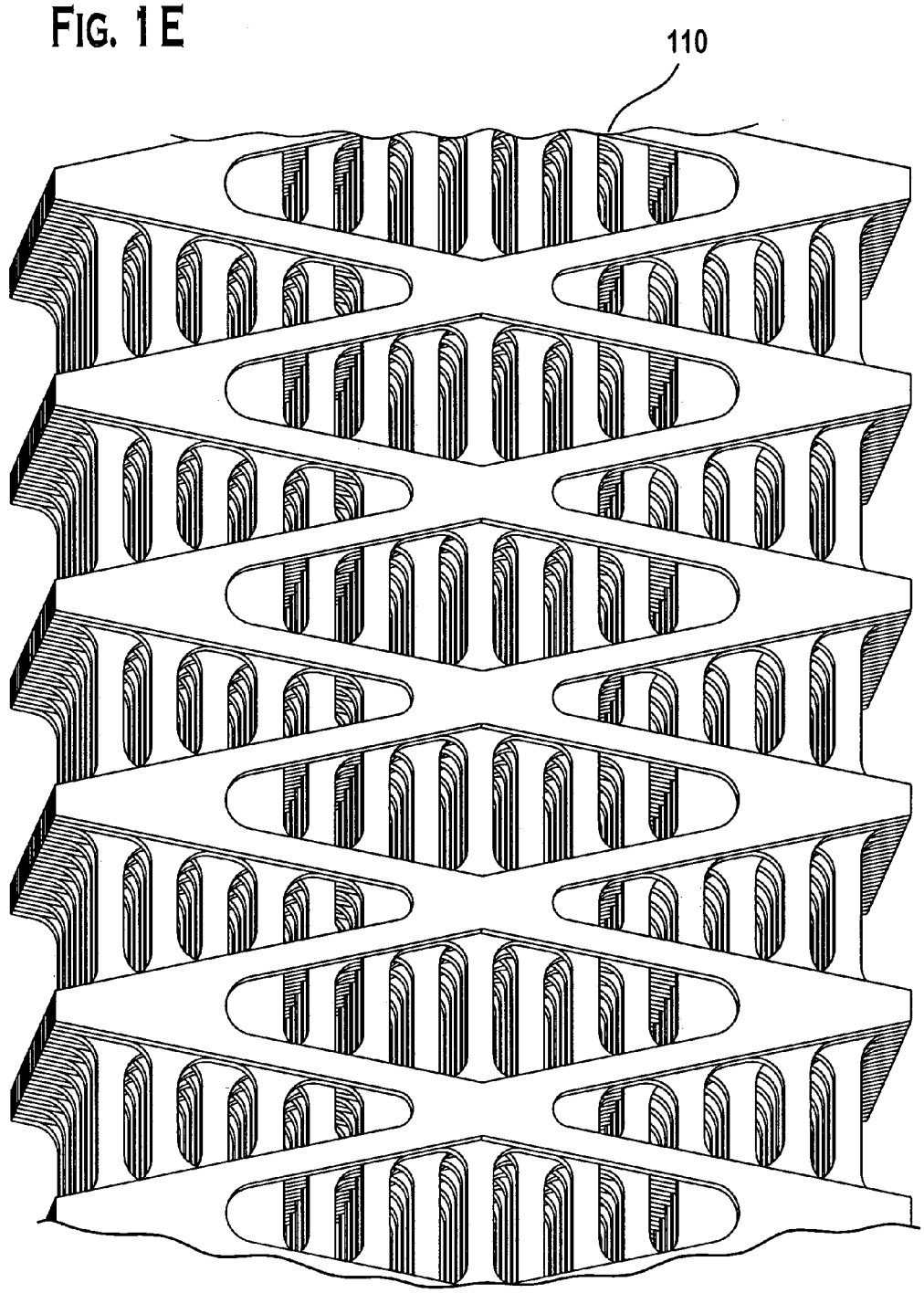
Figure 1G:
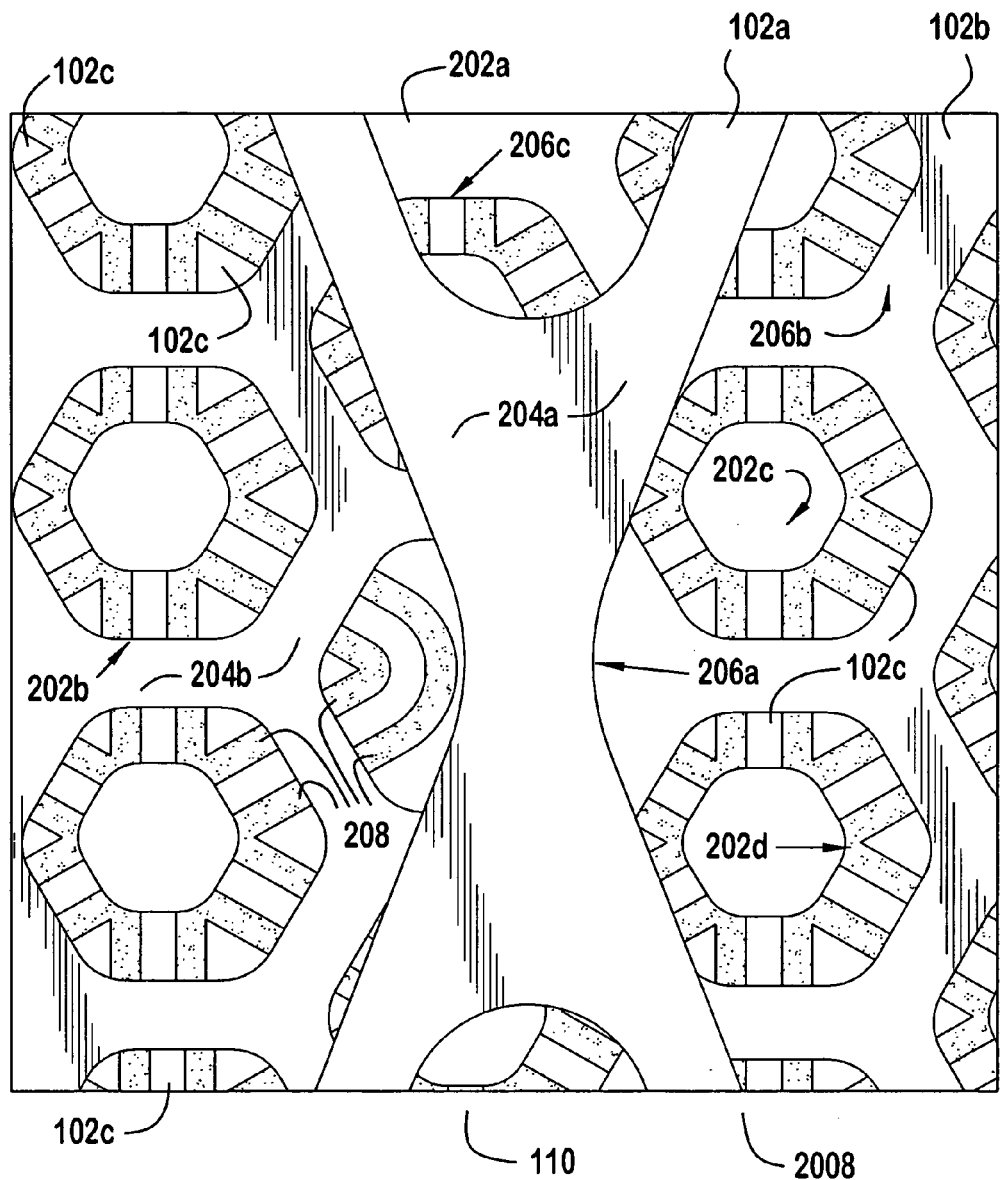

FIG. 1G, shows one embodiment of porous structure 110 formed from bonding two or more sheets together and having different patterns 206a, 206b, 206c with apertures 202 of varying depths. Top sheet 102a has a pattern 206a that is characterized by an X-shaped web 204a. In this embodiment, web 204a defines apertures 202a that perforate both sides of top sheet 102a. Second sheet 102b has a pattern 206b that is characterized by a web 204b that defines a plurality of hexagon apertures 202b. Second sheet 102b preferably is bonded to top sheet 102a and to a third sheet 102c as described herein. Third sheet 102c has pattern 206 including apertures 202c that perforate both sides of sheet 102c and apertures 202d that partially perforate sheet 102c. In one embodiment, partially perforating apertures 202d form a meandering channel 208 in sheet 202c that intersects apertures 202c. In one embodiment, sheets 102a, 102b, 102c form a sheet set 2008. In one embodiment, a plurality of sheet sets 2008 are bonded together as described herein to produce porous structure 110.

Preferred Methods for Producing Sheets 200

FIG. 6A-1 illustrates one exemplary method 6000 of producing porous structure 110. In step 6002, porous structure 110 is engineered at the sheet 200 level.

Figure 4:
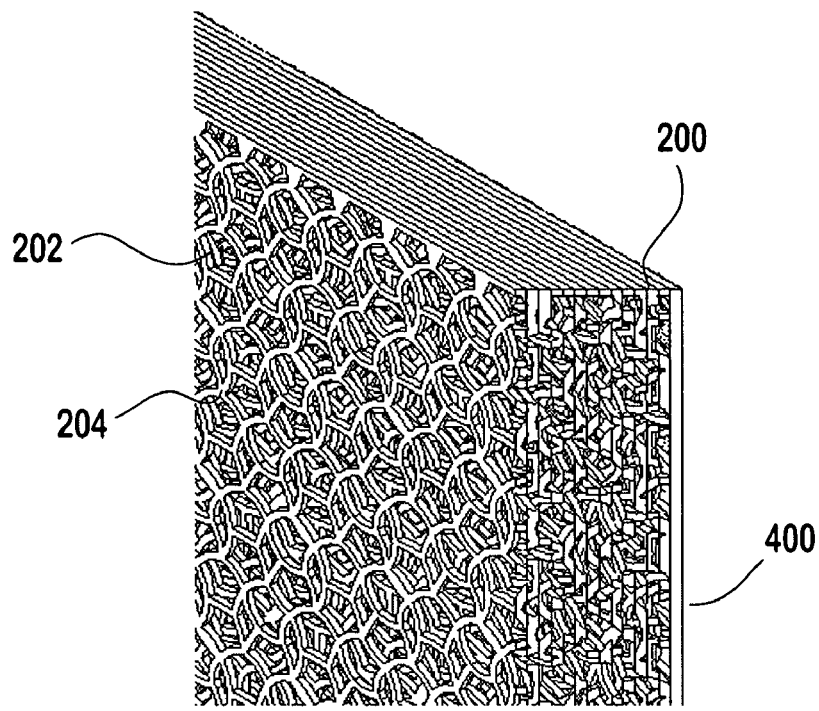
FIG. 4 shows a of a modeled stack of sheets according to the present invention.
Figure 5:
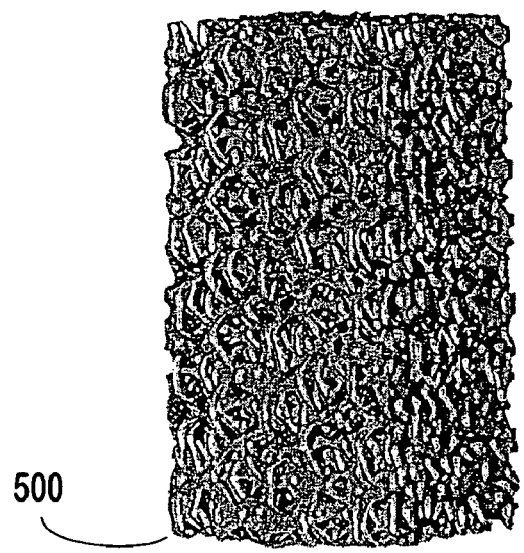
FIG. 5 shows a perspective view of an open pore structure having open pore regions and blank regions according to the present invention.

In one embodiment, a computer aided design file ("CAD file") is prepared of a candidate pattern for each sheet 200 that makes up porous structure 110. The "CAD file" may then be used to create pattern 206 in a predetermined configuration such as by any of the methods described herein. In one embodiment illustrated in FIG. 4, a model 400 of porous structure 110 is created. Model 400 was created using SolidWorks software and is embodied in an assembled structure 500 FIG. 5. Model 400 preferably is previewed and if necessary adjustments are made so as to achieve the desired resulting network. In one embodiment, the artwork including, for example, details of the tortuous path of pores within the porous structure 110 are modeled. In one embodiment of model 400, each of the apertures 202 and webs 204 on each sheet 200 are modeled.

In one embodiment, design optimization is achieved, by manipulating the order and/or orientation of sheets 200 and/or apertures 202 and/or webs 204 in Model 400. In one embodiment, the size and shape of apertures 202 and/or webs 204 in sheets 200 are modeled to achieve a desired porous structure 110. In one embodiment, the pattern 206 for each sheet is modeled in this fashion.

In step 6004, pattern 206 is applied to sheets 200. In one embodiment, a working photographic master film ("phototool") reflecting pattern 206 is prepared from a CAD file in any manner known to those knowledgeable in the field of photochemical etching. At least one face of sheet 200 preferably is covered with a maskant. Artwork associated with pattern 206 is then projected onto the sheet. In one embodiment, artwork is prepared on one or both sides of sheet 200.

In one embodiment, the artwork on one side of a sheet varies from the artwork on the other side of the sheet. In another embodiment, the artwork on each side of sheet is identical and/or in or out of register to produce the desired results.

After artwork has been applied, sheet 200 preferably is processed in accordance with known mechanical, chemical and/or electrical methods (e.g., photochemical machining) to achieve a desired structure (e.g., open pore lattice structure). In step 6006, apertures are formed in sheets 200. In one embodiment, step 6006 includes removing the maskant in accordance with known mechanical, electrical and/or chemical methods (e.g., laser ablation). Sheet 200 that conforms to pattern 206 preferably is thereby formed.

In one embodiment, aperture 202 is produced by a chemical, mechanical, electrical or any other process or combination of processes for creating apertures 202 (e.g., holes, perforations, indentations, channels, or slots) in a sheet or work piece. Apertures 202 may be produced by direct laser machining, abrasive water jet machining, stamping (e.g., computer numerical controlled (CNC) stamping), drilling, punching, ion beam etching, electrochemical etching, photochemical etching, electrical discharge machining (EDM), other perforation techniques and/or combinations thereof. In one embodiment, sheet 200 is produced by the methods disclosed in U.S. Pat. No. 6,620,332 to Amrich which is hereby incorporated by reference. In one embodiment, sheet 200 is produced by the methods disclosed in U.S. Pat. No. 6,599,322 to Amrich et al. which is hereby incorporated by reference. In one embodiment combinations of methods are used to create apertures in sheet 200.

In some embodiments, the method used for perforating sheet 200 may be specified to enhance the performance of a finished product. For example, in applications for which enhanced tissue in-growth is desired, individual sheets may be partially etched (e.g., half etched) with a pattern on one side of the sheet to provide an additional locking mechanism between the in-growing tissue and the open pore structure. In another embodiment, a feathered edge is etched into sheet 200 providing an enhanced locking mechanism for ingrown tissue. For example, perforated sheets formed from the process described in U.S. Pat. No. 6,599,322 which is hereby incorporated by reference, may be used to produce sheets 200 with a feathered edge. In one embodiment, such a method is used to create an effective outer surface of a medical device (e.g., implant). One such medical device preferably has an increased coefficient of friction that provides improved stability and fixation characteristics.

In one embodiment of step 6006, the forming of apertures in sheets includes treating sheets 200 including one or more pores, sheets 200 (e.g., of metal such as titanium) with a brief etch in nitric acid/hydrofluoric acid solution to remove surface storage, debris and handling oxidation.

In step 6008, sheets 200 with apertures 202 are stacked in a fixture. Different structures may be created by varying the configuration of stacked sheets 200. In one embodiment, sheets are stacked in sheet sets of one or more sheets each. An aspect of pattern 206 (e.g., thickness, geometry) in sheets 200 may be varied within or among sheet sets. In one embodiment a plurality of sheets 200 having a substantially similar pattern 206 may be stacked in substantially perfect register (see e.g., FIG. 1E) to form, for example, a first sheet set 208 (e.g., as shown in and described with respect to FIG. 6A-2) in which similar sheets 601a, 601b, 601c are aligned with one another. In one embodiment several sheet sets 208, each in substantially perfect register may be stacked to form a desired structure. In one embodiment one or more of the sheet sets 208 is aligned askew to one or more larger sheet sets. Multiple sheets sets 208 may be bonded to form porous structure 110.

In one embodiment of porous structure 110, each sheet 200 within a particular sheet set 208 has a substantially similar pattern of webs 204 and apertures 202. In another embodiment of porous structure 110, each sheet set 208 has sheets 200 having a substantially different pattern of webs 204 and apertures 202. In one embodiment the sheet pattern variations differ between sheet sets 208 that are used to form porous structure 110.

One may also achieve varying results by varying the aperture-to-web ratio of the individual sheets 200, for example, within sheet sets 208. The aperture-to-web ratio is the volumetric ratio of aperture volume to web volume for an individual sheet. In a preferred embodiment, aperture-to-web volume of sheets 200 ranges from 95:1 to 1:20. Aperture-to-web ratios may be varied, for example, by adjusting the artwork and etch procedures to produce sheets 200 of varying porosity, such as by creating sheets 200 with more or fewer complete or partial apertures 202.

Figures 2, 6A:
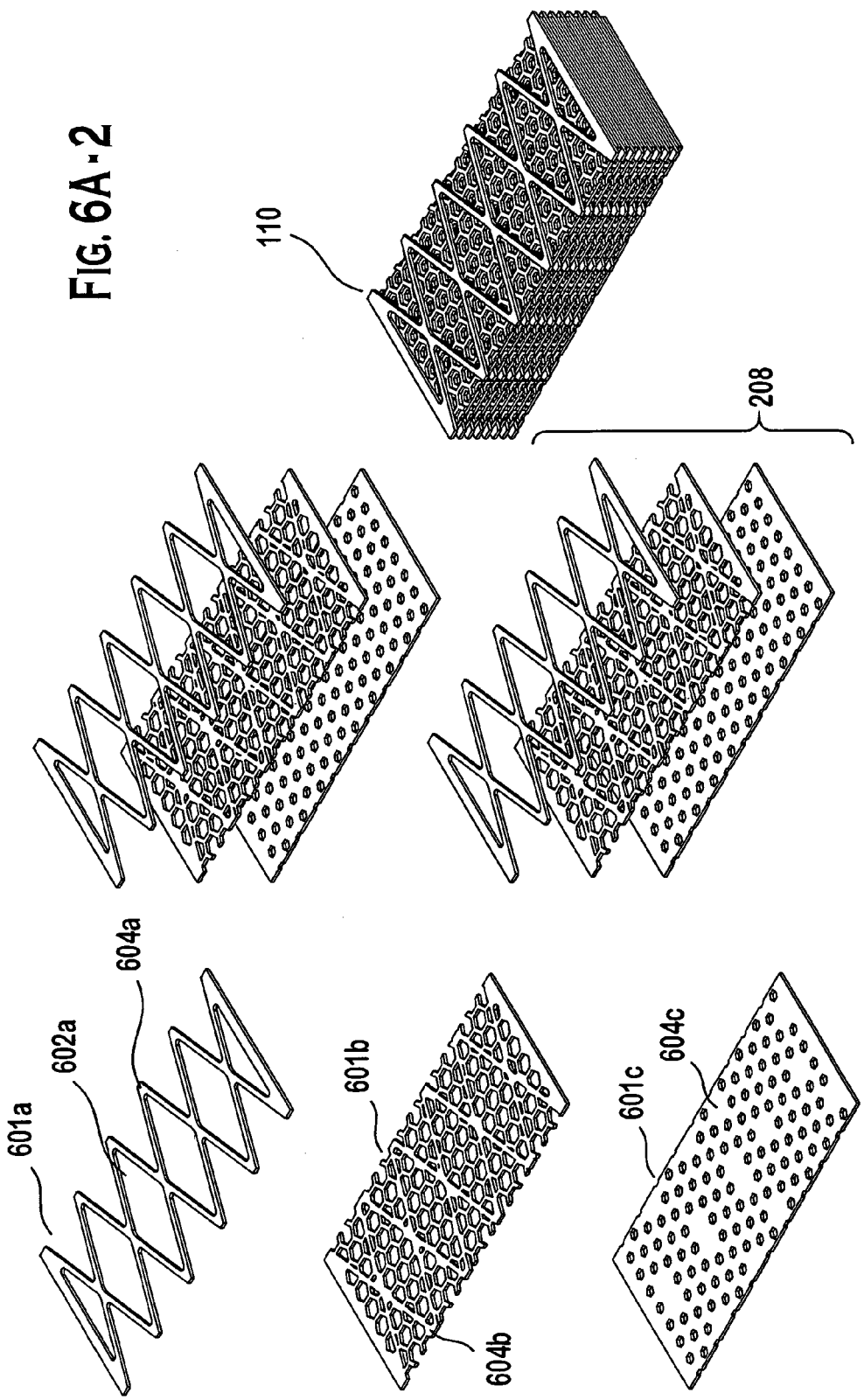

One embodiment of step 6008 is illustrated in FIG. 2D. In FIG. 2D, sheets 200a, 200b and 200c are stacked on top of one another in a desired orientation to form a sheet set 208. The number of individual sheets (e.g., 200a–c) in sheet set 208 may vary from as few as two sheets 200 to as many sheets 200 as necessary to achieve the desired finish product. In one embodiment, as illustrated in FIG. 2, sheets 200 preferably are stacked in a skewed alignment and orientation. Sheet sets 208 can include any number of desired sheets. Sheet sets 208 can be bonded to one another as described herein to form repeating patters of sheet sets.

FIGS. 2A–C illustrates an exemplary skewed alignment wherein sheets 200a through 200c were formed from predetermined artwork as described herein. In one embodiment, sheet 200b is aligned at an angle θ to sheet 200a. Angle θ may be any angle between 0° and 360°. FIGS. 2A–C further illustrate an embodiment wherein each three sheets (e.g., sheet set 208 in FIG. 6A-2) are in skewed alignment to each other. In one embodiment, illustrated in FIG. 2A–2D, three substantially identical sheets are stacked such that each sheet is skewed at an angle to its adjacent sheet. The assembled stack then preferably is shifted in both axes so that its cross section is in the shape of a 10 degree lozenge.

FIG. 6A-2 illustrates a sheet set 208 that includes three sheets 601a, 601b, and 601c with varying patterns. Sheet 601a has a pattern of webs 604a configured to form an open lattice structure. Webs 604a form a crossing pattern that further defines apertures 602a. Sheet 601b has a pattern of webs 604b configured to form a lattice that has a aperture-to-web ratio that is greater than the aperture-to-web of sheet 601a. The pattern of webs 604b on sheet 601b aligns with the webs 604a of sheet 601a such that when the sheets are bonded as described herein, there will be formed a continuous structural member formed between web 604a and web 604b. Sheet 601c has a pattern of webs 604c configured to form a lattice that has an aperture-to-web ratio that is greater than the aperture-to-web ratio of sheet 601c. The pattern of webs 604c on sheet 601c aligns with the webs 604a and 604b such that when sheets 601a, 601b and 601c are bonded together, there is formed a porous structural member formed between web 604a, 604b and 604c.

Figure 6B:
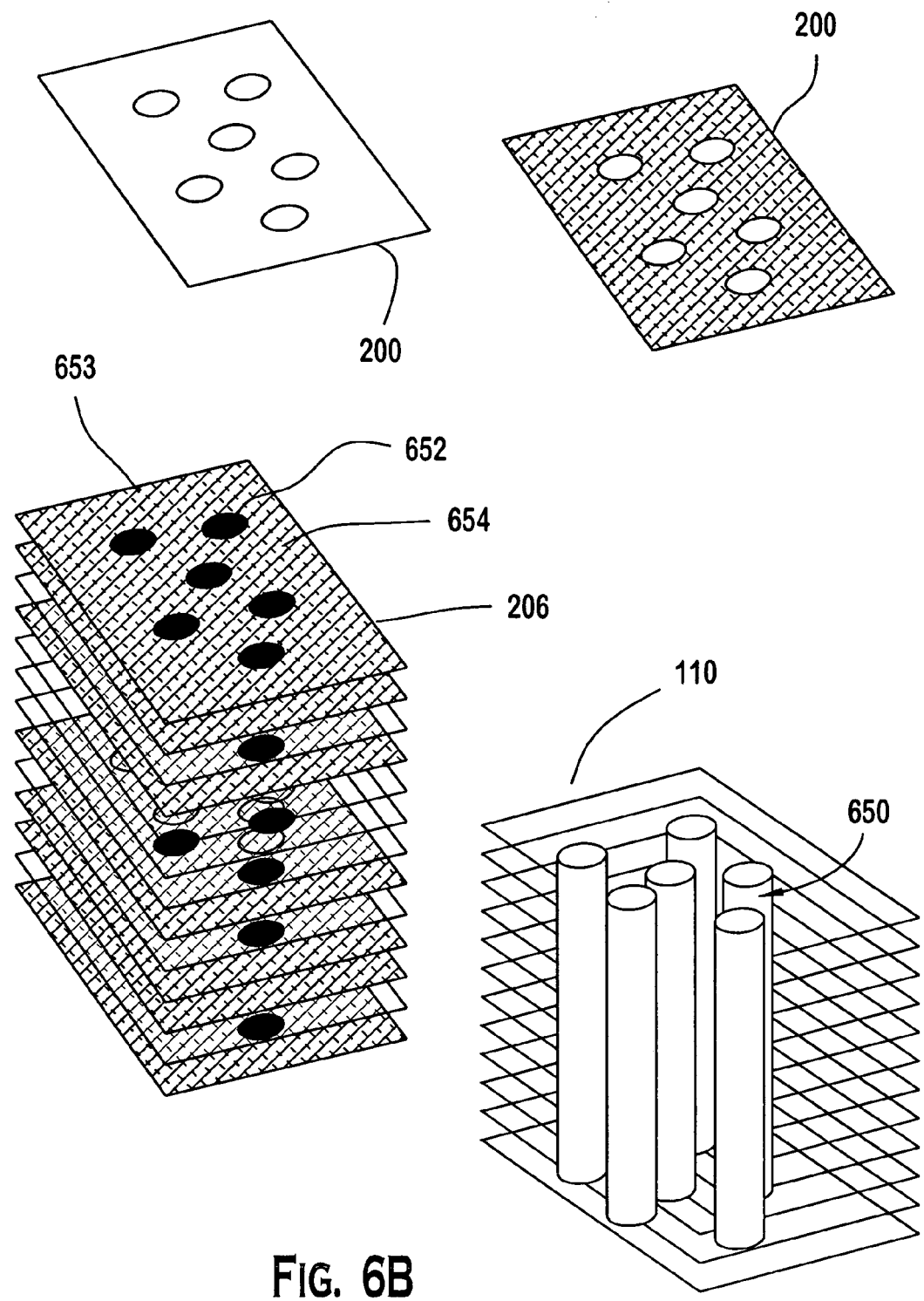
FIG. 6B shows one embodiment of open pore sheets, and an open pore structure according to the present invention.

In one embodiment, sheets 200 and sheet sets 208 are stacked to achieve structural objectives. In one embodiment, porous structure 110 is engineered to satisfy a particular structural or physical properties (e.g., modulus of elasticity) of the desired finished product. A finite element analysis is preferably performed to derive a pattern 206 (e.g., a two-dimensional pattern) for sheets 200. Each sheet preferably reflects a particular engineered pattern that when assembled (e.g., bonded as described herein), will create for porous structure 110a desired structural quality and/or feature(s) (e.g., a specified modulus of elasticity). For example, FIG. 6B illustrates porous structure 110 (both before and after assembly) with integral stiffening members 650. Pattern 206 is a regular pattern of solid regions 652 webs 653 and apertures 654. FIG. 6B illustrates and embodiment wherein solid regions 652 are aligned to create a desired pattern of connected stiffening members 650. In another embodiment, solid regions 652 may be purposefully misaligned to achieve a different effect. In some embodiments, solid regions 652 align to form abrupt or gradual transition from the foam-like structure to stiffening members 650. In one embodiment, the resulting stiffening members 650 form solid pillars penetrating and/or protruding through the porous structure 110. Integral stiffening members 650 preferably are strong enough to withstand the temperature and pressure of a second bonding (e.g., diffusion bonding) process to another material. As with entirety of porous structure 110, stiffening members 650 can also be machined (e.g., conventional tapping operation, cold working, machining) as illustrated in FIGS. 1F1 and 1F2. Engineered features also include regions of interconnected and/or non-connected apertures 202. In one embodiment, engineered regions of unconnected apertures of various porosity are defined within porous structure 110. In one embodiment, alignment of features (e.g., stiffening members, struts, apertures, pores) from sheet to sheet form three-dimensional features throughout porous structure 110.

In one embodiment, sheets 200 and/or sheet sets 208 are stacked to achieve porosity objectives. For example, in one embodiment, it is desirable to create porous structure 110 with a porosity that varies throughout the three dimensional structure. Such a porous structure 110 is useful, for example, to facilitate both hard tissue (e.g., bone) ingrowth and soft tissue (ligament) ingrowth into different ends of the same structural member.

Figure 7A:
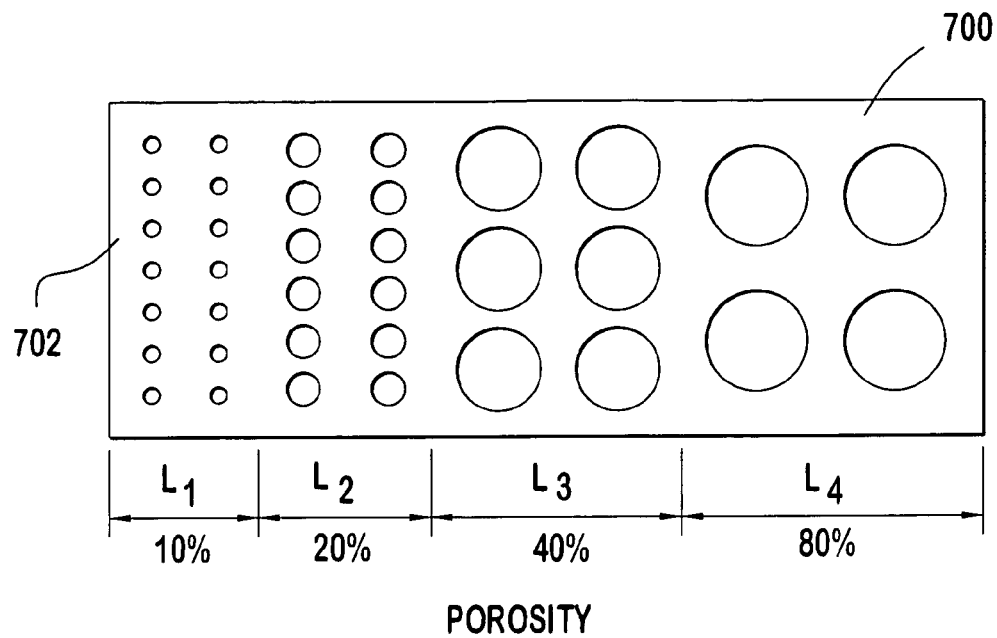
FIG. 7A–B shows a porous structure of the present invention.

For example, FIG. 7A illustrates examples of porous structure 110 having a differential porosity. FIG. 7A illustrates a stepped differential porosity wherein regions of porous structure 700 representing different porosity are formed in the structure. In FIG. 7A regions of lower porosity L1 (10%) are formed on a first end 702. In one embodiment, lower porosity region L1 (10%) is followed by a higher porosity region L2 (20%) which may or may not be the same length as L1 (10%). In one embodiment, the porosity of structure 700 increases in a stepped pattern across structure 700. In one embodiment, regions of high porosity are separated by regions of lower porosity. In one embodiment, regions of lower porosity act as barriers to certain types of material (e.g., polymer) while allowing certain other types of materials to pass (e.g., air). In one embodiment, regions of differential porosity are interconnected (e.g., interconnected apertures within one region such as L1 and/or interconnected pores between regions such as between L1 and L2). In another embodiment, regions of differential porosity are not interconnected (e.g., neither the apertures within a particular region such as L1 or between regions (e.g., between L1 and L2) are interconnected). Combinations of interconnected and non-interconnected aperture are also within the scope of the present invention. Dimensions of apertures 202 may vary within a single sheet or from sheet to sheet to create porous regions across any one sheet or region or across more than one sheet or region.

Figure 7B:
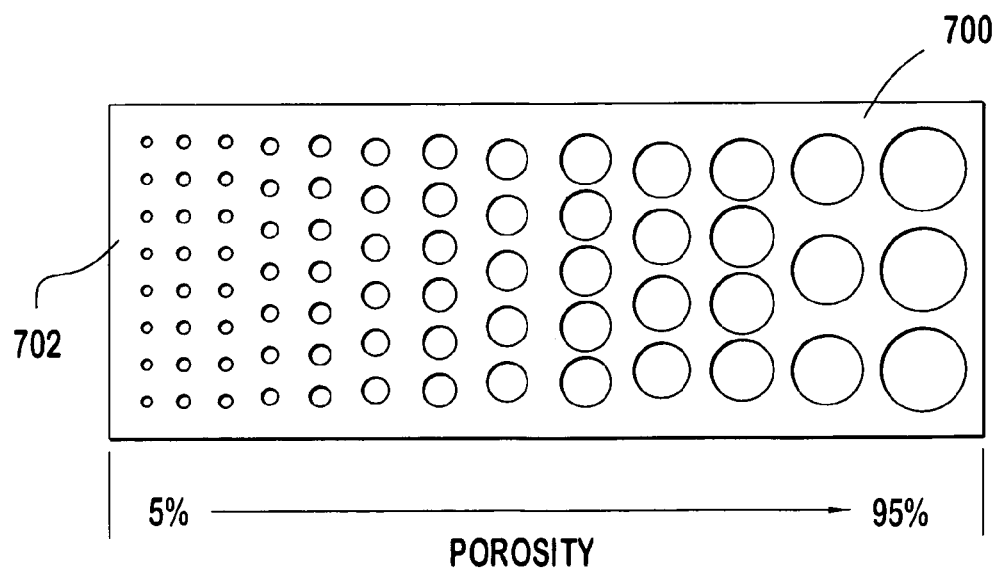

In FIG. 7B there is illustrated a graduated porosity wherein the porosity varies from one end of porous structure 700 to another end of porous structure 700. The change in porosity however is more gradual than the change of porosity illustrated in FIG. 7A. Porosity of porous structure 110 may vary from sheet 200 to sheet 200, sheet set 208 to sheet set 208 or across any one particular sheet 200 or sheet set 208.

Bonding Sheets

In step 6010, sheets 200 and/or sheet sets 208 are bonded together. In one embodiment, at least a portion of web 204 of a first sheet 200 is bonded (e.g., by the methods disclosed herein) to at least of portion of web 204 of each adjacent sheet 200 or sheet set 208. In a preferred embodiment, portions of adjacent webs 204 form solid bonded intersections between the sheets 200.

Sheets 200 and/or sheet sets 208 can be bonded by any method of bonding, including but not limited to vacuum diffusion bonding, chemical bonding (e.g., by reactive species such as epoxies, urethanes, and other appropriate adhesives), physical bonding, explosive bonding and mechanical bonding. In preferred embodiments, sheets 200 and/or sheet sets 208 are laminated, vacuum-diffusion bonded and/or adhesive bonded. Other examples of bonding methods include hot isostatic bonding (HIP), cold isostatic bonding (CIP), brazing, gluing, adhesion, soldering, resistance welding, induction welding, solvent bonding, thermal or ultrasonic welding, mechanical interlocking, staking, swaging, riveting, deformation, suturing and pinning. In ceramic applications bonding preferably is accomplished by firing a ceramic or glass frit.

Figure 7C:
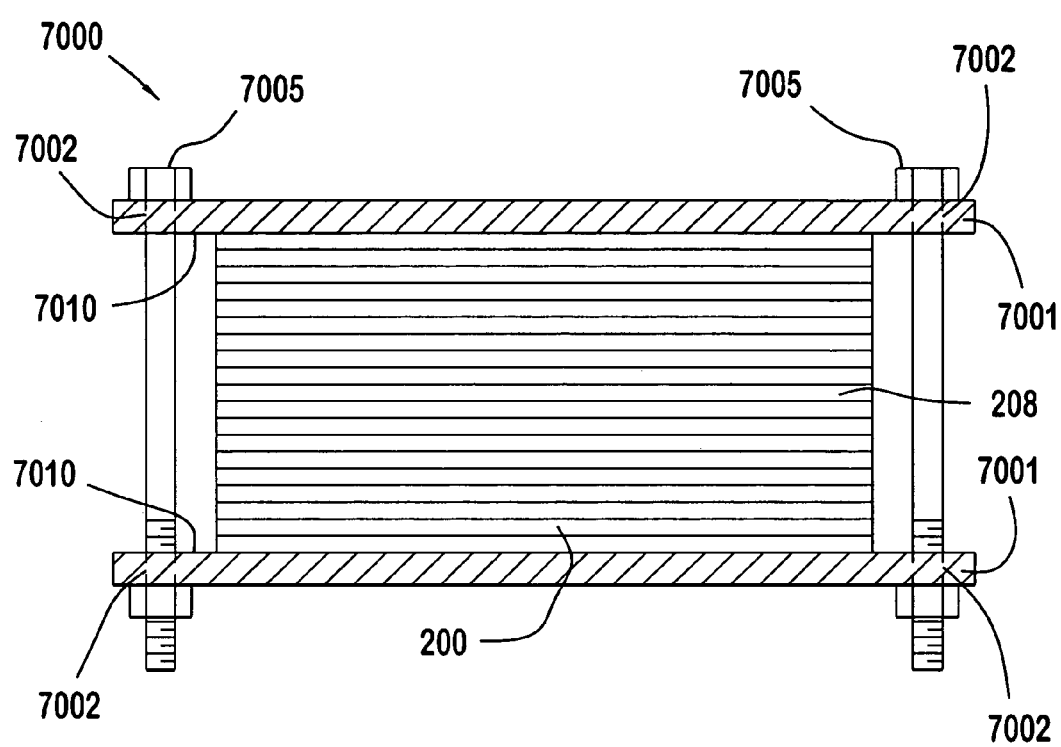
FIG. 7C shows one embodiment of a fixture for manufacturing the porous structure of the present invention.

In one embodiment using vacuum diffusion bonding, sheets 200 and/or sheet set 208 is mechanically compressed with, for example, a bonding fixture (e.g., clamp). In one embodiment (FIG. 7C), the bonding fixture 7000 includes two stainless steel plates 7001 (e.g., ¾ inch thick type 304 stainless steel plates) with a hole 7002 near each corner. Bolts 7005 (e.g., $\frac{5}{16}$–18 molybdenum bolts) were then tightened sequentially from opposite corner to opposite corner to a sufficient torque to achieve a compression (e.g., compressions force of 0.002–0.004 inches), or a theoretical thread displacement (e.g., about 0.0138) achieved by tightening each bolt one quarter-turn after contact. In one embodiment, the bolts preferably are elastically tensioned.

In one embodiment, to prevent sticking and galling, the fixture surfaces 7010 in contact with a sheet set 208 (e.g., comprising titanium etched foil sheets) are coated with a thin layer of magnesium hydroxide, boron nitride, graphite or any appropriate high temperature lubricant. The molybdenum bolt threads are preferably coated with boron nitride dispersion. In one embodiment, it has further been found that when the bonded part is removed, it slides easily from the fixture, because the bonding process reduces the thickness of sheet set 208 by approximately 0.020" per ½ inch thickness.

The compressed sheet set 208 may then be placed in a high temperature, high vacuum fixture (e.g., a programmable AVS vacuum furnace) to produce the desired vacuum diffusion bonding. In one embodiment vacuum pressure of approximately $10^{-3}$ atm is used in combination with temperatures of approximately 800° F. to approximately 1250° F. In one embodiment, an AVS Ace 4-1280 controller and software is programmed to raise the temperature of the assembly to 850° C. and maintain the temperature for one hour followed by a helium cool-down. In another embodiment, the temperature of the assembly is raised to 900° C. and maintained for four (4) hours followed by a helium cool-down.

During the heating cycle, the higher coefficient of thermal expansion of the stainless steel compared to the lower expansion coefficient of the molybdenum bolts preferably adds still more pressure loading onto the assembled stack. Thus, when the secured sheets 200 and/or sheet sets 208 are exposed to heat, the stainless steel expands to a greater extent that the molybdenum bolts. As a result the pressure on the stack of sheets 200 increases and the bond between sheets 200 can be achieved at a lower temperature. The lower temperature is desirable because it prevents or reduces or minimizes grain growth in the materials used to form porous structure 110, which reduces the strength of the metal. Also, a more rapid process cycle results thereby allowing more inexpensive production of the porous structure 110. The close intimate contact of the metal surfaces generated by the compression, furthermore, allows more complete and rapid bonding.

Upon removal of the cooled assembly of sheets 200, the assembled porous structure 110 (resembling a "foam") is completely bonded, layer-to-layer with diffusion bonds having a strength that preferably is substantially identical to that of the parent metal. In destructive bend testing performed in a press with a total pressure of 1,800 Pounds applied to a ½ inch diameter dowel caused a 50% "U"-shaped deformation of the part and resulted in no bond failures.

In another embodiment, bonding is achieved using, for example, aluminum metal as a brazing intermediate for certain alloys, including 6-Al 4-V Titanium alloy. In one embodiment, a thin sheet of aluminum foil can be laminated between each sheet 200. When the assembly is compressed, and placed into a vacuum furnace, the aluminum melts and flows at a substantially lower temperature than is needed to diffusion bond titanium and its alloys. In regions of titanium-to-titanium contact or near contact, an aluminum/titanium eutectic alloy is formed. In one embodiment, some aluminum is free to diffuse into the 6-4 titanium. Preferably, the lower temperatures needed for this process minimize grain growth problems frequently seen in titanium alloys when heated near its melting point for long periods.

Alternatively, aluminum "flake" ("Paintmakers' Powder") is dusted onto the titanium lattice sheets so as to minimize excess aluminum in the system. While aluminum is objectionable in implant applications, the use of aluminum in applications such as aerospace applications may be preferred.

In one embodiment, sheets 200 and/or sheet sets 208 are bonded by explosive bonding. Explosive bonding is considered a solid state welding process that uses controlled explosive energy to force two or more metals together at high pressures. The resultant composite system is joined with a high quality metallurgical bond. The time duration involved in the explosive welding event is so short, that the reaction zone between the constituent metals is microscopic. In one embodiment plates are accelerated into one another with the forces generated by an explosive detonation. In one embodiment, a sheet of metal or other material (e.g., a "Flyer plate") is propelled by an explosion toward a stationary plate or a stack of stationary plates to be joined. The Flyer plate thus yields to the force of the explosion as the detonation front moves across the surface of the plate. Kinetic energy is thereby transferred into the stationary plates as the forces at the collision point cause the first few molecular layers to liquefy. Plasma jets between the surfaces as the collision point accelerates across the plates thereby creating a full metallurgical weld. Explosive metal bonding is considered a cold joining process because the materials remain at or near ambient temperature and retain their original characteristics. Explosive bonding is performed, for example, by High Energy Metals, Inc. of Sequim Washington.

Explosive bonding experiments were conducted with samples of zirconium, titanium, and cobalt/chromium alloy sheets 200. All combinations of these materials were successfully bonded using explosive bonding. In a first series of tests, a niobium interlayer was placed between the two metals to be bonded. A niobium layers is used, in one embodiment, when metals are to be heated at a later stage. The niobium interlayer can prevent eutectic formation between the principle metals to be bonded. Metals were also successfully explosion bonded without a niobium interlayer.

In one embodiment, adjoining sheets 200 and/or sheet sets 208 are bonded with interlocking tongue and groove joints. In one embodiment, adjoining sheets 200 and/or sheet sets 208 are bonded together with a combination of two or more bonding techniques. In one embodiment, for example, the interlocking tongue and groove joints are combined with another bonding technique (e.g., diffusion bonding, explosion bonding) described herein. In one embodiment, layers of different materials are bonded together by combining two or more bonding techniques such that the strength of the bond formed is determined by a combination of two or more of the bonding techniques.

Figure 7D:
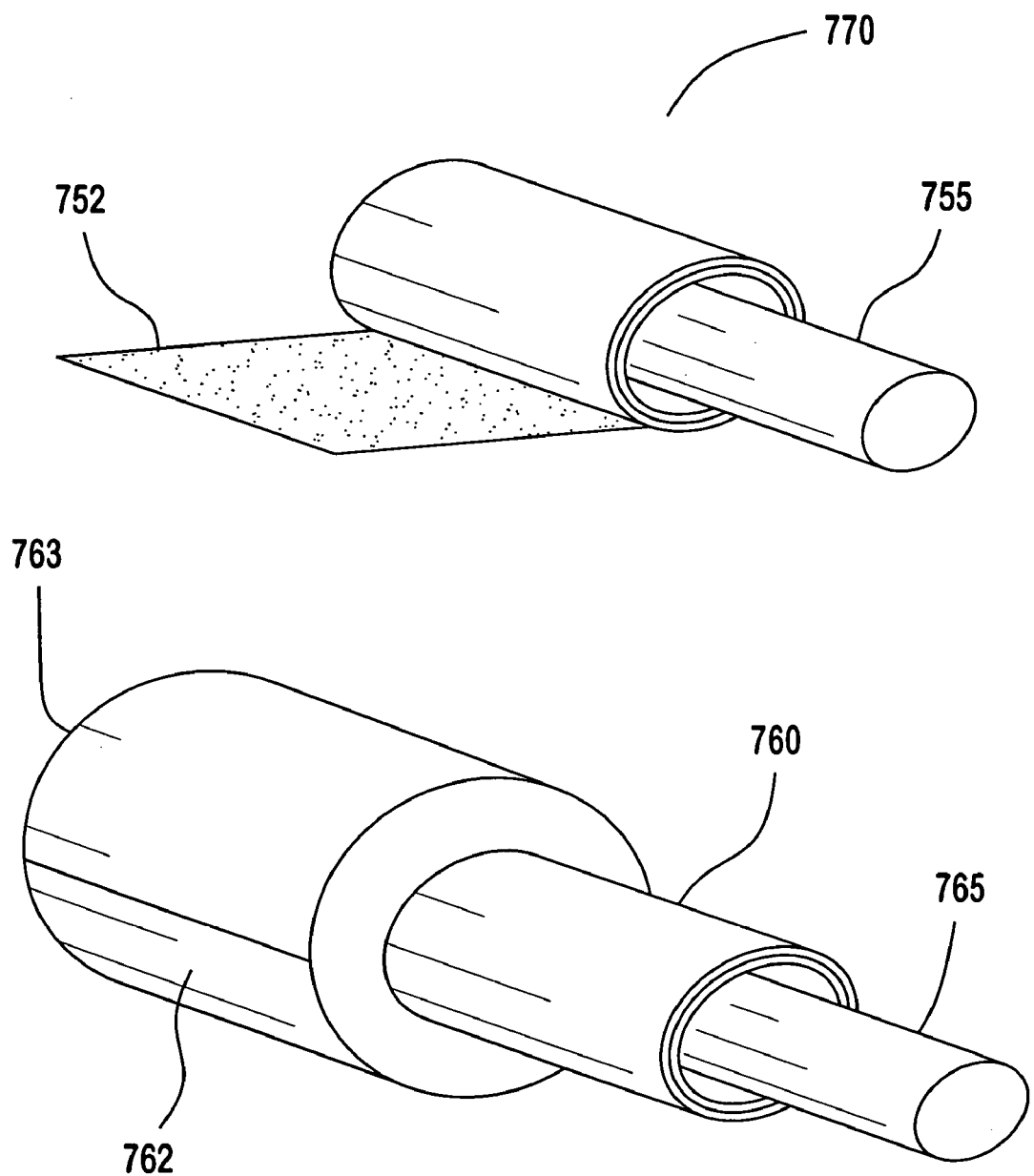
FIG. 7D shows one embodiment of a fixture for manufacturing the porous structure of the present invention.

The bonding process described herein is not intended to limit the geometry of porous structure 110. Sheets 200 having any geometry or three dimensional profile (e.g., curved, flat, serpentine, wave-like) are bonded together. In one embodiment, sheets are preformed in a shape configured to connect to a solid material (e.g., the a solid medical implant or component of a medical implant) and are bonded together in that configuration. In one embodiment, illustrated in FIG. 7D, porous structure 110 may be formed in a cylindrical geometry. In one embodiment, there is fixture 770 having a an expandable mandrel 755 and a cylinder 762. In one embodiment, fixture 770 is a mold within which assembled sheets are stacked for bonding. Porous structure 110, in one embodiment, is assembled by rolling perforated sheets 752 onto mandrel 755. Preferably sheets 752 are tightly rolled onto mandrel 755 to form rolled assembly 760. In one embodiment, rolled assembly 760 is pressed into cylinder 762 which preferably has outer sleeve 763. In one embodiment, mandrel 755 and cylinder 762 are of materials with differing coefficients of thermal expansion such that when the fixture is heated, mandrel 755 expands to a greater degree than cylinder 762 and outer sleeve 763 thus creating the pressure necessary to bond together perforated sheets 752. In one embodiment, mandrel 755 preferably is stainless steel while cylinder 762 and outer sleeve 763 are molybdenum. In one embodiment, mandrel 755 has cladding 765. Cladding 765 may be any material that is selected to prevent a bonding formation (e.g., the formation of a eutectic) between the between mandrel 755 and rolled sheets 752. Cladding 765 may be any material that prevent mandrel 755 from sticking to rolled sheets 752. Thus, for example, cladding 765 may be tantalum, niobium or molybdenum. Preferably, cladding 765 is graphic or boron nitride. In one embodiment, the material for cladding 765 is selected to prevent eutectic formation and/or dissolution with titanium sheets 752. In one embodiment, either or both of mandrel 755 and cylinder 762 are constructed of porous material (e.g., porous material 110).

In one embodiment, after the bonding cycle is complete, mandrel 755 is pressed or machined out. In one embodiment, cylinder 762 is parted longitudinally to removed bonded porous structure 110.

Post Processing

In step 6012 porous structure 110 is post-processed. In one embodiment, porous structure 110 may be post processed by any chemical, mechanical or electrical process after porous structure 10 is formed (e.g., bonded). In one embodiment, an etching step may be performed on the bonded stack of lattice sheets 200 forming porous structure 110. In one embodiment, this etching step increases the pore volume of the structure 110.

In one embodiment it is desirable to remove stepping artifacts (e.g., resulting from an etching process) from the joints of individual layers (e.g., sheets 200) in a sheet stack 208. Stepping artifacts may be removed by, for example, a post-processing machining method. FIG. 1A shows porous structure 110 prior to post-processing. In one embodiment, bonding of sheets 200 produces inside corners that are not razor sharp but show evidence of material flow. These small meniscuses preferably are removed by post-processing (e.g., a post-etching step). In one embodiment, the post-processing produces smooth surfaces within the structure. In one embodiment, the post-processing results in an adjustment of the pore-to-web ratio. Post processing may preferably also include mechanical working such as shot peening, and machining.

In one embodiment, post-processing of porous structure 110 includes oxidation of porous structure 110. In one embodiment, porous structure 110 is constructed at least in part from zirconium or zirconium alloy sheets 200. After post processing, porous structure 110 preferably already includes or is further processed to include an oxidized zirconium surface. The oxidation step may be performed as described in U.S. Pat. No. 6,652,586 or U.S. patent application Ser. No. 10/313,205 (Publication No. 2003/0125808) each of which are hereby incorporated by reference.

In another embodiment, one or more polymers are infused or otherwise caused to migrate throughout at least a portion of the open pore structure of porous structure 110 according to the present invention. Polymers such as ultra high molecular weight polyethylene (UHMWPE), polytetrafluoroethylene (PTFE), high density polyethylene and hydroxyapetite are among those polymers that will find utility in the present invention. Other useful polymers include polyether ether ketone (PEEK), polyglycolic acid, polylactic acid, polyoxyethylenes and similar materials. Preferred polymers include nylons, urethanes, silicone elastomers, some epoxies (e.g., sufficiently hydrolytically stable polymers such as those used in pacemaker domes), PEEK polyacetals, polyesters and other such recognized polymers. In one embodiment, the polymer is selected for characteristics such as wear-resistance, coefficient of friction and chemical inertness and combinations thereof. One method of infusing polymer through porous structure 110 is by compression molding. By infusing polymer into porous structure 110, the complexity of the structure enhances the bond between the polymer and the structure. In one embodiment, porous structure 110 is substituted for the open-celled lattice described in U.S. Pat. No. 6,087,553 which is hereby incorporated by reference.

Figure 13A:
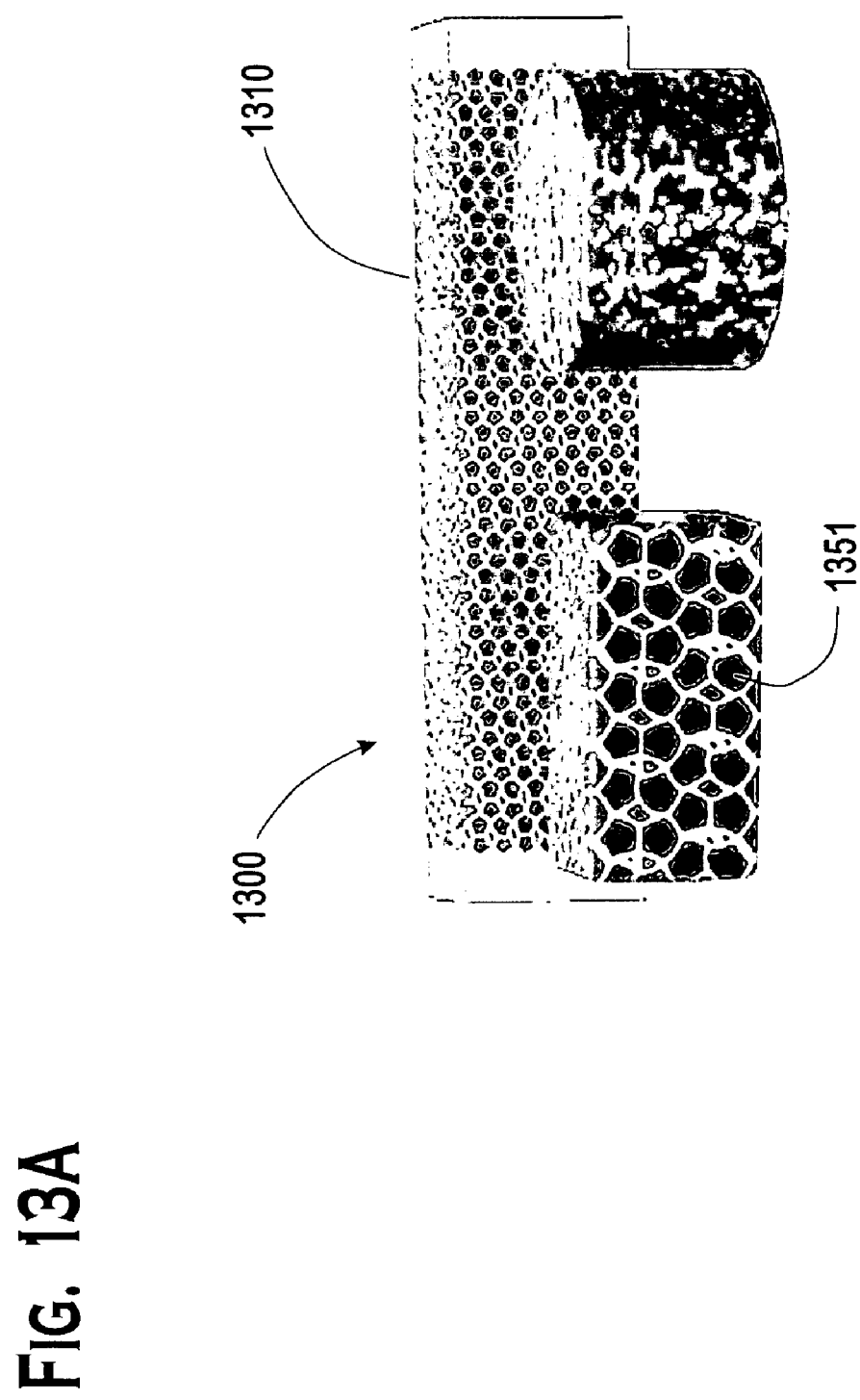
FIG. 13A show a polymer infused porous structure according to the present invention.
Figure 13B:
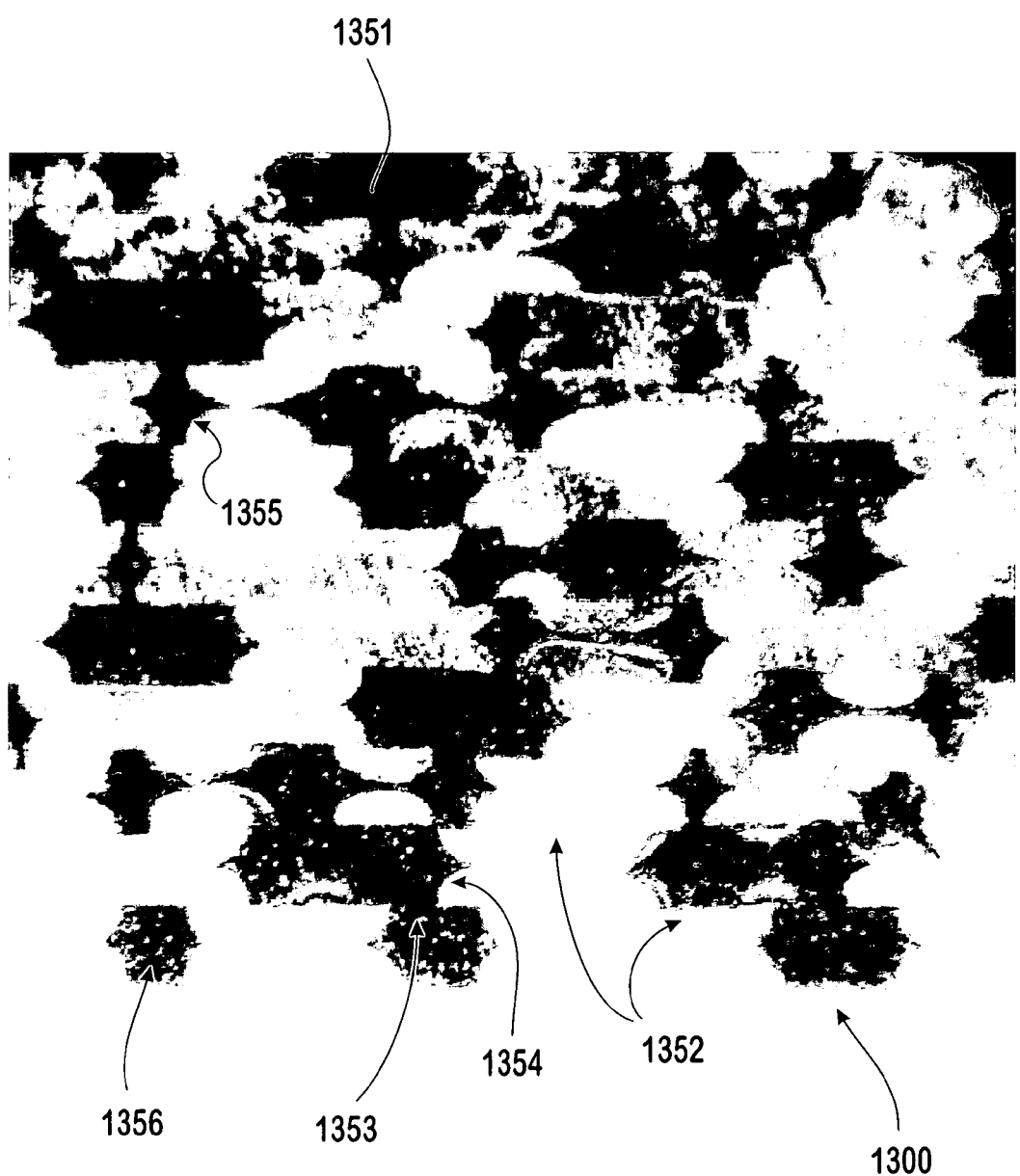
FIG. 13B shows a cross section of a polymer infused porous structure according to the present invention.
Figure 13C:
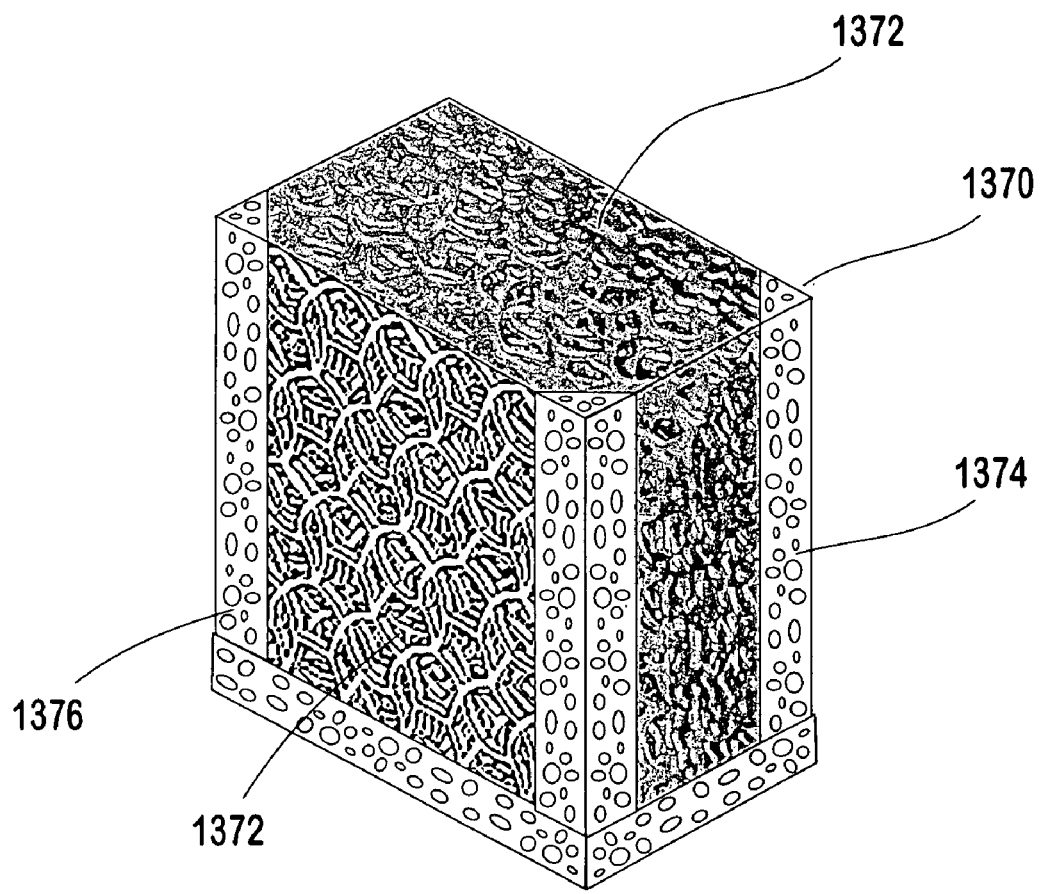
FIG. 13C–E shows a hybrid porous structure according to the present invention.
Figure 13D:
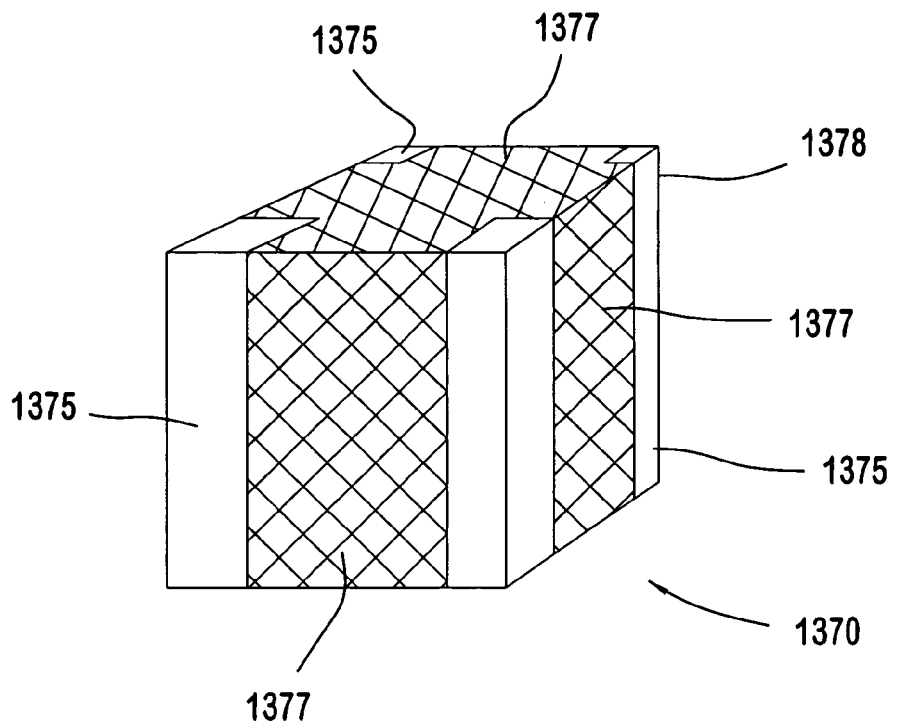

FIG. 13A illustrates a porous structure 1310 with infused polymer 1351, and FIG. 13B illustrates a cross section of porous structure 1310 infused with polymer 1351. As illustrated in FIG. 13B, porous structure 1310 includes sheets 1352 with pores 1353 that have been filled with polymer 1351. Pores 1353 can have any shape defined by the features of sheets 1352 or by a combination of sheets 1352. In one embodiment, the features of sheets 1352 includes feathered edges 1354, round edges 1355, hexagonal pores 1356 and a multitude of other irregular and regular shapes. Sheets 1352 preferably are titanium sheets. In one embodiment, RTV silicone rubber is used as polymer 1310 infused as a filler. In another embodiment, epoxy resin is the polymer and the composite porous structure 110 is hybrid conductive/dielectric structure, or an air-tight composite of a high stiffness-to-weight ratio.

Other methods of post processing include application of a porous coating and/or application of a polymer coating or other coating such as an osteotropic, osteocompatible or precursor material such as a hydroxyapetite or any cell or tissue growth enhancing or accelerating factor including human growth hormone, epidermal growth factor, and/or bone growth factors. Other embodiments may include the application of anti-infection, anti-rejection or therapeutic type drugs either on the surface of or within porous structure 110. In one embodiment, anti-infection, anti-rejection or therapeutic type drugs are incorporated into a polymer which is applied to the surface of porous structure 110 or infused into porous structure 110. In one embodiment, at least one of sheets 200 includes a polymer that includes an active ingredient such as a drug or a functional material such as a coating.

In one embodiment, porous structure 110 may be plasma sprayed with a bonding agent which is in turn covered with a porous ceramic coating which would allow the in-growth of bone spicules into the pores, for example, as that process is described in U.S. Pat. No. 4,145,764 which is hereby incorporated by reference.

Applications

Figure 8A:
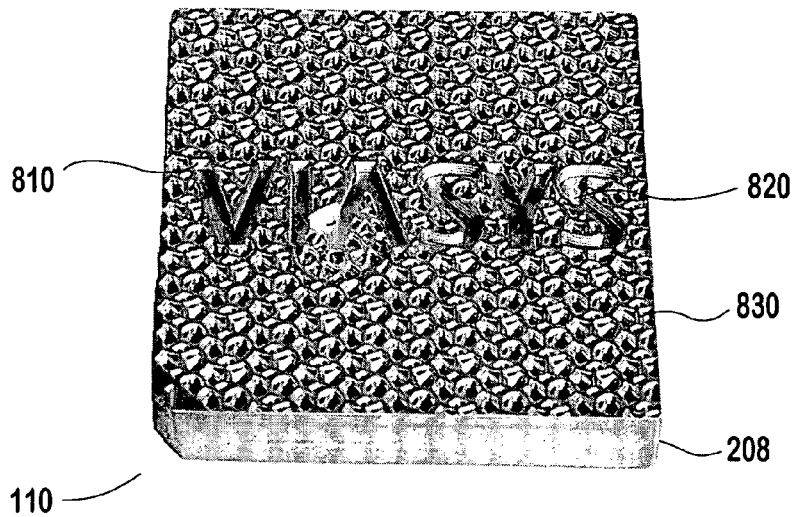
FIGS. 8A–C show exemplary porous structures according to the present invention.
Figure 8B:
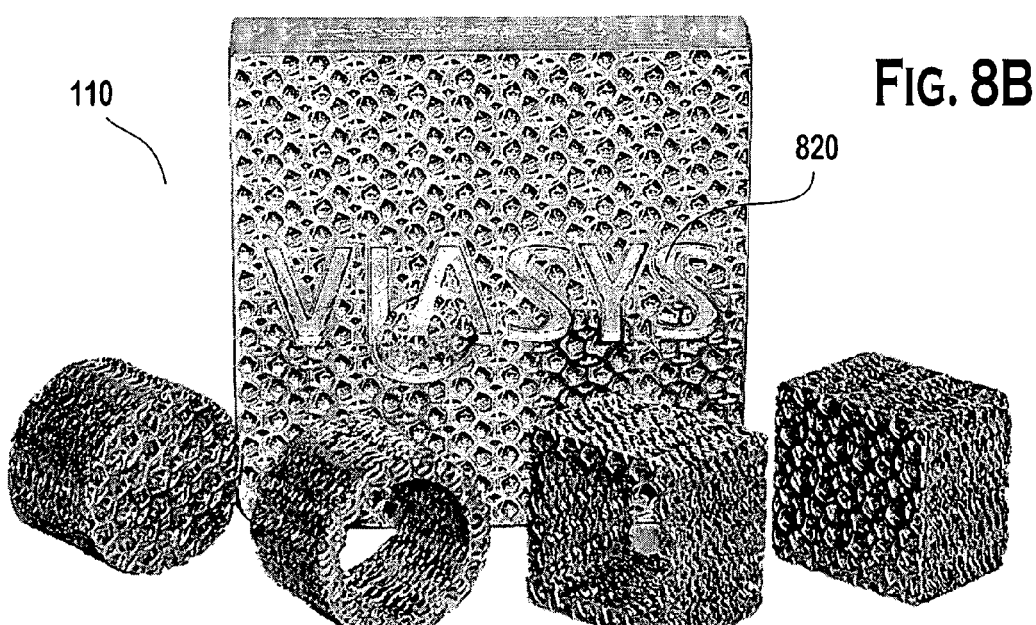
Figure 8C:
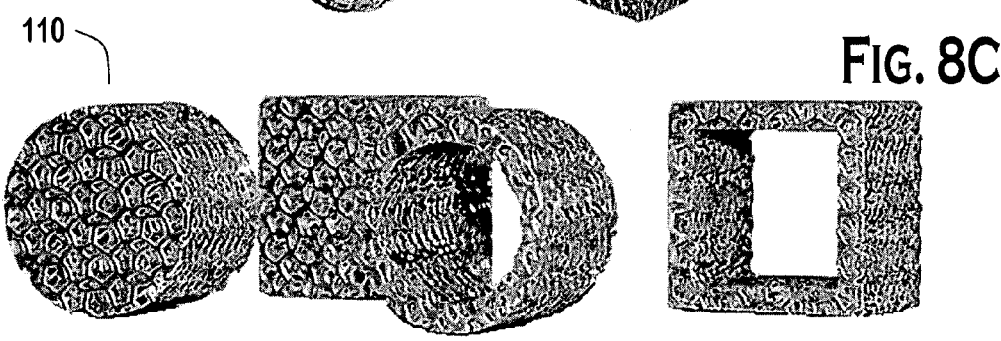

In one embodiment illustrated in FIG. 8A–C, a plurality of the sheets form a bonded sheet set 208 containing porous regions 810, blank regions 820 and web 830. By aligning porous regions 810, blank regions 820 and/or webs 830 in a predetermined configuration, design affects can be achieved which are engineered to solve the need of a particular application. Because each layer may be different, complex structures of open pores with integral solid support or attachment regions may readily be prepared. Solid regions of porous structure 110 preferably provide additional stiffness to porous structure 110, and/or form mounting flanges, bosses, or attachment points.

In another embodiment a variety of three-dimensional structures may be formed from porous structure according to the present invention. FIGS. 8A–C illustrates a variety of shapes that may be formed as described above. Additional geometric forms can be achieved by, for example, forming blocks of open pore structures and machining (e.g., by EDM) the block to a desired geometry such as cylinders, spheres, cones, and cubes. Among the benefits of the porous structure of the present invention is the ability to cold or hot work the porous structure without a significant loss in porosity.

Figure 9:
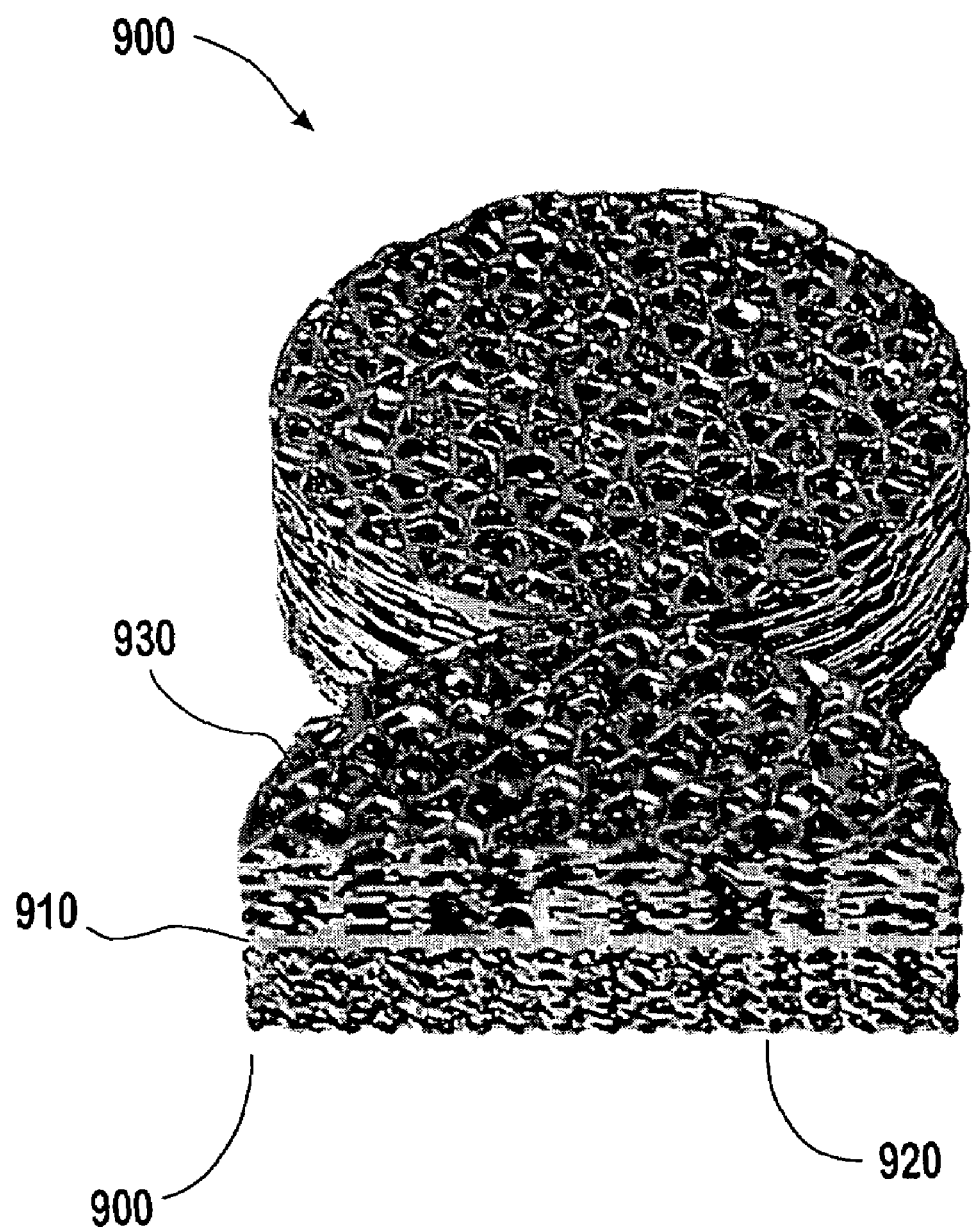
FIG. 9 shows a cross section of one embodiment of an open pore structure having two sides of varying porosity and separated by a solid section according to the present invention.

In one embodiment, illustrated in FIG. 9, open pore reticulated structure 900 is bisected by boundary 910. Boundary 910 is unperforated or partially perforated. In one embodiment, Boundary 910 is created from sheet 200 having partial aperture 307 as shown in FIGS. 3C–3D. In one embodiment, one or more sheets 200 are included in boundary 910.

In one embodiment, open pore region 920 on one side of boundary 910, has the same or different porosity characteristics as open pore region 930 on the other side of boundary 910. Thus, for example, an open pore reticulated structure of the present invention may have one or both sides of a partition are sufficient or optimized for bone ingrowth, or one side for bone or tissue ingrowth and one side is sufficient or optimized, for example, for a natural or synthetic polymer, bone or tissue attachment. Such embodiments are suitable for producing medical implants such as, for example, the implants described in FIGS. 10, 11A, 11B, and 12A.

Any of the embodiments of the present invention may be treated with any coating, including but not limited to an active ingredient, pharmaceutical or a natural or synthetic tissue or combinations thereof. In one embodiment, for example, open pore region 920 on one side of boundary 910 may be treated with a composition containing a particular active ingredient, pharmaceutical, functional material or tissue, and open pore region 930 on the other side may be treated with a composition containing the same or a different active ingredient, pharmaceutical, functional material or tissue (e.g., human growth hormone, fibroblasts, stem cells, or any material or compound that may facilitate treatment, tissue growth, anti-infection, anti-rejection and/or therapeutic type drugs or compounds).

In another embodiment, fluid being carried in the open pore structure 920 on one side of solid boundary 910 may be separated from fluid carried in the open pore structure 930 on the other side of boundary 910. Boundary 910 may be solid, semi-solid, textured or of a finer porosity that prevents the passage of fluids, fibers, drugs or other compounds.

Another example of such a configuration may be a heat exchanger such as where, for example, transmission fluid is being carried on one side and antifreeze on the other.

FIG. 13A illustrates a porous structure 1300 with infused polymer 1310, and FIG. 13B illustrates a cross section of porous structure 1300 infused with polymer 1310. As illustrated in FIG. 13B, porous structure 1300 includes sheets 1352 with pores 1353 that have been filled with polymer 1351. Pores 1353 can have any shape defined by the features of sheets 1352 or by a combination of sheets 1352. In one embodiment, the features of sheets 1352 includes feathered edges 1354, round edges 1355, hexagonal pores 1356 and a multitude of other irregular and regular shapes. Sheets 1352 preferably are titanium sheets. In one embodiment, RTV silicone rubber is used as polymer 1310 infused as a filler. In another embodiment, epoxy resin is the polymer and the composite porous structure 110 is hybrid conductive/dielectric structure, or an air-tight composite of a high stiffness-to-weight ratio.

In one embodiment, porous structure 110 is connected (e.g., bonded) to a medical implant. Among the categories of medical implants that will be improved by porous structure 110 are orthopedic devices and implants (e.g., spinal implants, digital implants), dental devices and implants, augmentation devices and implants (e.g., augmentation plates, augmentation blocks, augmentation discs and preformed acetabular cups) and articulating devices and implants (e.g., spinal pieces).

Orthopedic Applications

It will be appreciated by those of skill in the art that the specific embodiments disclosed herein are exemplary and that porous structure 110 including hybrid composites that include a polymer, and the various configurations described can be utilized in any orthopedic design to achieve the objectives and benefits described herein.

Porous structure 110 with infused polymer or coupled to a polymer (e.g., UHMWPE) has especially significant applicability to vertebral prosthetics such as orthopedic implants (e.g., "spinal cage" implants) and other orthopedic implants such as acetabular cups, because of the shock-absorbing and/or physiological and/or chemical properties of some polymers in combination with the strength of the lightweight porous structure 110.

Figure 10:
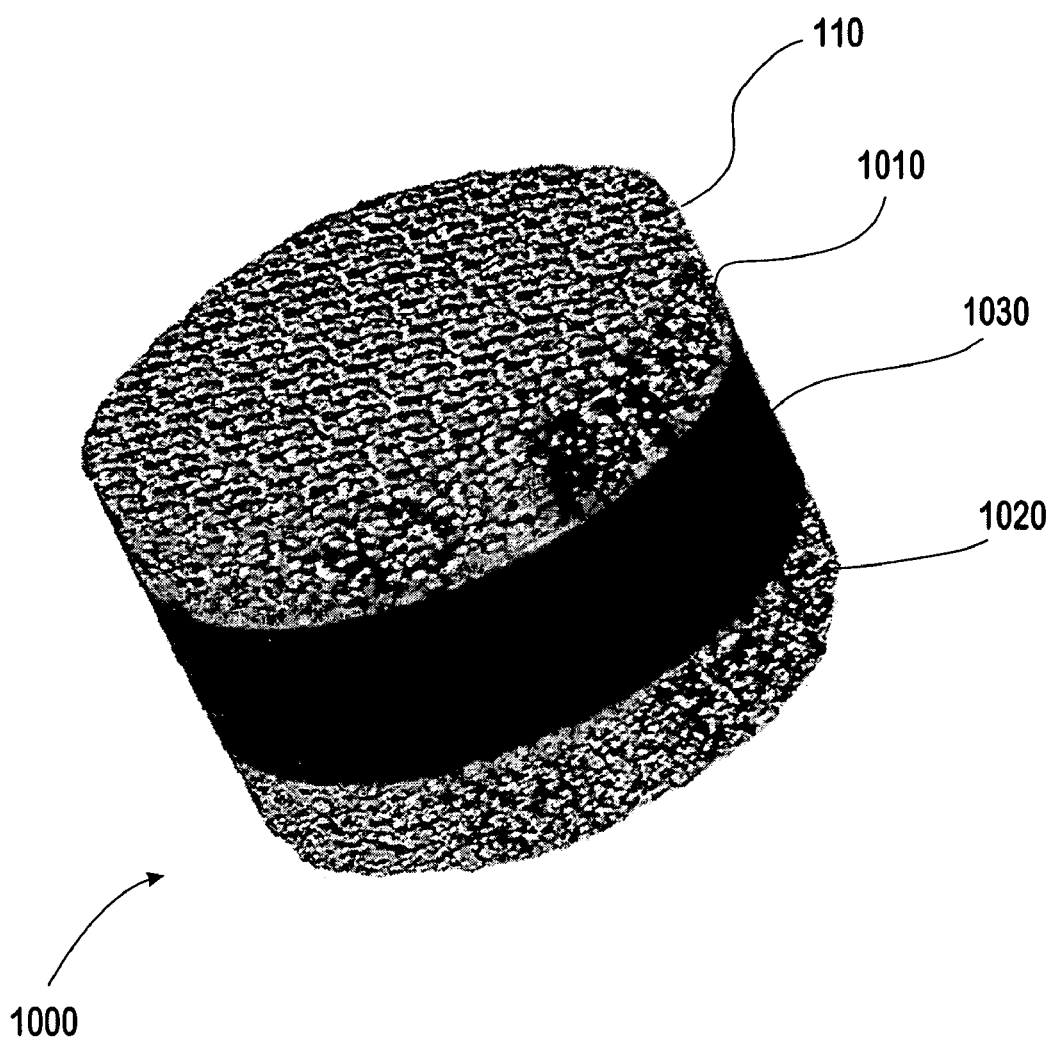
FIG. 10 shows an exemplary porous structure including a polymer infused portion according to the present invention.

In one embodiment, illustrated in FIG. 10 a selected polymer (e.g., UHMWPE) or other material is infused to a predetermined depth of defined region 1010 of an open pore reticulated structure 1020. In a preferred embodiment, the pore volume in defined region 1010 is not greater than 45%. In one embodiment, the bond depth preferably is not less than 5 mm. In one embodiment, polymer 1030 is pressure injected into defined region 1010. Polymer 1030 may also be infused into defined region 1010 by compression molding or any other suitable process. In one embodiment, region 1010 is defined by a boundary 910 (as shown in FIG. 9) within porous structure 110. In one embodiment, boundary 910 is textured or has a fine porosity. In one embodiment, during compression molding, polymer is substantially blocked from passing through boundary 910 (e.g., into the tissue growth portion of porous structure 110) but, air passes through boundary 910. In one embodiment, polymer infusion preferably is controlled by controlling temperature and pressure conditions during polymer infusion or compression molding. By controlling temperature and pressure, a skilled operator will be able to control the depth of polymer 1030 in defined region 1010.

Device 1000 includes a resilient polymer section 1030. Polymer 1030 may be an elastomer (e.g., resilient 40 Durometer urethane) or any other type of polymer depending on the desired application. Polymer 1030 is securely molded between two porous structures 110. In one embodiment, shock loads are applied to device 1000 and polymer 1030 dampens or absorbs at least a portion of the shock. One application may be for use in spinal implants.

Figure 11A:
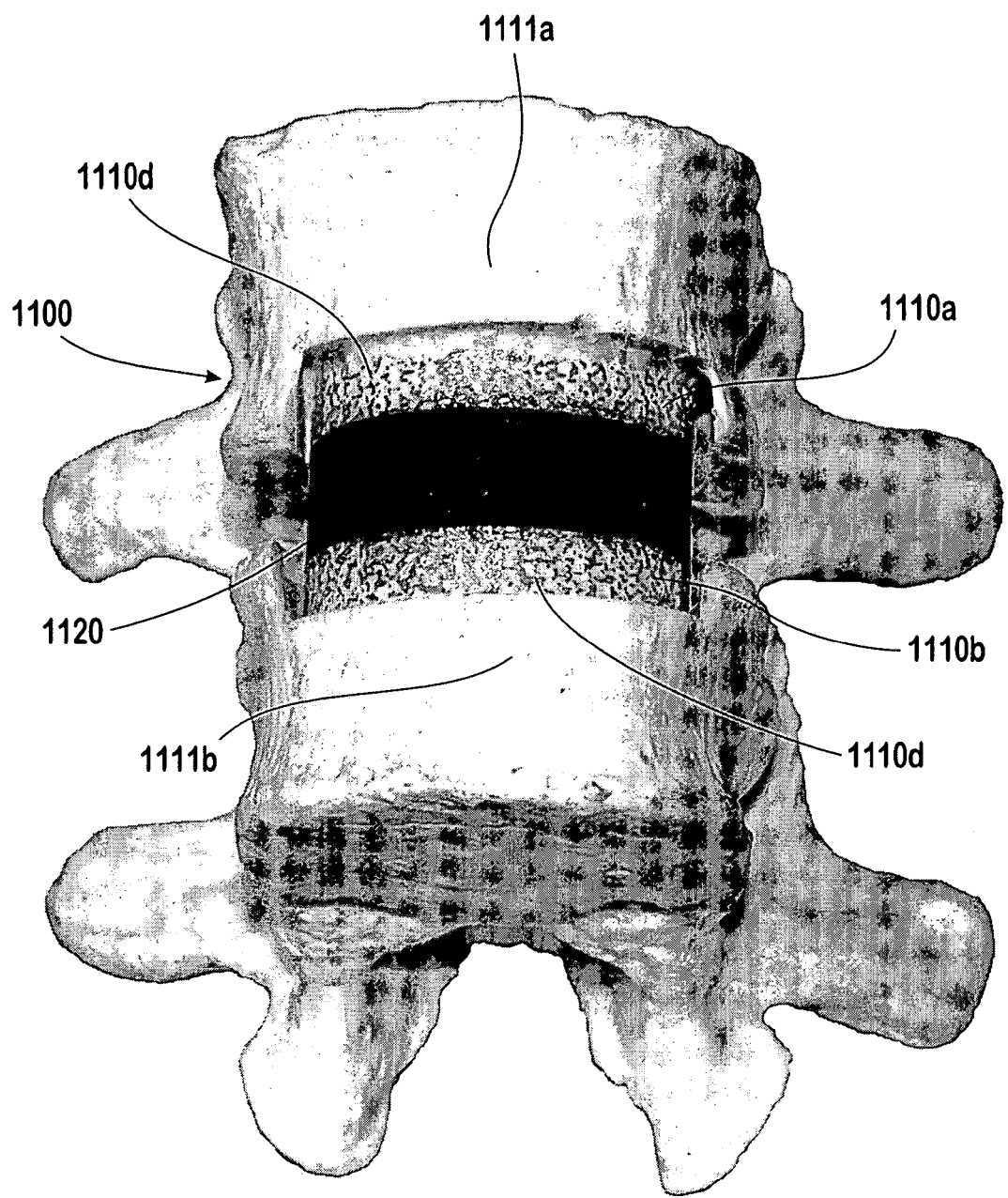
FIGS. 11A–B shows one embodiment of a spinal implant including a porous structure according to the present invention.
Figure 11B:
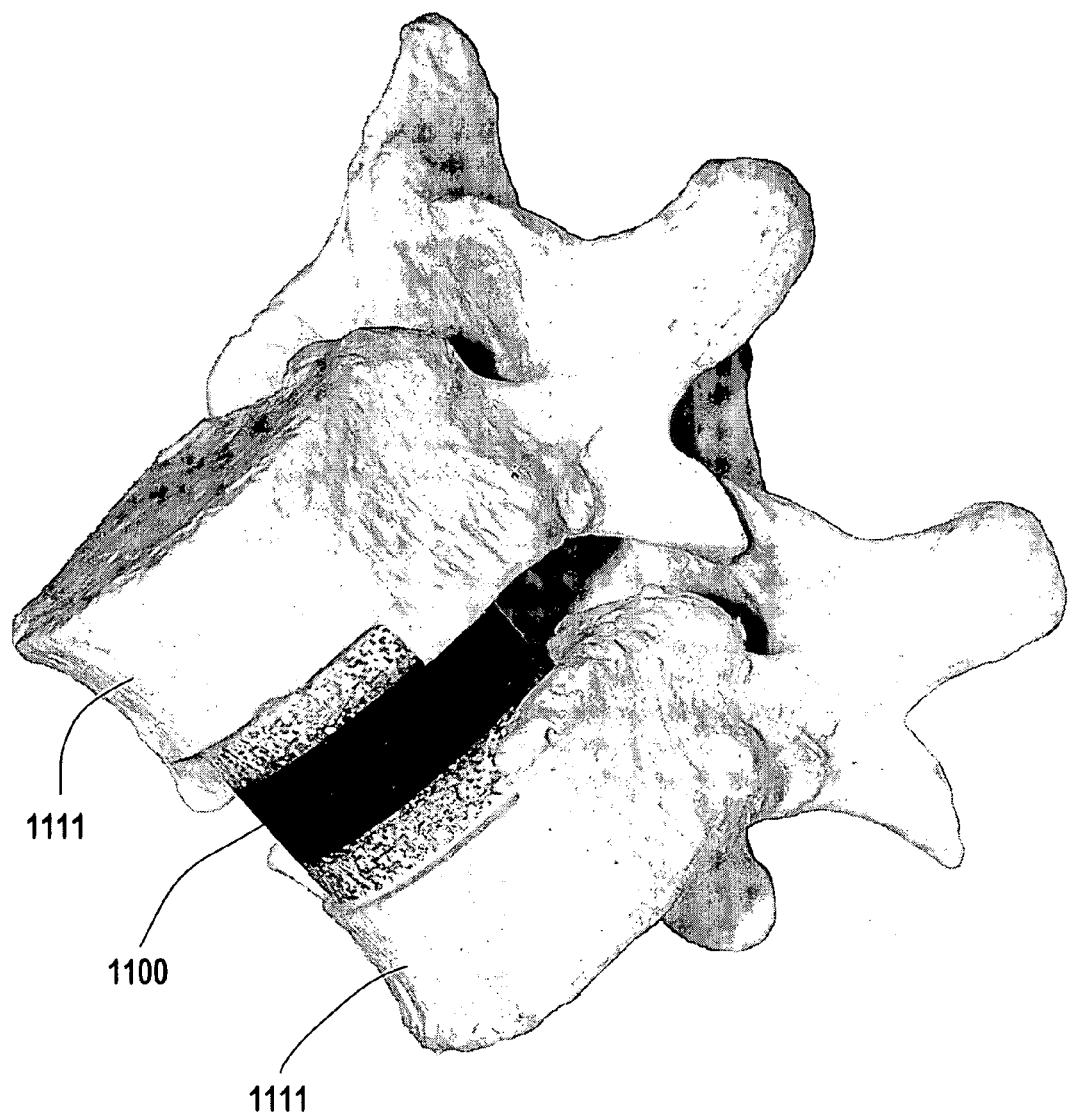
Figure 11:
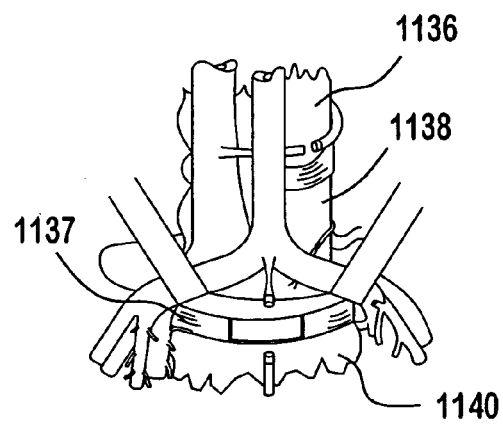
FIGS. 11C–11F shows embodiments of spinal implants including a porous structure of the present invention.
FIGS. 11G–11H shows embodiments of porous sheets according to the present invention.
Figure 11:
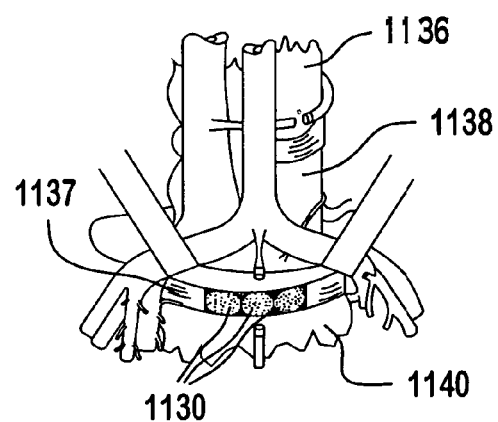
Figure 11:
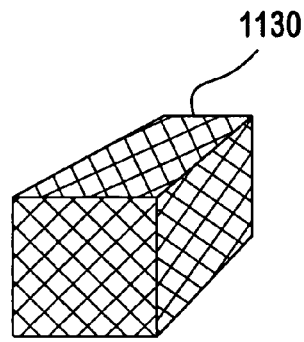
Figure 11:
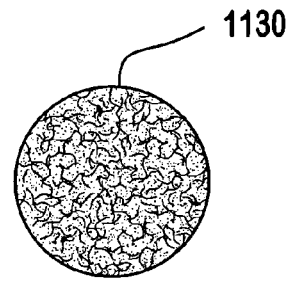
Figure 11:
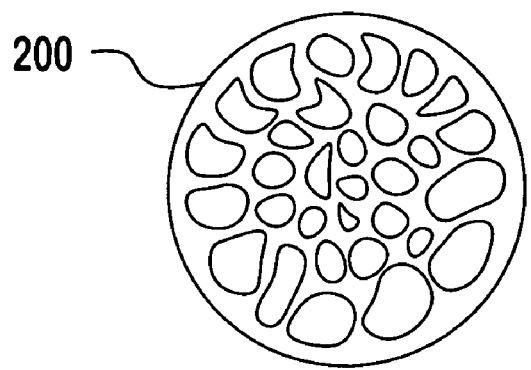
Figure 11:
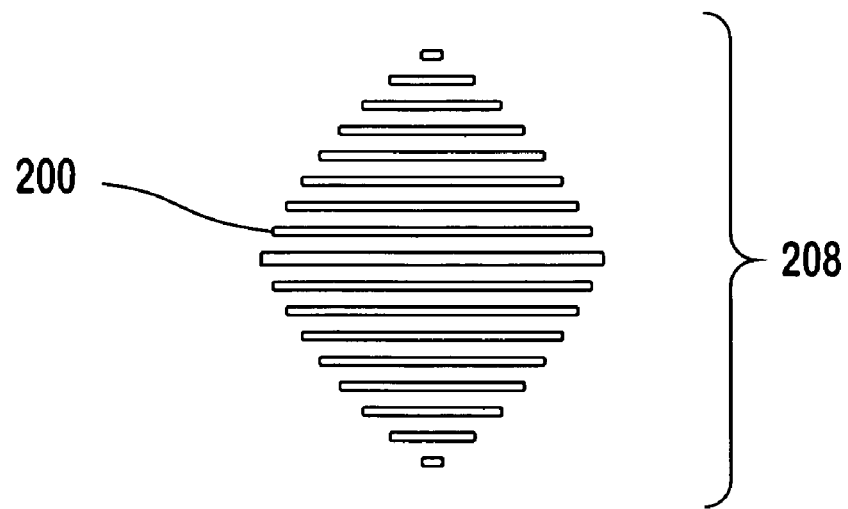

FIG. 11A and 11B illustrate an embodiment of a spinal implant 1100 of the present invention. Spinal implant 1100 includes porous structures 110a and 110b and polymer 1120. Polymer 1120 has been infused into a portion of porous structure 1110a and into a portion of porous structure 1110b creating an implant for use in replacing a spinal disc for portions of vertebra 1111a and 1111b. Polymer 1120 is any biocompatible polymer that a person skilled in the art will select for this application. Preferred polymers include nylons, urethanes, silicone elastomers, some epoxies (e.g., sufficiently hydrolytically stable polymers such as those used in pacemaker domes), PEEK polyacetals, polyesters and other such recognized polymers. As illustrated in FIGS. 11A and 11B, bone tissue 1110d is encouraged to migrate into porous structure 1110 thereby creating a strong bond between implant 1100 and vertebra 1111. In one embodiment, bone migration is encouraged by methods described in U.S. Pat. No. 6,599,322 or co-pending U.S. patent application Ser. No. 10/202,575. In one embodiment, porous structure 1110 has surface features that produce surfaces that are self-grafting and which, for example, shear the surface of bone or other tissue upon implantation and pack the bone or tissue material into the implant to promote bone or tissue in-growth or on-growth.

In one application, porous structure 1110 is constructed from a biocompatible resorbable polymer sheets 200. Over time, as the resorbable polymer is consumed by the body, the bone tissue that migrates through the porous structure 1110 will bond to the polymer 1120 for a disc/vertebra bond that very nearly approximates the natural connection between disc and vertebra.

Spinal Spacers

U.S. Pat. Nos. 6,673,075 and 5,961,554, which are hereby incorporated herein by reference, describe porous intervertebral spacers. In one embodiment, porous structure 110 is used to form porous intervertebral spacer 1130 (FIGS. 11C–11E). In one embodiment, porous intervertebral spacers 1130 are inserted between adjacent vertebrae 1136, 1138, for example, by replacing a portion of intervertebral disc 1137 and engaging portions of the adjacent vertebral bodies 1136, 1138, and 1140. In one embodiment, intervertebral spacers 1130 are surgically inserted between vertebrae 1138 and sacrum 1140. In one embodiment, a plurality of spacers 1130 are used. In one embodiment, the plurality of spacers are inserted adjacent to one another. The number of intervertebral spacers 1130 and the location in which those spacers are placed are selected based upon factors well known in the art. In one embodiment, three intervertebral spacers 1130 having a rectangular configuration are implanted (FIGS. 11D and 11F).

Porous intervertebral spacers 1130 of any size or shape can be manufactured using the methods described herein. Porous intervertebral spacers 1130 are of any geometrical configuration and are preferably rectangular, cubic, cylindrical, octahedron, spherical or any other Euclidean solid (e.g., FIG. 11E, 11F). Porous intervertebral spacers 1130 may be of any desired symmetry.

In one embodiment for manufacturing porous intervertebral spacers 1130, the desired shape is computer designed with the desired perforated patterns in individual sheets (e.g., sheets 200). The dimensions of the individual sheets are determined based upon the desired dimensions of the finished porous intervertebral spacer 1130. For example, in one embodiment, a cube is made by a stack of four-sided square sheets 200 wherein the final bonded height equals the dimensions of the sides of the square sheets.

In another embodiment, illustrated in FIGS. 11H and 11G a spherical or substantially spherical porous structure (e.g., 1130) is made of round perforated sheets 200 with varying individual diameters that correspond to the sheet's position along an axis of the sphere. Thus for example, in one embodiment, each sheet 200 represents a "slice" through a sphere, wherein the thickness of the slice is the thickness of the individual sheet 200 (FIG. 11G). In one embodiment, a stack of sheets 208 to be bonded would consist of a set of circles having a very small circle at one end (e.g., a pole of the sphere) with a slightly larger circles stacked above the smaller circle until, at the assembly of half the sheets, one would reach the equatorial dimension of the intended sphere. The remaining sheets, in one embodiment, would then be sequentially smaller (e.g., culminating in the opposing pole of the sphere; FIG. 11G).

In one embodiment, intervertebral spacers are symmetrical about at least three perpendicular axes. In one embodiment, the spacers are suitable to being installed laparoscopically at least in part due to the uniformity of their orientation along numerous axes (e.g., being orientation independent).

Acetabular Cup

Figure 12A:
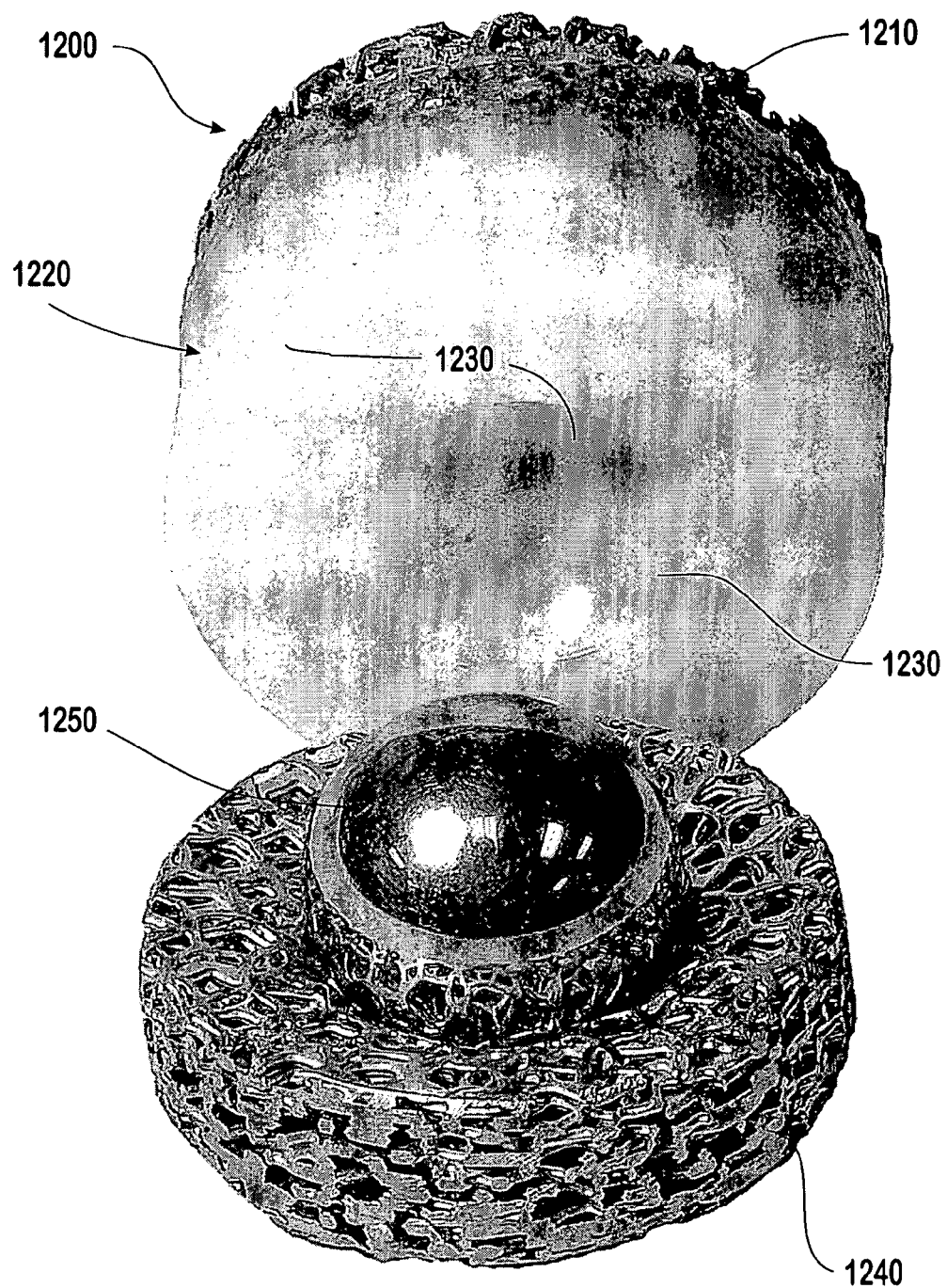
FIG. 12A shows one embodiment of a ball and socket joint of a structure according to the present invention.

FIG. 12A illustrates one configuration of the present invention for use in applications requiring high porosity and low friction characteristics such as device 1200 (e.g., a hip prosthesis). Porous structure 1210 has been partially infused with polymer 1220 such as by any other methods described herein. Thus there is a portion of porous structure 1210 that has no polymer infusion and a portion of porous structure 1210 that has been polymer infused (e.g., the polymer is interdigitated within porous structure 1210). In one embodiment, polymer 1220 is a UHMWPE, cross-linked polyethylene (XLPE) or any other biocompatible polymer or polymer based composite that are known to those skilled in the art (e.g., nylons, urethanes, silicone elastomers, some epoxies, PEEK polyacetals, polyesters and other such recognized polymers). In FIG. 12A, polymer 1220 has been formed as a first bearing surface 1230. First bearing surface 1230 can be formed by molding or by machining by methods well known in the art.

In one embodiment, porous structure 1210 can be machined (e.g., cold worked) to form the concave face of an acetabular cup (e.g., bearing surface 1230). Porous structure 1210 may then be treated (e.g., oxidized, or infused with polymer) to achieve any of the desirable qualities of bearing surface 1230 which are known to those of skill in the art (e.g., low friction, inert, therapeutic). In one embodiment, a polymer lining is infused within an acetabular cup formed by machining to form first bearing surface 1230. In one embodiment, because it is only partially infused with polymer 1220, porous structure 1210 remains available for migration of bone tissue (e.g., from an adjoining shoulder, arm, leg or pelvic bone) which will form a strong bond between, for example, the implant and the tissue.

There is also shown in FIG. 12A a second bearing surface 1250. Second bearing surface 1250 is configured to articulate about first bearing surface 1230. In one embodiment second bearing surface 1250 is a femoral head first bearing surface 1230 is a lining for an acetabular cup. Second bearing surface may also be a humerus head or any other similar ball device useful in a ball and socket application.

Porous structure 1240 and second bearing surface 1250 can be of the same or different materials including any of the refractory materials and polymers described herein. Porous structure 1240 and second bearing surface 1250 are bonding by any of the methods described herein more preferably by diffusion bonding. In preferred embodiments head second bearing surface 1250 has an oxidized zirconium surface as described in U.S. Pat. No. 6,652,586 which is hereby incorporated by reference. Second bearing surface 1250 may also be zirconium or zirconium containing metal alloy coated via in-situ oxidation with a surface of blue-black or black oxidized zirconium as described in U.S. Pat. No. 5,037,438 which is hereby incorporated by reference. Second bearing surface 1250 may also include a carbide coating as described in U.S. Pat. No. 3,677,795 which is hereby incorporated by reference. Second bearing surface 1250 may be white or beige oxidized zirconium. Second bearing surface 1250 may be of any other biocompatible material. In one embodiment, one of second bearing surface 1250 or porous structure 1240 are made of polymer (e.g., any of those disclosed herein) and the other of second bearing surface 1250 or porous structure 1240 are made of a metal (e.g., any of those disclosed herein). In one embodiment, one of second bearing surface 1250 or porous structure 1240 are made of titanium and the other of second bearing surface 1250 or porous structure 1240 are made of zirconium.

Porous structure 1240 and second bearing surface 1250 can be formed separately and bonded by any method known to those skilled in the art including but not limited to those methods described herein for bonding sheets 200 to one another. Preferably, porous structure 1240 and second bearing surface 1250 are bonded together by diffusion bonding. In a preferred embodiment, porous structure 1240 is configured to approximate any portion of the neck (e.g., femoral or humerus neck). Porous structure 1240 can also be incorporated into any portion of the prosthetics identified in U.S. Pat. No. 6,652,586 that illustrate a textured regular or irregular surface. Applying porous structure 1240 as a textured regular or irregular structure as described herein preferably will encourage tissue to migrated throughout porous structure 1240 to form a secure bond between prosthesis 1200 and the adjacent tissue (e.g., femur or humerus tissue).

Porous structure 1210 may be incorporated into any portion of a prosthetic device including those prosthetic devices with a ball and socket joint (e.g., hip, shoulder). In FIG. 12B, illustrating one embodiment of a prosthetic hip, porous structure 110 may be incorporated into the acetabular cup, 1261, lining 1265, femoral head 1266, and hip joint stem 1262. Porous structure 110 may also be used as a substitute for any textured prosthetic surface such as textured surface 1260 on hip joint stem 1262.

In one embodiment, porous structure 110 is used as a liner 1265 for an acetabular cup (e.g., that has been damaged by a failed implant that had to be removed). In one embodiment, the liner is a hemispherical liner. In one embodiment, an acetabulum is enlarged (e.g., by the prior surgery and by the implant failure) and bone loss has occurred to the extent that a hemispherical liner needs to be installed. Preferably, the hemispherical liner has a cup-like shape with perforations for attachment of hardware. The method of attaching hardware to the perforations may be any method known to those of skill in the art including the use of adhesives such as cement.

As show in FIG. 12D, acetabular cup 1261 may be prepared by forming sheets 200 into a series of annular rings 1263 that are slices of a partial or full sphere, with an outer region having a desired open porous pattern, and a smooth inner layer or a porous inner layer. In one embodiment, the desired shape is formed during the diffusion bonding process. In one embodiment, porous structure 110 is machined or forged into a desired shape after the diffusion bonding process. In one embodiment, after diffusion bonding, finish machining, forming and/or forging the annular rings, the resulting acetabular cup 1261 is a hemisphere having an outer region 1269 that is an assembled porous structure 110 optimized for (e.g., to accept) bone ingrowth, and having an integrally formed inner spherical region 1268 that is smooth or porous, uninterrupted metal or polymer. In one embodiment, one or more of the regions are separated by a barrier layer (e.g., 910 in FIG. 9) that is solid, semi-solid, textured and/or of a finer porosity than the adjacent regions. In one embodiment, inner surface 1268 is made of an open pore structure region according to the present invention having a porosity and internal geometry that are optimized for an attachment of a metal (e.g., zirconium) or a polymer (e.g., compression-molded UHMWPE).

As shown in FIG. 12E, any ball and socket joint 1290 can be prepared by combining (e.g., as described herein) porous structure 1291 according to the present invention, and lubricious structure 1292 (e.g., zirconium or polymer). In one embodiment, a medical implant according to the present invention includes an intermediate layer 1293 of any material described herein, including but not limited to titanium, between porous structure 1291 and lubricious structure 1292.

Knee

The present invention is useful for any prosthetic knee design including multi-piece, uni-piece and partial knee replacement systems. U.S. Pat. Nos. 6,652,586 and 6,494,914, incorporated herein by reference, discloses a knee prosthesis as illustrated in FIG. 12C. Knee prosthesis 1251, illustrated in FIG. 12C, includes a femoral component 1270 and a tibial component 1280. Femoral component 1270 includes condyls 1272 and pegs 1271. Tibial component 1280 includes a tibial base 1282 and one or more pegs 1283. Condyls 1272 in the present invention may have a solid bottom surface 1273 (e.g., coated with an oxidized zirconium surface) and an upper surface 1274 (e.g., including a porous structure 110 as described herein. Porous structure 110 can be used to form all or part of any component of knee prosthesis 1250 including femoral component 1270, tibial component 1280, tibial base 1282 condyles 1272, pegs 1271 and 1281, and grooves 1283.

In one embodiment, upper surface 1274 and lower surface 1273 are formed together by the stack bonding process described herein and then shaped (e.g., by cold working the bonded piece). In one embodiment, the bonded piece is hot formed or forged to the desired shape. In one embodiment, condyls 1272 are formed by bonding (e.g., as described herein such as by diffusion bonding) a plurality of pieces. For example, in one embodiment, separate pieces that include upper surface 1279a and lower surface 1279b respectively are bonded together to form condyl 1272. In one embodiment, peg 1271 is at least partially a porous structure and is bonded to upper surface 1274 (by e.g., diffusion bonding).

In one embodiment, tibial base 1282 has an upper surface 1283 and lower surface 1284. In one embodiment upper surface 1283 is non-porous surface coated with oxidized zirconium, and a lower surface 1284 that is formed from a porous structure 110 of the present invention. Upper surface 1283 and lower surface 1284 may be formed together or formed separately and bonded together as described herein. In one embodiment, peg 1281 includes a porous structure 110 of the present invention. In one embodiment, peg 1281 is integral to lower surface 1284. In another embodiment, lower surface 1284 and peg 1281 are formed separately and bonded together as described herein. Upper surface 1283, in one embodiment, is a polymer (e.g., compression molded UHMWPE) that is compression molded into lower surface 1284.

Figure 12F:
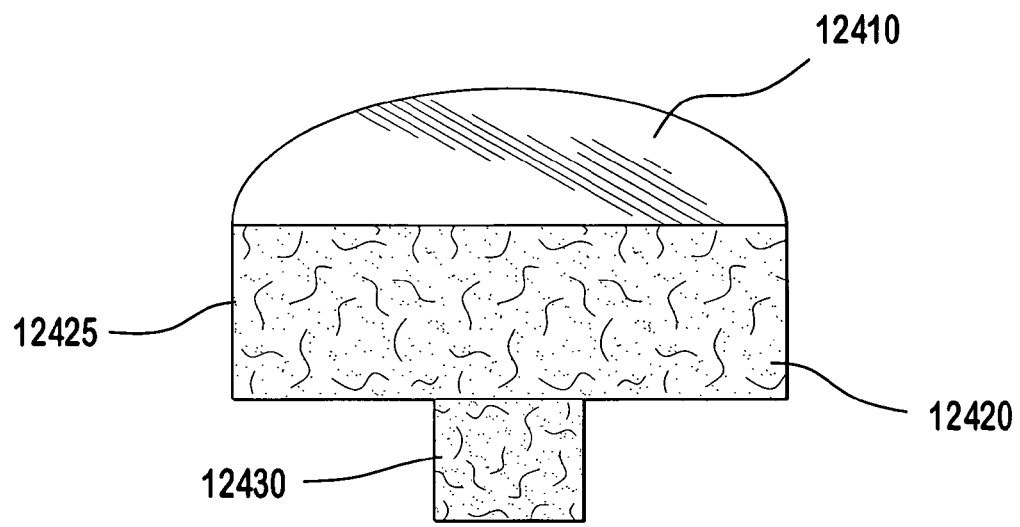
FIG. 12F shows an embodiment of a device including a porous structure of the present invention.

In one embodiment, Illustrated in FIG. 12F, a dome shaped bearing surface 12410 (e.g., such as that preferred in patella implants and tibial trays) is affixed to a base 12420 having disk 12425 and stem 12430. In one embodiment, bearing surface 12410 is an antifriction surface. Any antifriction material may be used to form bearing surface 12410. In one embodiment, bearing surface 12410 includes or is treated with an antifriction surface. In one embodiment, the antifriction surface includes zirconium oxide. In another embodiment, the antifriction surface includes titanium nitride. In one embodiment, bearing surface 12410 is titanium that is coated with zirconium oxide. In one embodiment, antifriction surface treatments can also include the bonding of a suitable polymer (e.g., PEEK, UHMWPE). In one embodiment, the surface treatment includes molding the suitable polymer into and/or onto a surface (e.g., as illustrated in FIGS. 10, 12A).

Base 12420 preferably is at least partially formed of porous structure 110. Bearing surface 12410 can be fixed to base 12420 by any method known to those of skill in art. In one embodiment, bearing surface 12410 is affixed to base 12420 by compression molding. In one embodiment bearing surface 12410 and base 12420 are formed of a single contiguous material. Base 12420 may be of a single contiguous piece or it may be formed from a plurality of components. In one embodiment, base 12420 is formed in separate sections and bonded together. Stem 12430 may provide lateral fixation in various applications and may be formed of solid metal or porous structure 110 having the same or different porosity than base 12420. At least a portion of base 12420 (e.g., stem 12430), in one embodiment, is a solid body having a textured outer surface as disclosed in co-pending U.S. patent application Ser. No. 10/202,575.

Figure 12G:
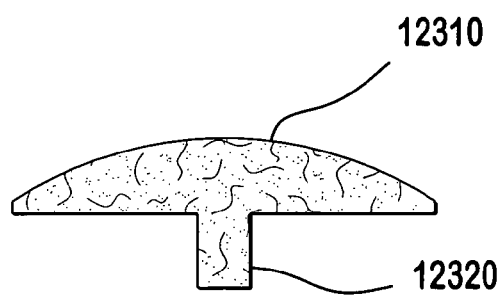
FIG. 12G shows an embodiment of a device including a porous structure of the present invention.

In an embodiment illustrated in FIG. 12G, a bearing surface 12310 is bonded to or integral with anchor 12320. Anchor 12320, in one embodiment, is an adherent implantable porous structure 110 used to anchor the structure. In one embodiment, bearing surface 12310 and/or anchor 12320 allow over-growth of tissue (e.g., cartilage). In one embodiment, improved tissue adhesion is achieved by providing oxidized zirconium that will self-burnish adjacent tissue (e.g., bone surfaces adjacent cartilage), while allowing certain tissue (e.g., cartilage) in-growth to occur. In one embodiment, there is less risk of scraping bone during cartilage in-growth and overgrowth. In one embodiment, a smooth outer surface coated with an antifriction coating (e.g., as described herein) may serve as a temporary joint to prevent excessive abrasion or wear of tissue (e.g., bone) which may contact the implant immediately after implantation. In one embodiment, the smooth, antifriction outer surface can protect contacting tissue (e.g., bone) from abrasion until other tissue (e.g., cartilage) can grow to interpenetrate the interfacial region.

Figure 12H:
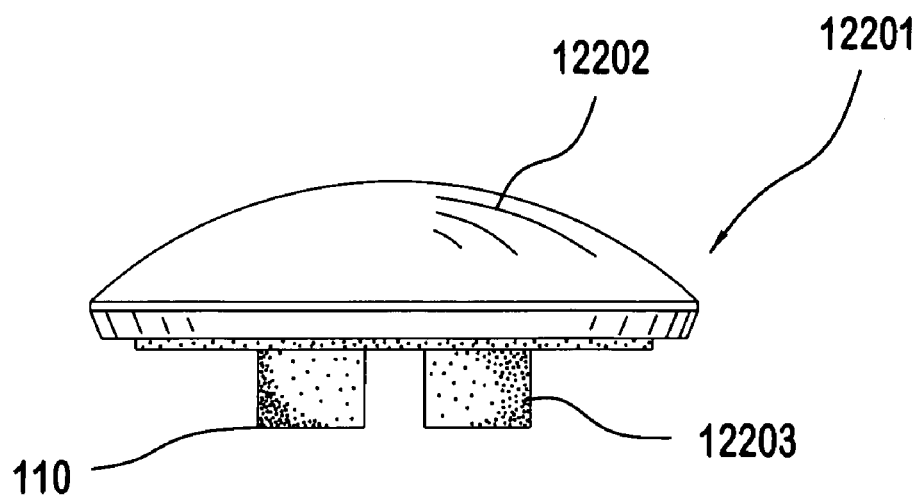
FIGS. 12H–12I show an embodiment of a patella button including a porous structure of the present invention.
Figure 12I:
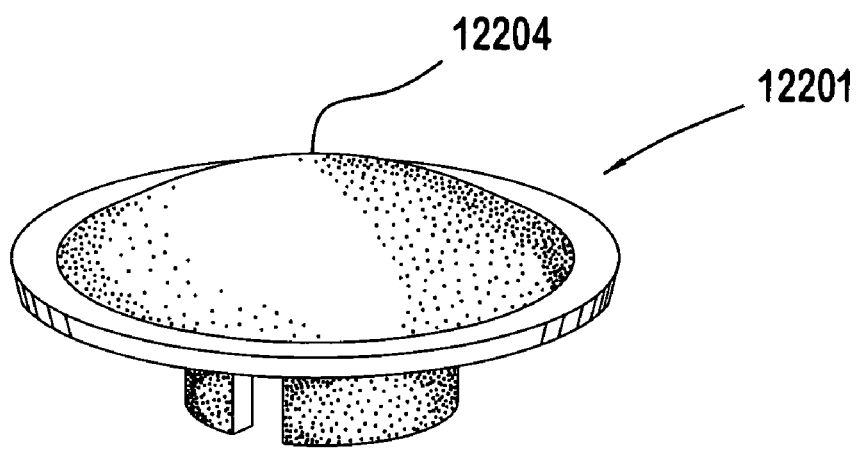

U.S. Pat. No. 5,024,670, incorporated herein by reference in its entirety, describes a patella implant. In one embodiment, illustrated in FIGS. 12H and 12I is patella button prosthesis 12201 of the present invention. Porous structure 110 may be incorporated into any or all of the components of patella implant 12201 including outer bearing surface 12202, backing component 12203 and dome 12204. Outer bearing surface 12202 may have any geometrical configuration including symmetrical and asymmetrical in relation to the center of backing component 12203. Outer bearing surface may be porous structure 110 that is bonded to achieve its geometrical configuration or it may be porous structure 110 that is machined to achieve its geometrical configuration. Outer bearing surface 12202 may be of any material preferably selected for its biocompatibility, wear properties and articulation properties including those materials described herein that are useful to form porous structure 110. In one embodiment, outer bearing surface 12202 is any antifriction material. In one embodiment, outer bearing surface 12202 is compression-moldable polymer. In one embodiment, outer bearing surface 12202 is UHMWPE, PEEK, ceramic or an appropriate metal (e.g., one that may be treated with an antifriction surface as described above such as zirconium or titanium). Antifriction surface treatments include, e.g., bonding of a suitable polymer, such as PEEK or UHMWPE as antifriction surfaces (e.g., FIG. 12A) and those described herein.

Backing component 12203 may be any material and preferably is constructed from the porous structure material 110 described herein. Outer bearing surface 12202 is preferably removably or nonremovably fixed to a backing component 12203. Preferably, outer bearing surface 12202 is compression molded onto a porous structure 110 (e.g., onto backing component 12203).

In one embodiment, backing component 12203 can be of any shape. In one embodiment, backing component 12203 has a dome 12204. Dome 12204 preferably is fixed to outer bearing surface 12202 which takes on the domed shape of backing component 12203. In another embodiment, backing component 12203 and outer bearing surface 12202 have different shapes (e.g., outer bearing surface 12202 having a rounded surface and backing component 12203 having a substantially flat surface).

Hybrid Composites

FIGS. 13A and 13B illustrates structural components 1300 that were constructed using the methods described herein. Porous structure 1310 was formed as described above and then altered using convention machining techniques (e.g., CNC machining, EDM). In one embodiment, porous structure 1310 is configured as a polymer engaging structure. In one embodiment, polymer is preferably infused into porous structure 1310 to take up substantially all of the pore space within structure 1310. The result is a solid, lightweight structural composite that is available for any purpose to which one of skill in the art can apply. Other hybrid composites can be prepared by infusing, for example, metal porous structure 110 with reactive resin materials such as epoxies, silicones, polyester resins, acrylics, etc. The result is preferably a solid material of great strength which possessing other beneficial properties of the infused materials. (e.g., acoustic damping, energy absorption, etc.). In one embodiment, radio opaque polymers (e.g., barium filled polymers) are infused within porous structure 110.

The present invention is useful for any prosthetic knee design including multi-piece, uni-piece and partial knee replacement systems. U.S. Pat. Nos. 6,652,586 and 6,494,914, incorporated herein by reference, discloses a knee prosthesis as illustrated in FIG. 12C. Knee prosthesis 1251, illustrated in FIG. 12C, includes a femoral component 1270 and a tibial component 1280. Femoral component 1270 includes condyls 1272 and pegs 1271. Tibial component 1280 includes a tibial base 1282 and one or more pegs 1283. Condyls 1272 in the present invention may have a solid bottom surface 1273 (e.g., coated with an oxidized zirconium surface) and an upper surface 1274 (e.g., including a porous structure 110 as described herein. Porous structure 110 can be used to form all or part of any component of knee prosthesis 1251 including femoral component 1270, tibial component 1280, tibial base 1282 condyles 1272, pegs 1271 and 1281, and grooves 1283.

Figure 13E:
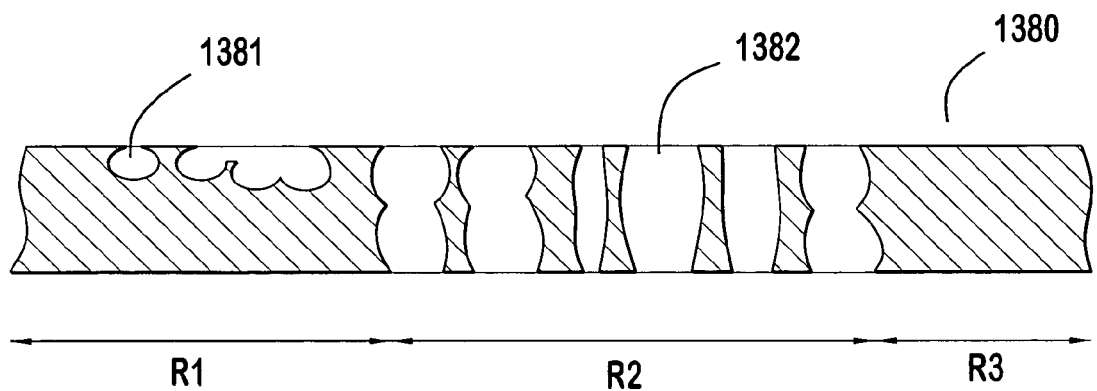

As shown in FIG. 13E, in one embodiment, hybrid structure 1370 is formed by assembling sheets 1380 having pre-formed porous, solid and/or semi-solid properties. In one embodiment, sheet 1380 has one or more region(s) R1 with pores 1381 that do not extend through sheet 1380, region(s) R2 with pores 1382 that do extend through sheet 1380, and region(s) R3 that are solid having substantially no pores. Sheets 1380 can be formed with regions R1, R2 and R3 of any combination and dimension. Pores 1381 and 1382 may be formed as disclosed in U.S. Pat. Nos. 6,599,322 and 6,620,332 and U.S. patent application Ser. No. 10/202,575. In one embodiment, pores 1381 create an undercut textured surface. In one embodiment, sheets 1380 have solid regions R3. In one embodiment, one or more sheets 1380 form barrier layers as described in various embodiments herein.

In one embodiment, hybrid structure 1370 has a layer thickness dimension of 0.015 inches in layer slice thickness. At the dimensional region of 0.002 inches of pattern perforation the region is approached where such structures may serve as platelet filters, or may participate in the growth of pseudointima tissue layers. In one embodiment, for example, upon implantation of an implant structure having hybrid structure 1370, clots form and interpenetrate hybrid structure 1370. As healing proceeds, adjacent tissues preferably use the clot as a growth scaffold and nutrient bed. The implant, thereby, preferably is attached, coated, and/or interpenetrated by cells which are of the same type as those at the implant site.

Dental Implant

U.S. Pat. No. 6,048,204, incorporated herein by reference, discloses a self tapping screw type dental implant. The present invention improves upon this device by utilizing the porous structure of the present invention to create the implant shown or by replacing or augmenting all or a portion of the implant, such as the internal or external body threads, with the porous structure of the present invention. Replacing threaded devices with devices having porous structure 110 (e.g., metal foam) allows interpenetration of the lattice of porous structure 110 with vital bone. Because dental implants lose the shock protection of the periodontal ligament seen in natural root anatomy, a more uniform distribution of chewing forces throughout a mass of vital bone, as opposed to traditional screw-thread boundary adhesion should improve retention and implant longevity.

Figures 14A, 14B:
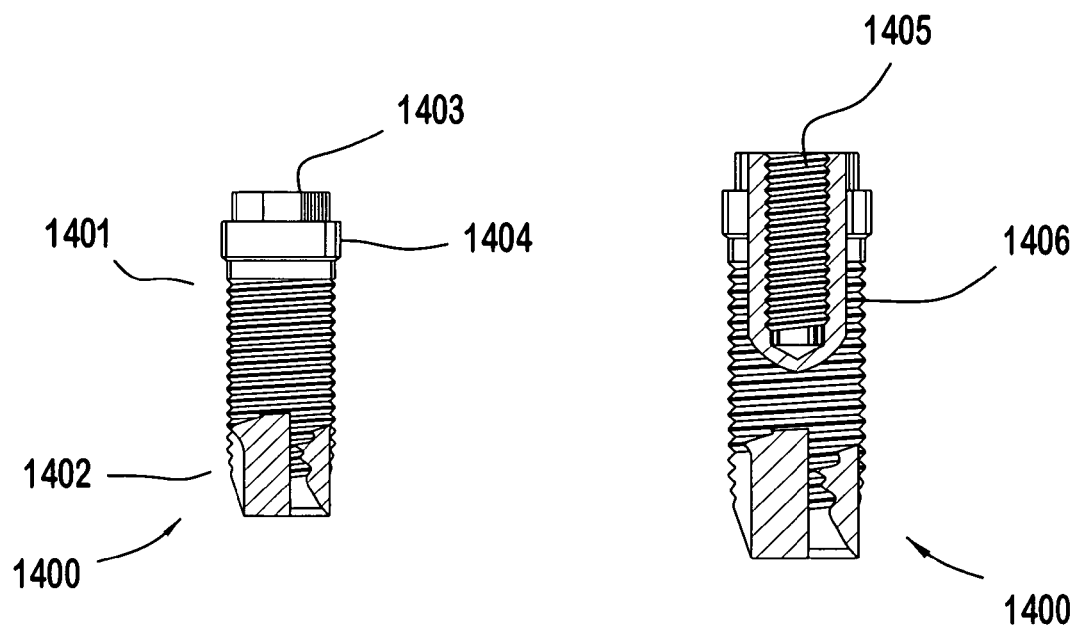
FIGS. 14A–C show one embodiment of a dental implant having a porous structure according to the present invention.
Figure 14C:
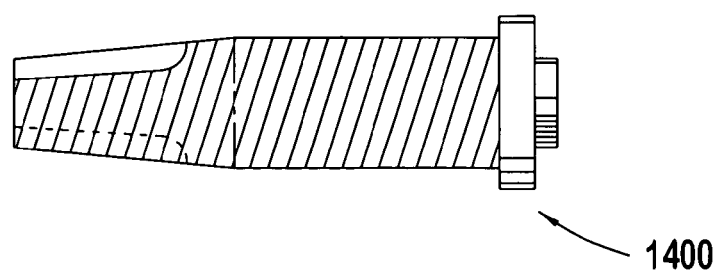

FIG. 14A illustrates a dental implant 1400 having a threaded region 1401 and a self-tapping region 1402. Dental implants are anchored into a bored hole of tissue in the jaw to permanently affix dental prosthetics. Dental implant 1400 also includes an attachment head 1403 for attaching a dental prosthesis and a collar 1404. In one embodiment, attachment head 1403 includes porous structure 110.

In one embodiment, shown in FIGS. 14A, B, C and E dental implant 1400 is constructed from stacked sheets to form a porous structure 110 as described herein. In one embodiment, the entire implant 1400 is constructed of porous structure. In one embodiment any portion or all of implant 1400 includes porous structure 110. Other embodiments are shown in FIG. 1F1 or 1F2, with or without threaded caps 191. In one embodiment, as shown in FIG. 14A, porous structure 110 is machined to incorporate a threaded region 1401 and a self tapping region 1402. In one embodiment, self tapping region 1402 includes traditional non-porous self-tapping threads. In one embodiment, self tapping region 1402 includes a porous structure with self-tapping threads. In another embodiment, self tapping region 1402 includes a self grafting porous structure 110 wherein porous structure 110 comprises sharp edges as described herein without traditional threads. In one embodiment, all or a portion of threaded region 1401 includes a porous structure of the present invention. Threaded region 1401 may have a threaded porous structure 110 or it may have a porous structure 110 of the present invention without threads. In one embodiment, during implantation, tissue is shaved by the self-tapping region 1402 by gently pushing device 1400 into its intended position, and or rotating device 1400. In this way, tissue is captured in the porous structure of implant 1400 thereby promoting the securement of the implant to the jaw.

FIG. 14B illustrates one embodiment of a dental implant 1400 with a bore 1405 which may be threaded to accept inserts. In this embodiment bore 1405 is formed from a solid core within implant 1400 and bore 1405 is surrounded by porous structure 1406 and formed as described herein.

Figure 14D:
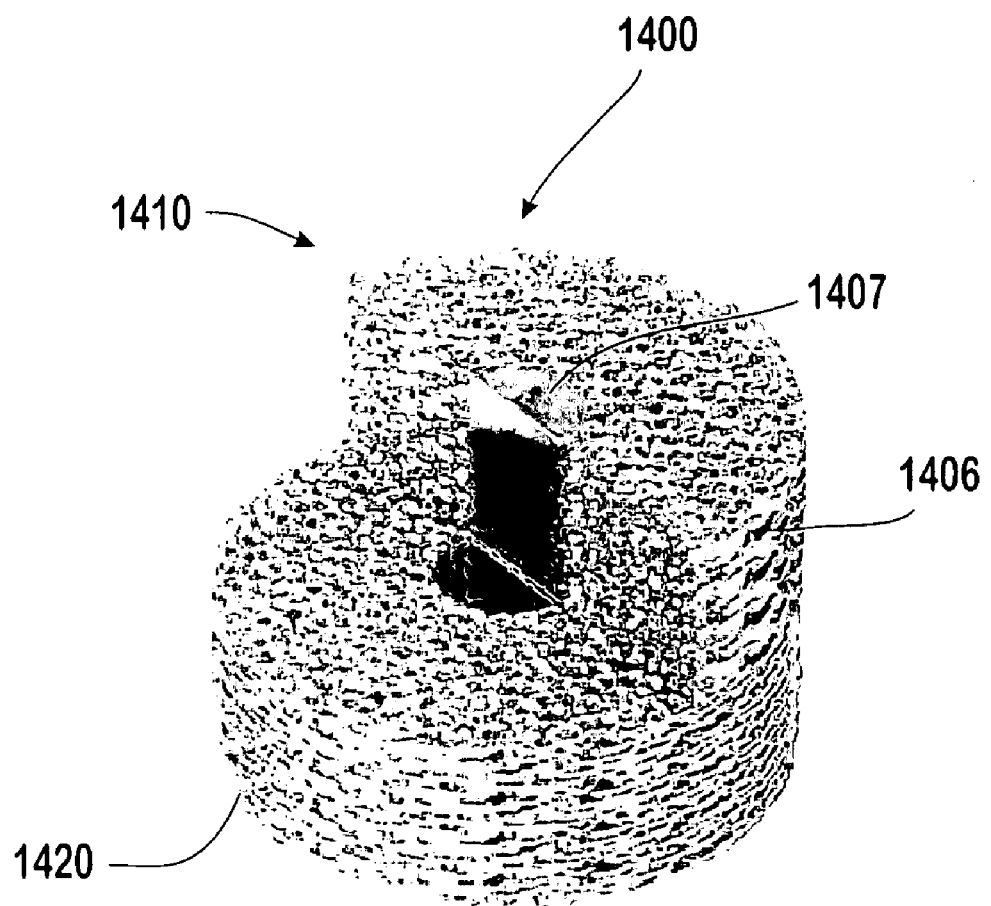
FIG. 14D shows one embodiment of a porous structure with a solid core portion according to the present invention.

FIG. 14D illustrates a porous structure 1410 having a solid core 1407 with a porous outer structure 1406 that is formed according to the present invention. In one embodiment, porous structure 1410 is formed by stacking individual sheets 200 having apertures 202 and an integral solid core 1407. Each sheet 200 is aligned such that a porous structure with a tortuous porosity is created about the circumference of a solid core 1407. Solid core 1407 may be bored as illustrated in FIG. 14B and preferably threaded to accept other appliances, for example as shown in FIG. 1F.

In one embodiment, core 1407 is a solid region that extends beyond open pore region 1420 so as to permit the attachment of an appliance (e.g., a crown, post, bridge) to core 1407. In one embodiment, core 1407 is then preferably machined to accommodate the hardware of the end use. For example, core 1407 may be threaded, grooved, and otherwise machined to accommodate an attachment device (e.g., a clip).

Figure 14E:
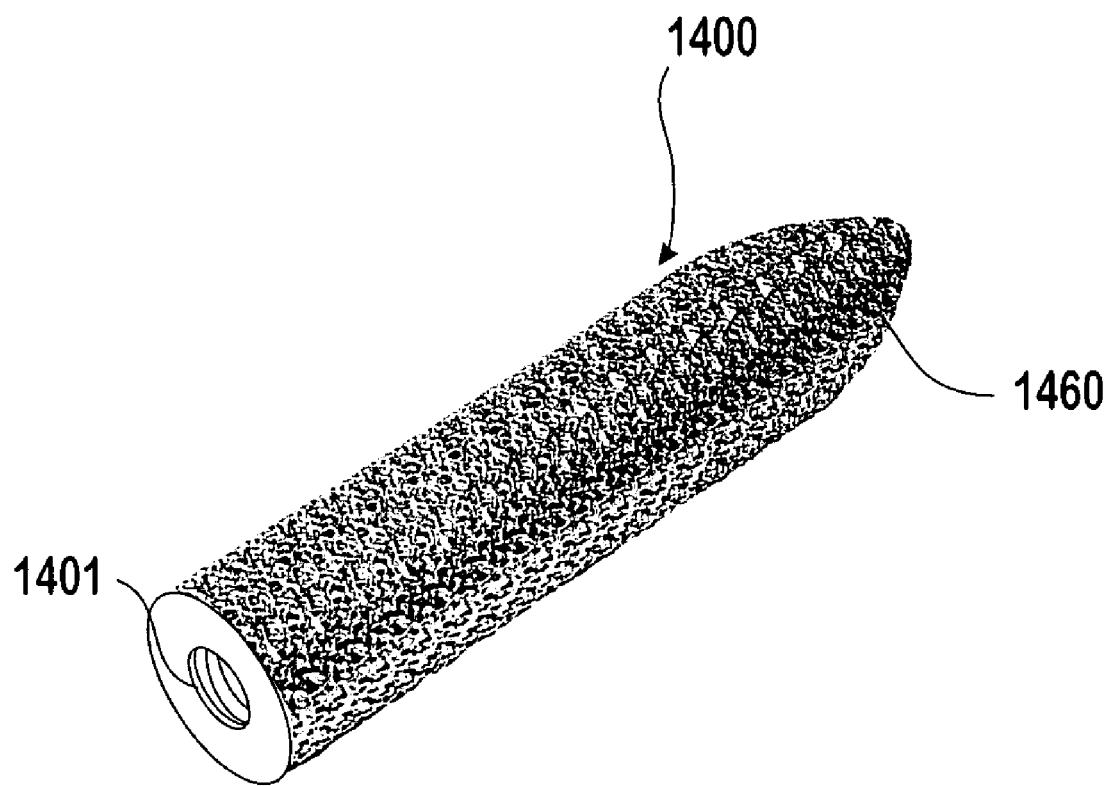
FIG. 14E shows one embodiment of a dental implant having a porous structure according to the present invention.

As shown in FIG. 14E, in one embodiment, dental implant 1400 is formed to include a tapered end 1460 and/or threaded region 1401. In one embodiment, the entire dental implant is tapered. In another embodiment, the open pore region is machined to achieve a conical configuration or any other desired configuration (e.g., threaded, tapered, slotted). In one embodiment, solid region 1407 transfers force to open pore region 1420 (e.g., to kinematically relate solid region 1407 to the open pore region 1420).

Figure 15:
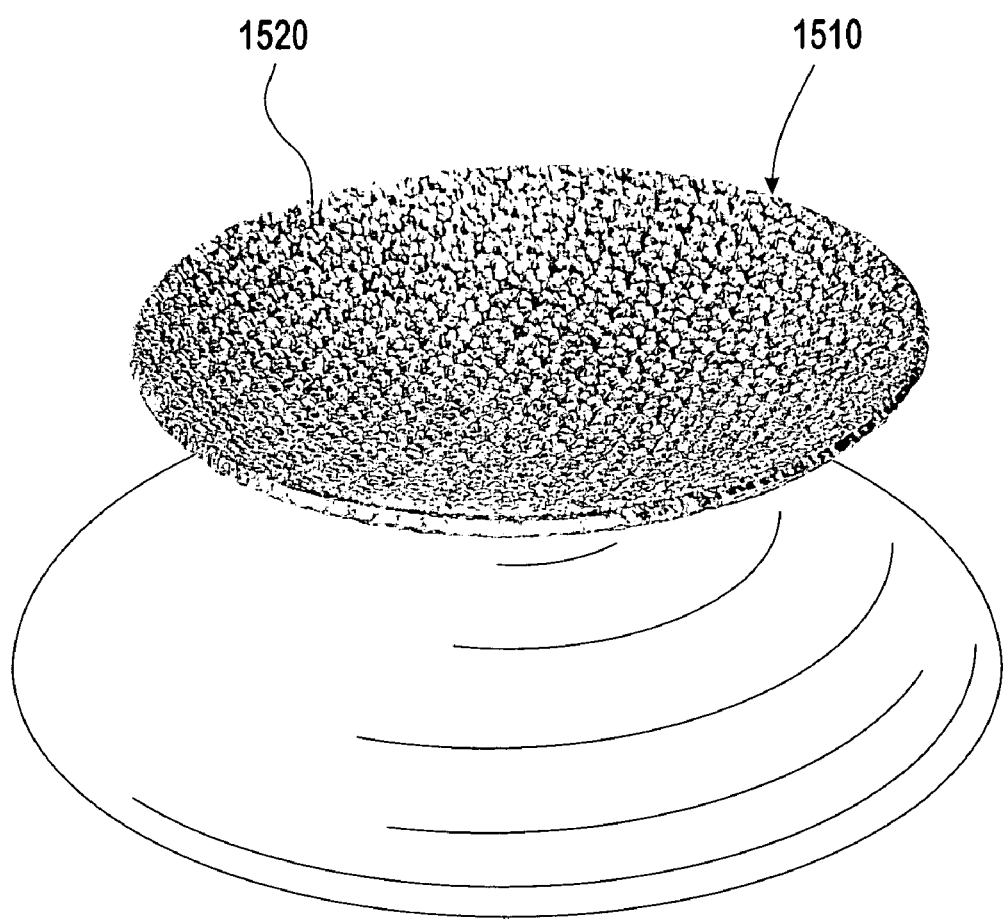
FIG. 15 shows one embodiment of a porous disc structure according to the present invention.

FIG. 15 illustrates a domed porous structure 1510. In one embodiment, the configuration of domed porous structure 1510 has been formed by cold working. For example, porous structure 1510 was created by placing a flat section of porous structure 110 into a hemispherical fixture (e.g., a steel or polymer die). By applying pressure to porous structure 1510, it was cold worked until porous structure 1510 had a concave face 1520. The porosity of porous structure 1510 is substantially the same as it had been prior to cold working. Porous structure 1510 is illustrated as attached to a polyurethane tool die. In one embodiment, heat is applied to porous structure 1510 during the forming process (e.g., to increase ductility). In determining the intensity of heat required to form porous structure 1510, those skilled in the art will consider, for example, the thickness and desired final shape of porous structure 1510.

Figure 16A:
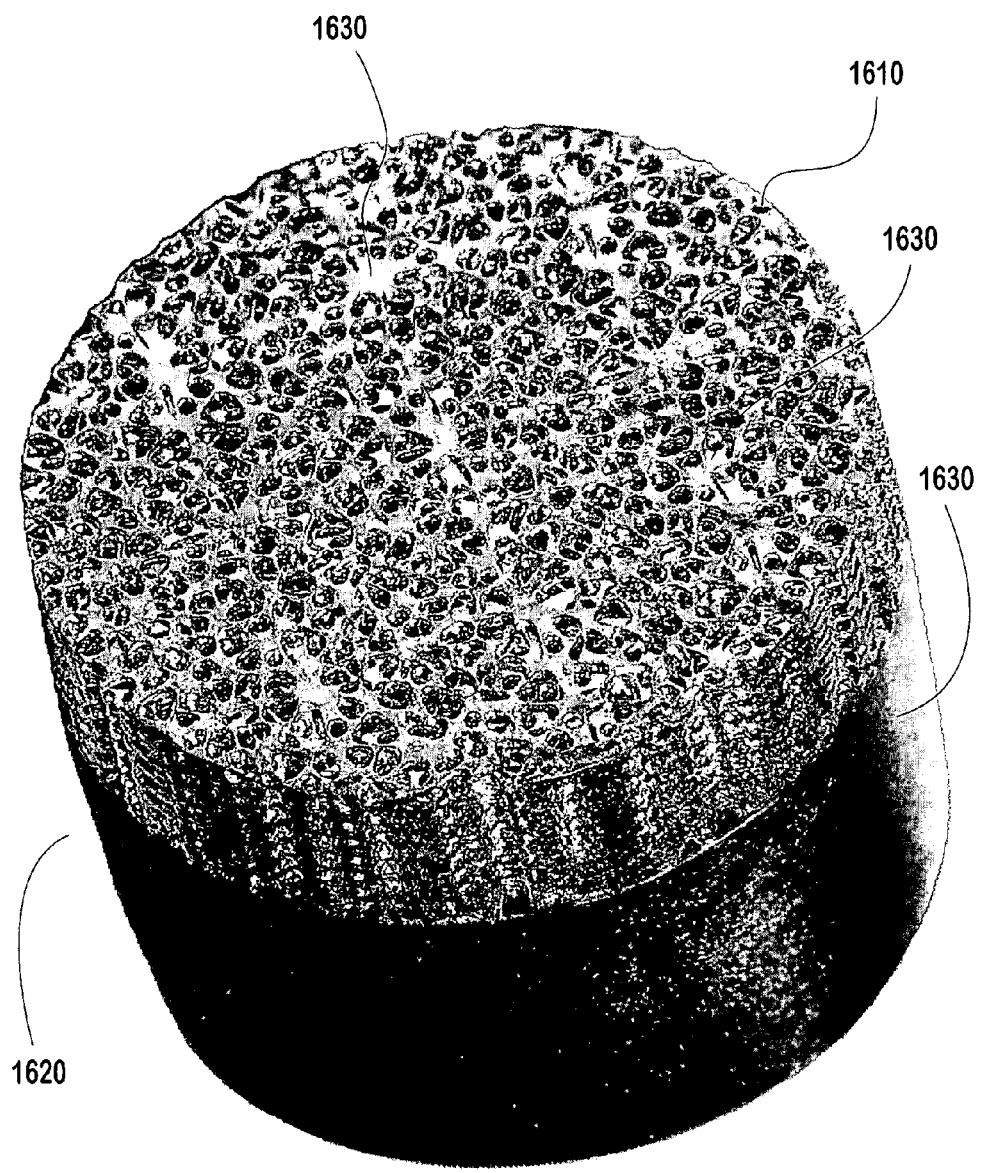
FIG. 16A shows one embodiment of a porous structure fused to a non-porous structure according to the present invention.

FIG. 16A illustrates the attachment of porous structure 1610 to a separately formed substrate such as work piece 1620. Porous structure 1610 may be formed from any of the materials and processes described herein. Work piece 1620 and porous structure 1610 may be of the same or different material. In one embodiment, work piece 1620 includes porous structure 1610. In one embodiment, work piece 1620 is connected (e.g., bonded) to porous structure 1610). In one embodiment, work piece 1620 is any refractory material or any material compatible with material of porous structure 1610. In another embodiment, work piece 1620 is constructed from polymer or ceramic. Work piece 1620 preferably is oxidized. In one embodiment, the work piece includes an oxidized surface (e.g., oxidized zirconium surface). In other embodiments, a cobalt-chrome work piece is combined with a porous structure 1610 of the same or different material. In other embodiments, a stainless steel work piece is combined with a porous structure 1610 of the same or different material. Work piece 1620 and porous structure 1610 may be bonded by any bonding method described herein including diffusion bonding during or after the formation of porous structure 1610 as described above.

Also illustrated in FIG. 16A are structural elements 1630 that form a grid pattern in porous structure 1610. Structural elements 1630 are formed as described herein and preferably provide additional lateral stability to porous structure 1610. In one embodiment, porous structure 1610 is configured to approximate at least one predetermined mechanical property (e.g., compressive strength, tensile strength, elongation strength, yield strength, ultimate yield strength, and elastic modulus). In one embodiment, structural elements 1630 provided stability to porous structure 1610 that prevents collapse of the network during diffusion bonding. Preferably, structural elements have a higher bond strength than the surrounding network and increase the overall strength of porous structure 1610. In preferred embodiment, the structural elements include posts, beams, and scaffolds.

Figure 16B:
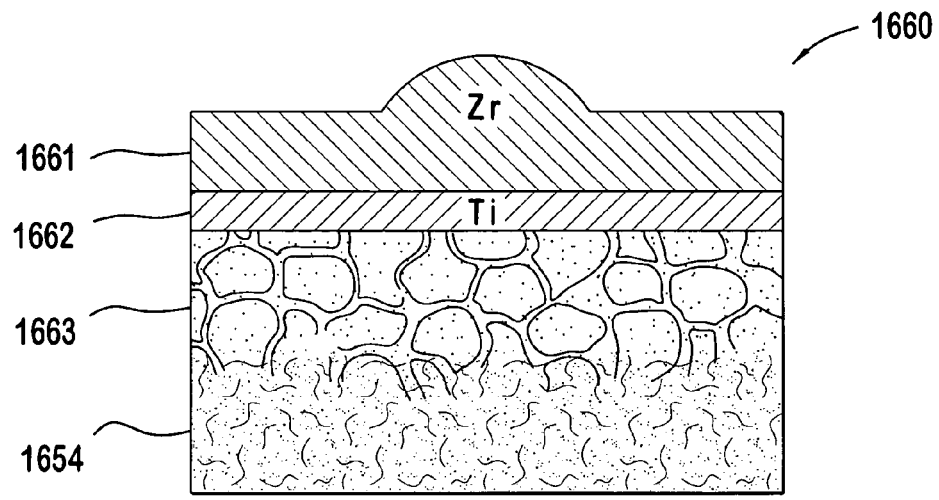
FIG. 16B–D show one embodiment of a multi-substrate composite according to the present invention.
Figure 16C:
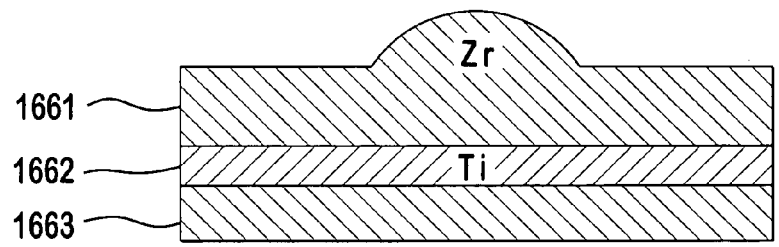
Figure 16D:
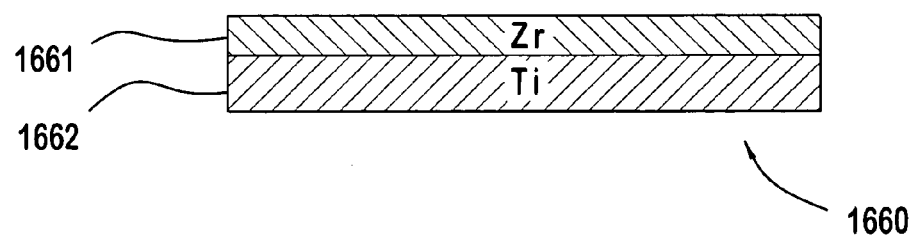

In one embodiment of the present invention, two or more different substrates (e.g., metals, polymer, fibers, porous substrates, textured substrates) may be bonded (e.g., by any of the bonded methods described herein) to form composites where the beneficial aspects of each material may be exploited. In one embodiment, one or more of the substrates includes porous material 1610. FIG. 16B–16D illustrate multi-composite substrate composites 1660. Multi-composite substrate 1660 includes any number of different, similar or identical materials. In one embodiment, multi composite substrate 1660 includes a first substrate 1662 including titanium diffusion bonded to a second substrate 1661 including zirconium. In one embodiment, a medical implant is formed from the diffusion bonded composite of a zirconium substrate and a titanium substrate.

In one embodiment, multi-substrate composite 1660 includes a first substrate 1661 (e.g., made of zirconium), a second substrate 1662 (e.g., made of titanium) and a complex layer substrate 1663 (FIG. 16B–16C). Complex layer substrate 1663 may be any material having a complex structure. Complex layer substrate 1663 preferably includes, porous structure 1610, or any substrate with a surface conducive to tissue (e.g., bone, ligament) in-growth including substrates having surfaces described in U.S. patent application Ser. No. 10/202,575; U.S. Pat. No. 5,258,098; U.S. Pat. No. 5,507,815; U.S. Pat. No. 5,922,029; and U.S. Pat. No. 6,193,762 all of which are hereby incorporated by reference. In one embodiment one or more of the layers 1661, 1662, 1663 has an oxidized surface preferably of oxidized zirconium.

FIG. 16B illustrates multi-substrate composite 1660 according to the present invention. In this embodiment, a first layer 1661 is made of zirconium, a second layer 1662 is made of titanium and a complex layer 1663 is made of porous structure 110 with the layers bonded together (e.g., by one or more of the bonding methods described herein). In one embodiment the layers 1661, 1662, 1663 are all metals. In one embodiment, complex layer 1663 is formed by porous beads, plasma spray, grit blasting and/or any other surface that is conducive to tissue ongrowth or ingrowth. In one embodiment, (FIG. 16B) bone ingrowth 1654 is promoted into complex layer 1663. In a preferred embodiment, a first layer of titanium porous structure is bonded to chromium-cobalt and then to a second layer of zirconium porous structure by, for example, diffusion bonding or explosive bonding. Diffusion bonding of different metals is preferably performed under care to select proper temperatures (e.g., approximately 850° C.) such that large brittle domains of intermetalic species are minimized. Cobalt/titanium has a eutectic region at 72 weight % titanium at 1025° C. Another eutectic for cobalt/titanium exists between 1050° C. and 1200° C. The combination of chromium and titanium is a solid solution melting around 1400° C. In one embodiment, (FIG. 16D) multi-composite substrate 1660 includes a zirconium substrate 1661 bonded to a titanium substrate 1662 using the bonding methods described herein.

Digital Implants

Figure 17:
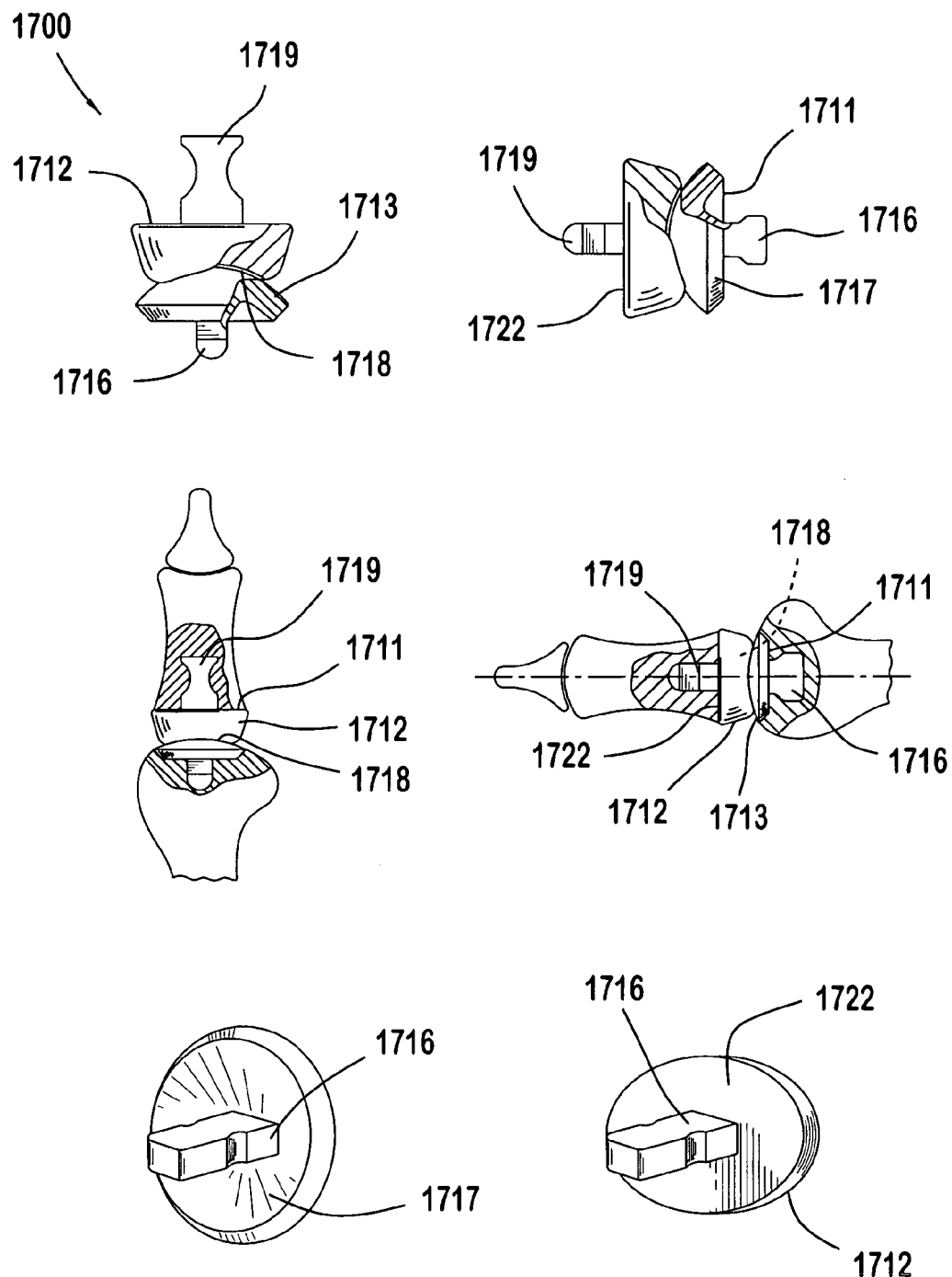
FIG. 17 show one embodiment of a digital implant including a porous structure according to the present invention.

The present invention has other applications for prosthetic joints such as those described in U.S. Pat. No. 4,156,296 and U.S. Pat. No. 5,984,971 which are hereby incorporated by references. FIG. 17 illustrates one such prosthetic joint, a toe 1700. Porous structure 110 may be incorporated into any portion or all components of endoprosthetic toe 1700. Among the features of an endoprosthetic toe 1700 that may be constructed from porous structure 110 are those portions which will contact tissue. Particular components include stems 1716, 1719 and surfaces 1717, 1722. For example, these components may be constructed separately and bonded to bearing surfaces 1713, 1718 to form phalanx component 1712 and metatarsal component 1711. Preferably, metatarsal component 1711 and phalanx component 1712 are formed as an integral piece as described above with porous structure 110 as an integral bonded component.

Figure 18:
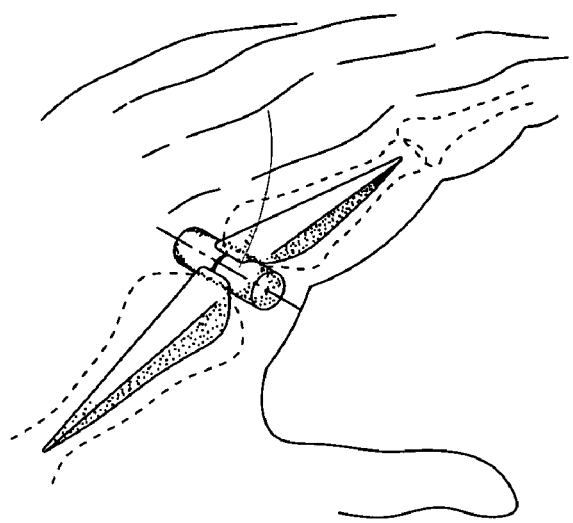
FIGS. 18A–C show one embodiment of a digital implant including a porous structure according to the present invention.
Figure 18:
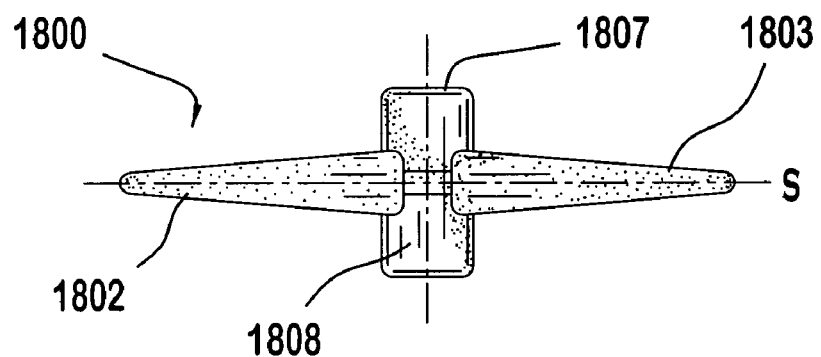
Figure 18:
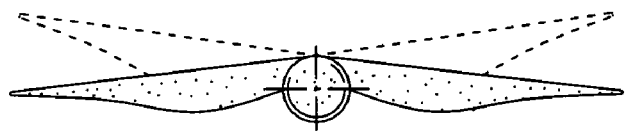

One embodiment of an endoprosthetic finger 1800 is illustrated in FIGS. 18A–18C. Among the features of endoprosthetic finger 1800 that preferably are constructed from porous structure 110 of the present invention are pins 1802, 1803 and walls 1807, 1808. All or a portion of finger 1800 may include porous structure 110.

Shoulder

Figure 19:
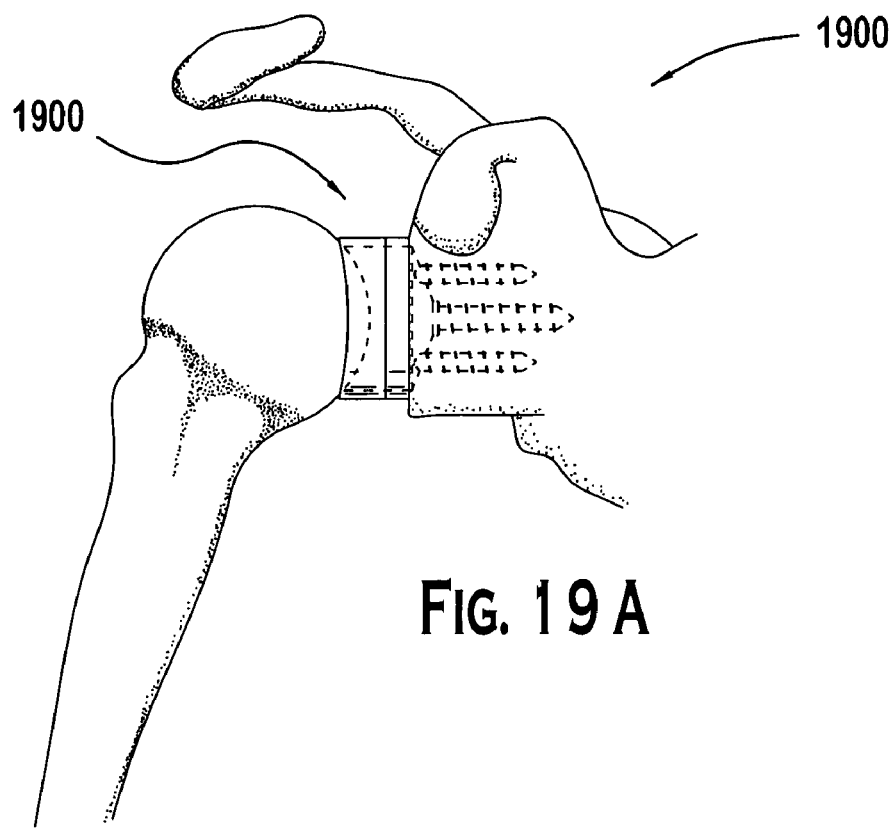
FIGS. 19A–B show one embodiment of a shoulder implant including a porous structure according to the present invention.
Figure 19:
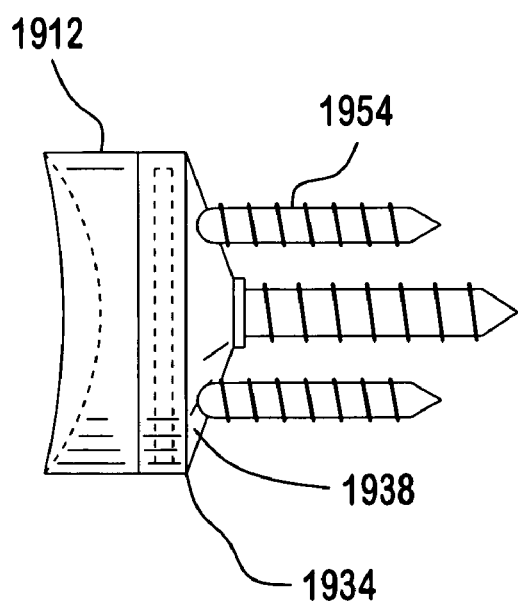

An example of a prosthetic shoulder 1900 (FIGS. 19A and 19B) that would be improved by the present invention is described in U.S. Pat. No. 6,679,916 which is hereby incorporated by reference. Among the features of shoulder 1900 that are preferably constructed from porous structure 110 are screws 1954, and backing plate 1934 including inner portion 1938. In one embodiment a polymer (e.g., UHMWPE) is infused into porous structure 110 for an integrated backing plate 1934 with a formed polymer (e.g., UHMWPE glenoid) socket 1912. All or any portion of shoulder 1900 may include porous structure 110.

Fastener Systems

Figure 20A:
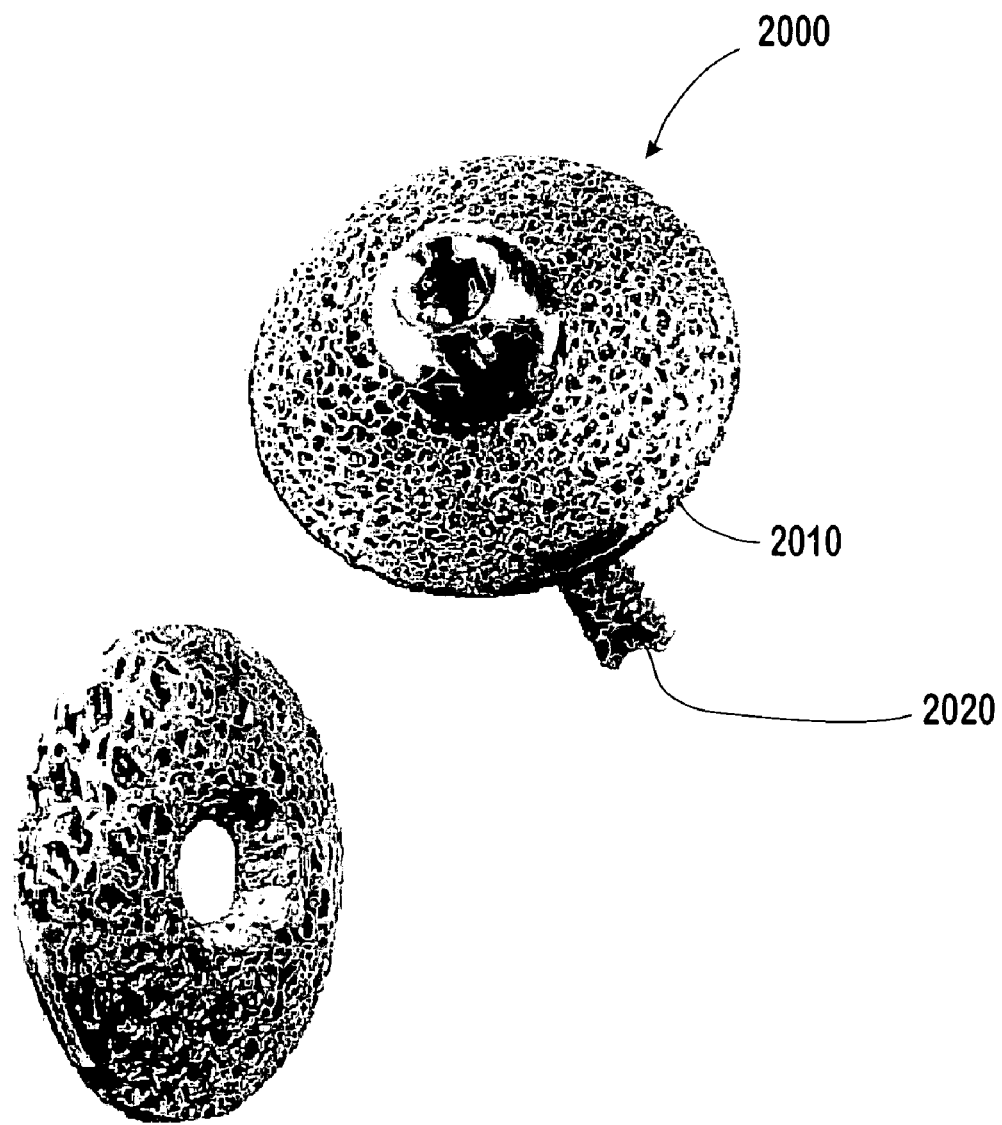
FIGS. 20A–D shows embodiments of a fasteners including a porous structure according to the present invention.
Figure 20B:
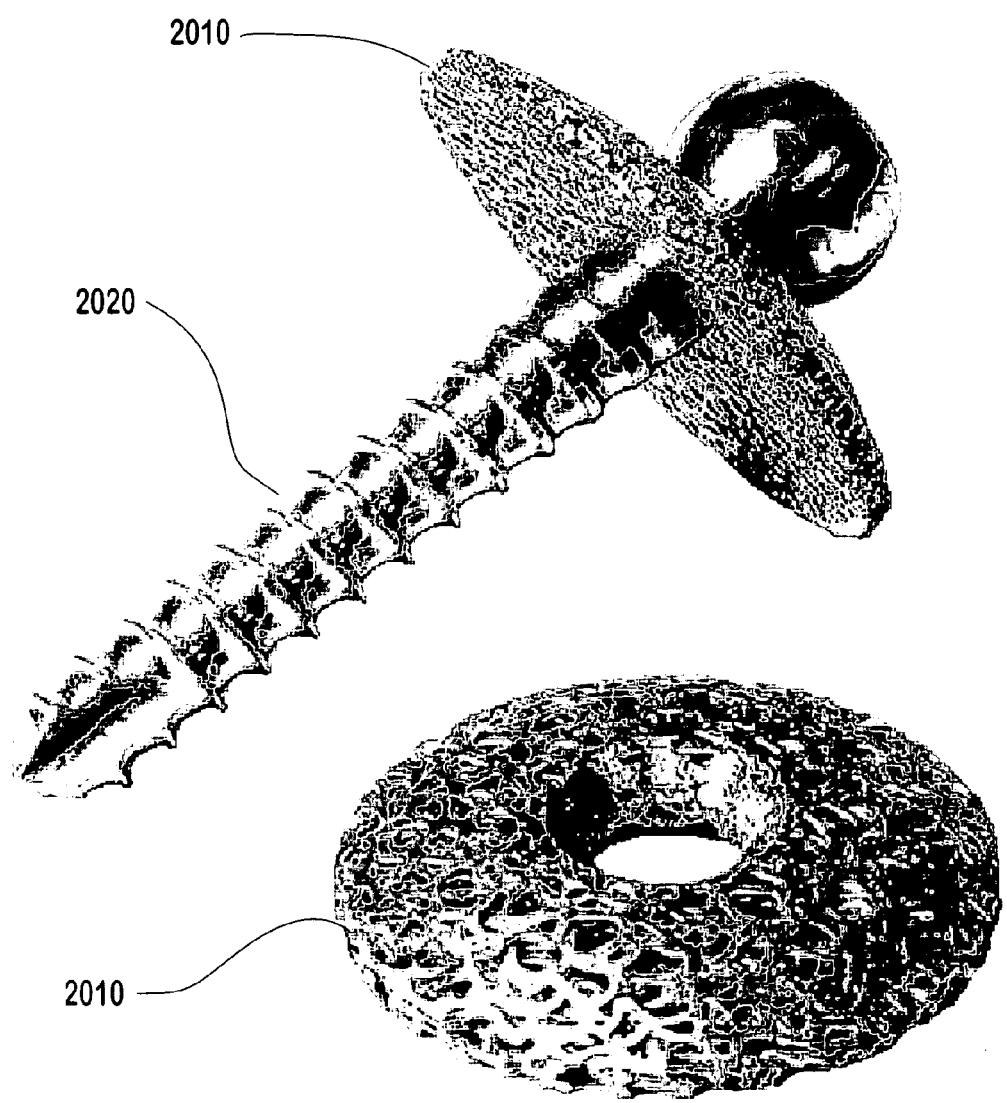
Figure 20:
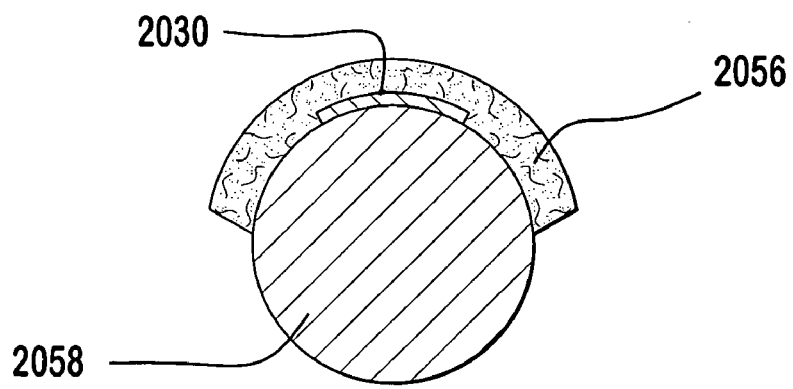
Figure 20:
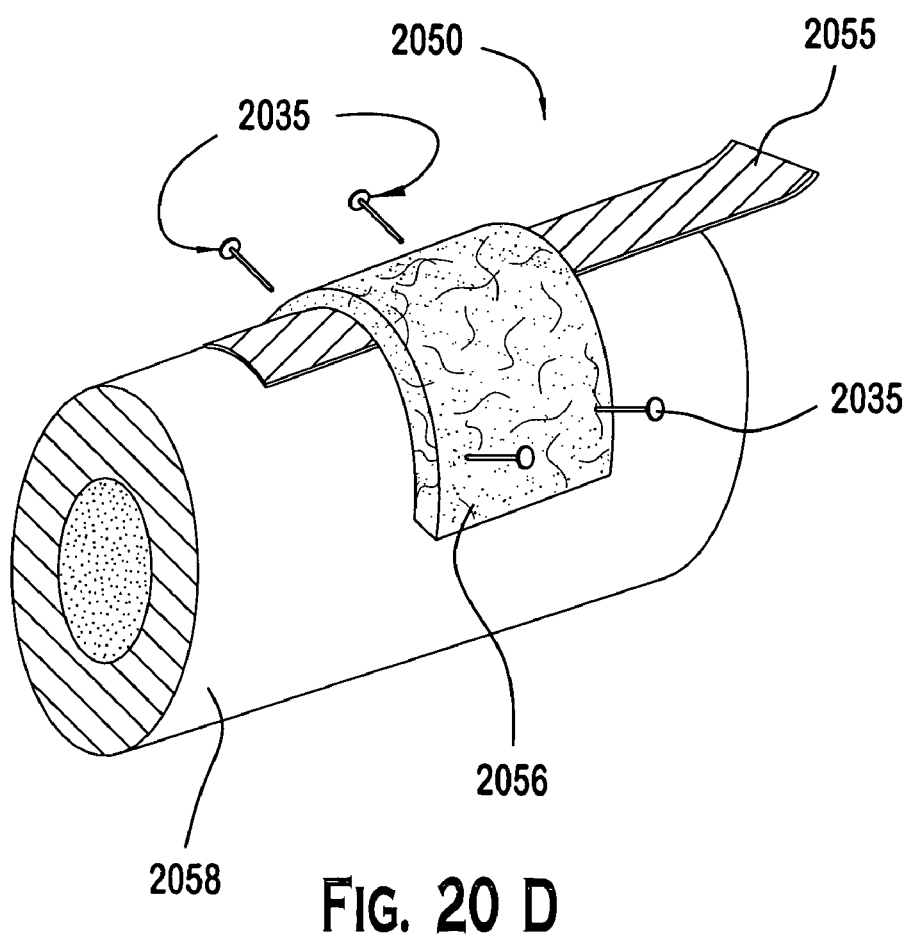

FIGS. 20A and 20B illustrates an embodiment of fastening system 2000. Porous structure 2010 has been post processed (e.g., machined, drilled) to a porous washer with a bearing surface. Post processing may include cold working porous structure 110 (e.g., washer 2010) with a hammer against a mold and/or hot formed to a specified shape. In one embodiment, bolt 2020 is also constructed from a porous structure of the present invention. In one embodiment, washer 2010 and bolt 2020 are formed as a single integral component. In one embodiment, bolt 2020 is formed from a solid core (see e.g., FIG. 14D or 1F1) surrounded by porous regions. The final integrated product may be post-processed for form a composite having solid and porous regions. In one embodiment, curved parts may be formed by modifying the bonding fixture to incorporate the desired curvatures. In one embodiment, this results in a fully-annealed and strain relieved part, made in a single operation.

Bone Ligament Attachment Appliance

In one embodiment, a medical implant designed to facilitate the joining of ligament to bone can be achieved in a single device having both an open pore reticulated structure with a porosity conducive to ligament growth and an open pore reticulated structure with a porosity conducive to bone growth as described herein.

There is shown in FIG. 20C another embodiment of a ligament attachment appliance 2050. In one embodiment, appliance 2050 includes porous structure 2056 and in some embodiments, fasteners 2035. In one embodiment, ligament 2055 is fixed to bone 2058 by clamping ligament 2055 between bone 2058 and porous structure 2056. Porous structure 2056 may be fixed to tissue 2058 (e.g., bone) by fasteners 2035, by applying an adhesive, or by any other means known to those skilled in the art. In one embodiment, fasteners 2035 are constructed at least in part by porous structure 110 (e.g., those described herein) or a textured structure. In one embodiment, fasteners 2035 are textured pins that are, for example, press fit into tissue to fasten porous structure 2056 to tissue 2058 (e.g., bone). In one embodiment, fasteners 2035 are threaded. In one embodiment, porous structure 2056 has an aperture 2030 (FIG. 25B) (e.g., slot) into which ligament 2056 is fit. Porous structure 2056 preferably provides a medium into which tissue will grow thereby facilitating the securement of, for example, ligament 2055 to bone 2058. In one embodiment, porous structure 2056 is treated to promote the growth of ligament 2055 and/or bone to facilitate the securement of ligament 2055 to bone 2058.

FIG. 1F1 illustrates a part 190 having a fastening system. Part 190 is conventionally machined from a block of porous structure 110 having a solid border region 191. The solid border region 191 is conventionally tapped to form a 10-32 thread. This type of securement may be useful in several classes of devices including joint implants and dental post implants.

FIG. 1F2 describes a partial spherical implant 195 suitable for providing stability to bone fractures. Implant 195 is preferably screwed into place or held securely with wire, clamps or any other mechanical retention means.

Other Bearing Elements

In one embodiment, complex textures may be generated into bearing elements such as anti-friction pads, bushings for thrust loads or radial loads, or rolling bearing assemblies. Metal lattice networks may also be employed as a transitional bonding system for such applications. Wear plates or other bearings may be bonded, molded into, formed, or otherwise attached to a variety of dissimilar materials by causing the host material (e.g., polymer) to interpenetrate the network of a three dimensionally textured surface or a bonded sponge-like lattice (e.g., porous structure 110). In one embodiment, a bushing is securely assembled to a thermoplastic part in a single operation by inserting the properly textured part into an injection mold prior to the injection cycle.

A ceramic sphere may be used in a ball joint application by diamond or laser machining a series of grooves in one side of the sphere. In one embodiment, a diffusion-bonded porous structure is properly designed and consolidated around the sphere to securely attach the two components. Alumina, zirconia, yttria, and similar ceramics withstand diffusion bonding temperatures used in preparing porous structure 110. Upon slow cooling, a strainless composite preferably results. This application is especially useful in ball joints that are primarily used in compressive loading applications.

Figure 21:
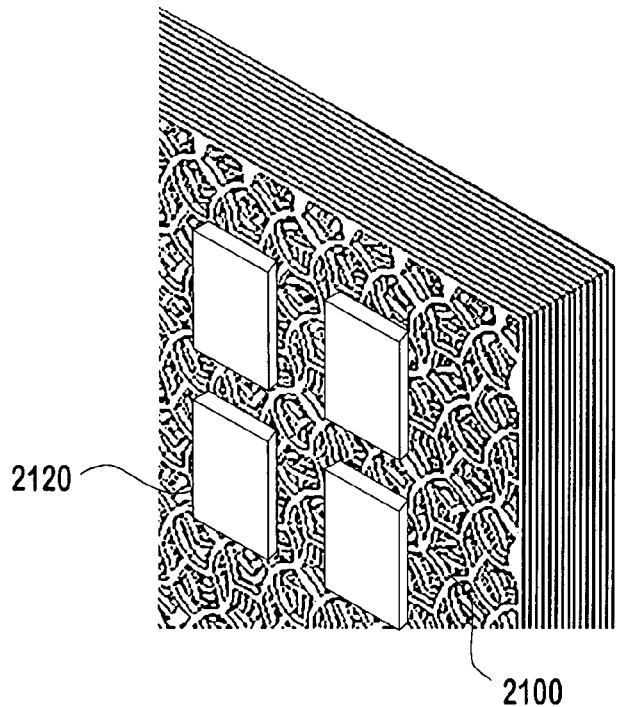
FIG. 21 shows one embodiment of a porous structure according to the present invention including bearing elements.

FIG. 21 illustrates a porous structure 2100 having wear-resistant elements 2120. Wear-resistant elements 2120 are preferably diffusion bonded to porous structure 2100 though they may be bonded by any means known including brazing or any other means known in the metal working art. Wear resistant elements 2120 preferably are held in place by mechanical means (e.g., grooves, slots, holes and/or keyways). It is preferable that bonding take place during the forming of porous structure 2100 as described above, though wear-resistant elements may be bonded at any time. Wear resistant elements 2120 are preferably constructed from zirconium, oxidized zirconium, hafnium, platinum, niobium or alloys thereof. In other embodiments, wear resistant elements are constructed from cobalt-chrome or chrome-cobalt-molybdenum alloys or any other material that is known to resist wear. In one embodiment, wear resistant elements 2120 are coated with an oxidized layer (e.g., oxidized zirconium) or are chemically modified so as to produce a wear resistant surface (e.g., conversion of titanium to calcium titanate). Wear resistant elements 2120 may be or may not be of the same material that forms porous structure 2100. For example, in one embodiment, porous structure 2100 is titanium and wear-resistant elements 2120 are a zirconium alloy. In another embodiment wear-resistant elements 2120 are a chromium-cobalt alloy.

Consumable Metal Foam

Figure 22:
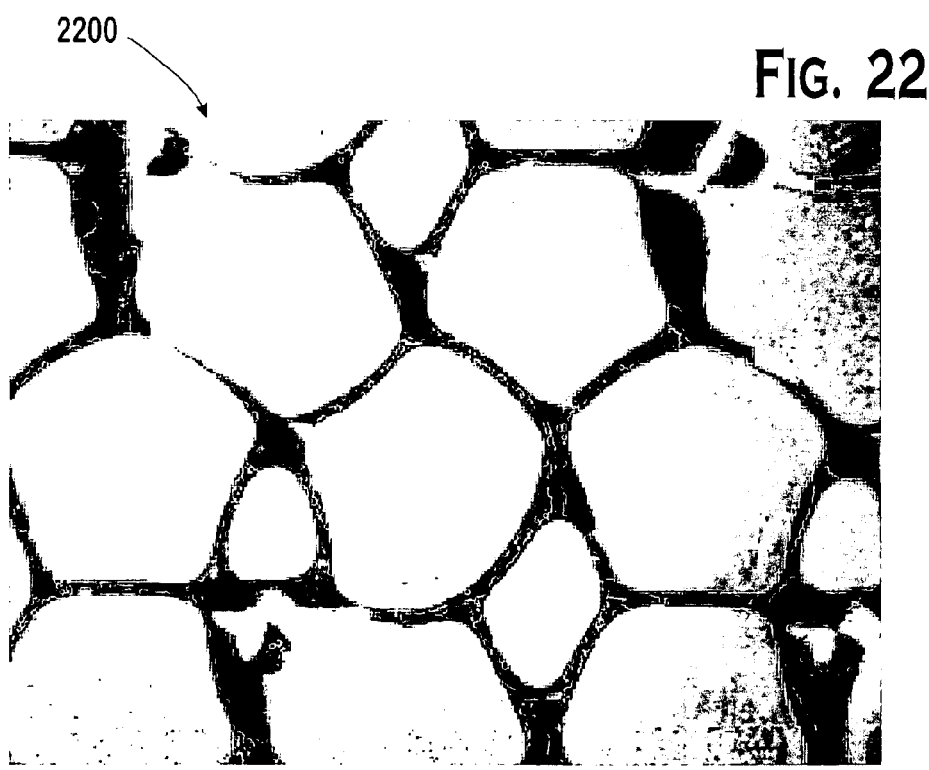
FIG. 22 shows one embodiment of a negative sponge structure according to the present invention.

FIG. 22 illustrates negative sponge structure 2200. Negative sponge structure 2200 is preferably assembled by forming a porous structure (e.g., as described above) from a readily-consumable host metal (e.g., aluminum, magnesium, iron). A polymer (e.g., UHMWPE, PTFE, HDPE, hydroxyapetite, PEEK, polyglycolic acid, polylactic acid, polyoxyethylenes and similar materials and co-polymers thereof) is preferably infused (e.g., compression molded) throughout at least a portion and preferably the entirety of the porous structure. The porous structure is then consumed (e.g., dissolved by an appropriate acid, base, or salt solution) leaving behind negative sponge structure 2200.

Compliant Assemblies for Shock Absorption

Figure 23A:
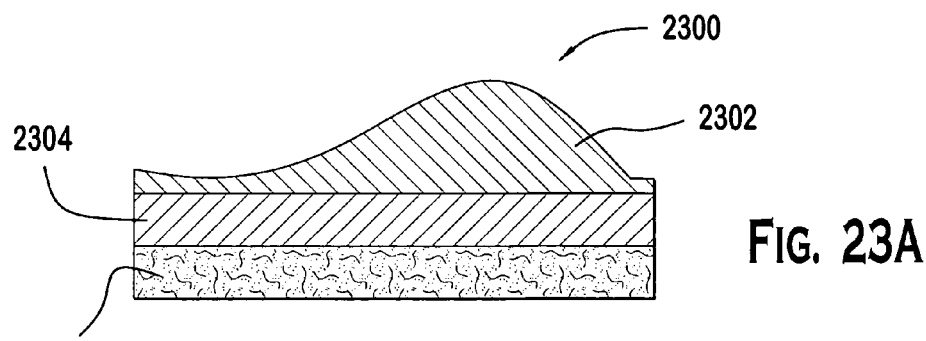
FIGS. 23A–23E shows one embodiment of a composite structure according to the present invention.
Figure 23B:
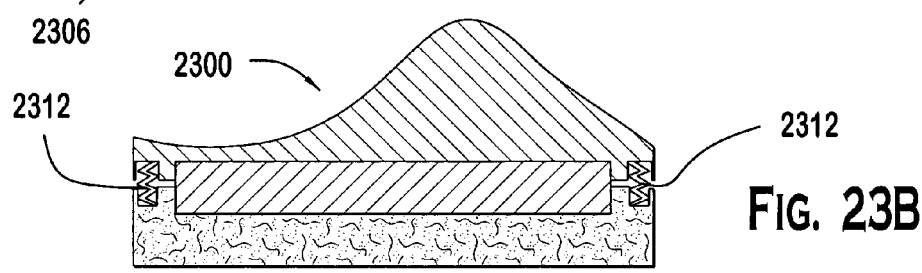
Figure 23C:
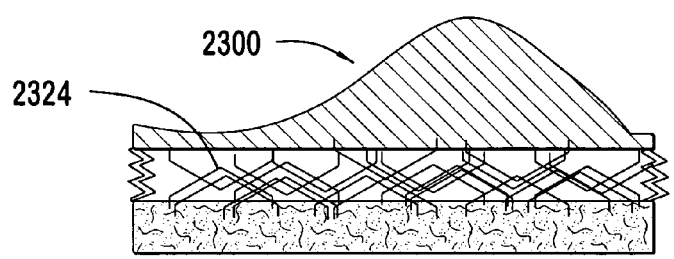

FIG. 23A illustrates composite 2300 having bearing surface 2302, resilient material 2304 and porous structure 2306. In one embodiment, porous structure 110 includes a compliant surface engaging region. The compliant surface can be a silicone or urethane elastomer that is engaged by the texture or porosity of the metal part. In one embodiment, bearing surface 2302 is a refractory metal (e.g., titanium, tantalum, zirconium, hafnium, platinum, rhodium, niobium and alloys thereof) gold, cobalt-chrome alloys, chrome-cobalt-molybdenum alloys, aluminum, stainless steel, any alloys thereof. In one embodiment bearing surface 2302 is oxidized zirconium. Resilient material 2304 is any elastic material preferably polymer.

In one embodiment, seal 2312 is inserted in composite 2300 to protect resilient material 2304 from degradation. In one embodiment, 2312 is bonded to the perimeter of composite 2300 to prevent exposure of resilient material 2304 to incompatible materials. In one embodiment, seal 2312 is a bellows seal. In one embodiment, seal 2312 has a diaphragm arrangement or any other seal configuration known in the art.

Figure 23D:
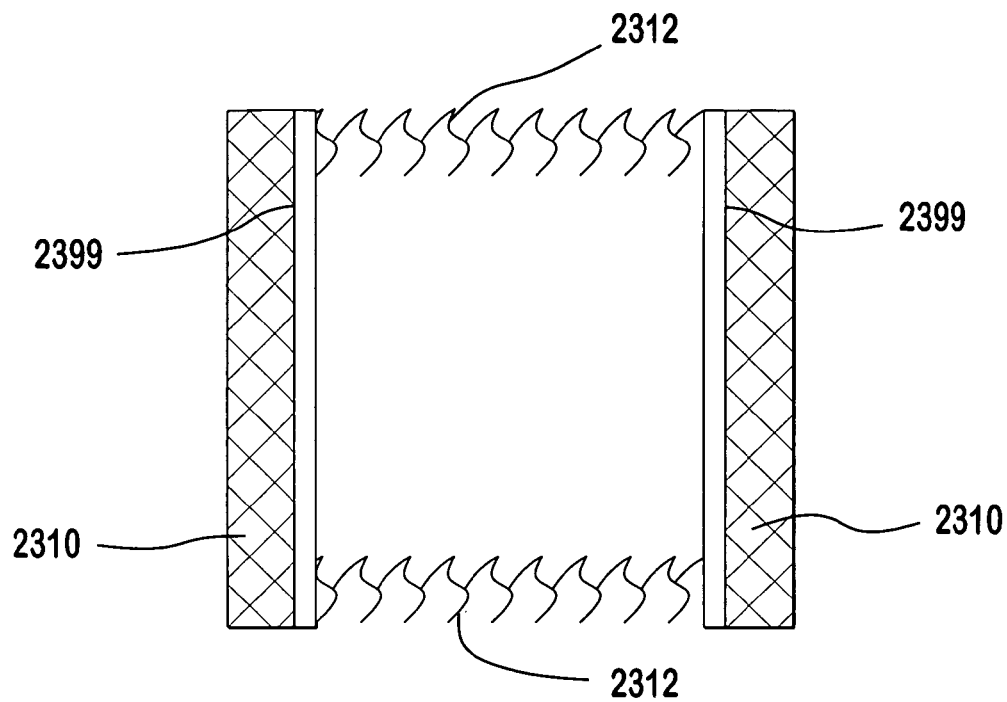
Figure 23E:
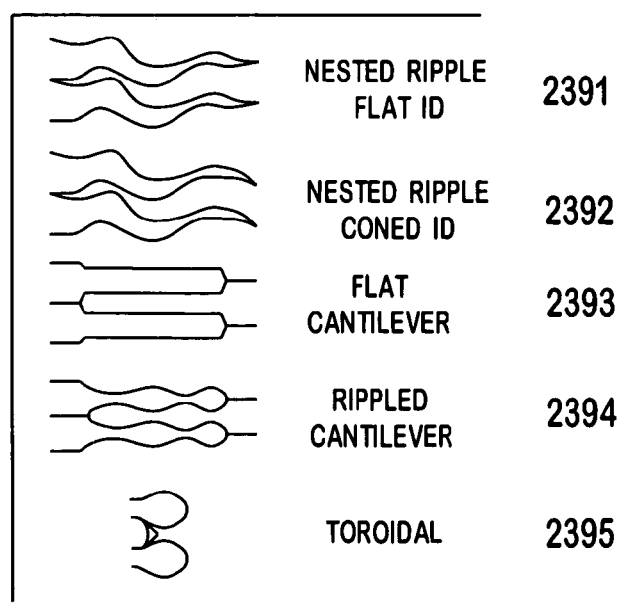

In one embodiment, illustrate in FIG. 23D, a seal 2312 is inserted between two porous structures 2310. Geometric configurations of seal 2312 may be any of those known in the art. Seal 2312 preferably includes those illustrated in FIG. 23E (e.g., nested ripple flat ID 2391, nested ripple coned ID 2392, flat cantilever 2393, rippled cantilever 2394, and toroidal 2395). In one embodiment, seal 2312 provides containment for resilient material between porous structures 2310 (e.g., where in porous structure 2310 includes a barrier layers 2399). In one embodiment resilient materials include fluids (e.g., gels, semi-solids, liquids and gasses). In one embodiment, porous structure 2310 is suitable for fusion to vertebrae and seal 2312 contains resilient materials to provide shock damping qualities to a fused spine.

In one embodiment, resilient material 2304 is replaced with spring 2324. Spring 2324 may be a leaf-spring, or any other resilient or elastic mechanism known in the art.

Other Composites

Figure 24:
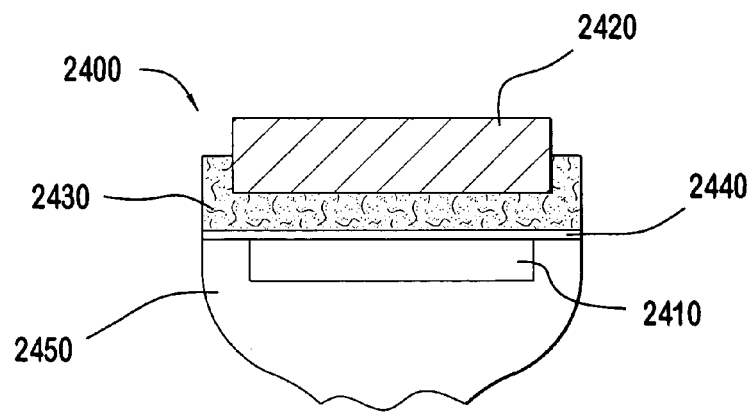
FIG. 24 shows one embodiment of a composite structure according to the present invention.

FIG. 24 illustrates compliance chamber composite 2400. In one embodiment, compliance chamber composite 2400 has a gas filled compliance chamber 2410, bearing surface 2420, porous structure 2430, and diaphragm 2440. In one embodiment, chamber 2410 is filled with air or inert gas (e.g., argon). In one embodiment, bearing surface 2420 is any suitable bearing surface as disclosed herein. In one embodiment bearing surface 2420 is UHMWPE. In one embodiment diaphragm 2440 is integral with porous structure 2430. In another embodiment, diaphragm 2440 is formed separately from porous structure 2430 and bonded to porous structure 2430. Diaphragm 2440 is preferably titanium but may be of any suitable material. In one embodiment, diaphragm 2440 is bonded or electron beam welded to lower mounting body 2450. Lower mounting body 2450 may be solid material, porous structure 110 any material suitable for attachment to tissue (e.g., bone, ligament).

In one embodiment, there is a class of devices that are intended to be used in applications where a shock-absorbing component is desirable. In one embodiment, compliance chamber composite 2400 is used as a shock-absorbing device. In one embodiment, for example, shock-absorbing component 2400 is used in spinal implant applications (e.g., where walking or jumping shock could be absorbed by a resilient material, such as an elastomer like silicone rubber, fluorosilicone rubber, or a urethane.) In one embodiment, a compliant metal diaphragm 2440 or other type of seal is used to isolate the shock absorbing media from a degrading environment (e.g., isolating urethanes from enzymes present in the body that cleave polyether linkages and isolating silicones that absorb lipids that degrade their mechanical properties.) In one embodiment, the use of metal seals (e.g., bellows or diaphragms) allows the use of an inert gas (e.g., argon) to be sealed in the metal bladder to serve as a shock absorbing medium.

Ceramic Applications

In one embodiment of the present invention, ceramic bodies are embedded in porous structure 110. In one embodiment ceramic bodies are embedded prior to bonding (e.g., diffusion bonding of sheets 200). In one embodiment, ceramic bodies are embedded at specific locations (e.g., near the surface porous structure 110). After bonding, post-processing is preferably performed to expose a portion of the ceramic bodies. In one embodiment, post processing includes etching away a portion of the porous structure 10 and grinding, lapping, and/or polishing the ceramic body to a smooth low friction surface.

Although the foregoing description is directed to the preferred embodiments of the invention, it is noted that other, variations and modifications in the details, materials, steps and arrangement of parts, which have been herein described and illustrated in order to explain the nature of the preferred embodiment of the invention, will be apparent to those skilled in the art, and may be made without departing from the spirit or scope of the invention.

REFERENCES

All patents, patent applications, papers and publications referenced herein are hereby incorporated by reference as if recited in their entirety herein.

What is claimed is:

1. A medically implantable porous structure comprising:
a plurality of stacked bonded sheets, each sheet having
   a network of webs that define a multiplicity of apertures; and
   at least one solid region integral with and surrounded by the network of webs;
wherein at least one solid region of at least one of the stacked bonded sheets is aligned with at least one of the solid regions of at least one adjacent sheet to form at least one integral structural element; and
wherein the solid regions are configured to form a transition from a foam-like structure to a stiffening member.

2. The medically implantable porous structure of claim 1 wherein the transition is taken from the group consisting of abrupt and gradual.

3. A medically implantable porous structure comprising:
a plurality of stacked bonded sheets, each sheet having
   a network of webs that define a multiplicity of apertures; and
   at least one solid region integral with and surrounded by the network of webs;
wherein at least one solid region of at least one of the stacked bonded sheets is aligned with at least one of the solid regions of at least one adjacent sheet to form at least one integral structural element; and
wherein the solid regions are configured to form at least one solid pillar.

4. A medically implantable porous structure comprising:
a plurality of stacked bonded sheets, each sheet having
   a network of webs that define a multiplicity of apertures; and
   at least one solid region integral with and surrounded by the network of webs;
wherein at least one solid region of at least one of the stacked bonded sheets is aligned with at least one of the solid regions of at least one adjacent sheet to form at least one integral structural element; and
wherein the integral structure element is configured to form solid pillars that extend throughout the medically implantable porous structure.

5. The medically implantable porous structure of claim 4 wherein the solid pillars protrude through the medically implantable porous structure.

6. A medically implantable porous structure comprising:
a plurality of stacked bonded sheets, each sheet having
   a network of webs that define a multiplicity of apertures; and
   at least one solid region integral with and surrounded by the network of webs;
wherein at least one solid region of at least one of the stacked bonded sheets is aligned with at least one of the solid regions of at least one adjacent sheet to form at least one integral structural element; and
wherein the apertures comprise:
a plurality of first apertures with a full penetration depth and
a plurality of second apertures with a partial penetration depth.

7. A medically implantable porous structure comprising:
a plurality of stacked bonded sheets, each sheet having
   a network of webs that define a multiplicity of apertures; and
   at least one solid region integral with and surrounded by the network of webs;
wherein at least one solid region of at least one of the stacked bonded sheets is aligned with at least one of the solid regions of at least one adjacent sheet to form at least one integral structural element; and
wherein the apertures have a dimension in the plane of the sheet of between 10 microns and 5000 microns.

8. A medically implantable porous structure comprising:
a plurality of stacked bonded sheets, each sheet having
   a network of webs that define a multiplicity of apertures; and
   at least one solid region integral with and surrounded by the network of webs;
wherein at least one solid region of at least one of the stacked bonded sheets is aligned with at least one of the solid regions of at least one adjacent sheet to form at least one integral structural element: and the medically implantable porous structure has a porosity of between 5 percent and 90 percent by volume.

9. A medically implantable porous structure comprising:
a plurality of stacked bonded sheets, each sheet having:
   a plurality of first apertures with a full penetration depth and
   a plurality of second apertures with a partial penetration depth
   the first apertures and second apertures having a diameter between 10 microns and 5000 microns.
wherein at least one of the first apertures in each of at least two adjacent sheets are aligned to form a tortuous pore.

* * * * *

UNITED STATES PATENT AND TRADEMARK OFFICE
CERTIFICATE OF CORRECTION

PATENT NO.        : 7,208,222 B2
APPLICATION NO.   : 10/898659
DATED             : April 24, 2007
INVENTOR(S)       : Jonathan L. Rolfe et al.

It is certified that error appears in the above-identified patent and that said Letters Patent is hereby corrected as shown below:

Title Page; should read;
Item (56), References Cited – Other Publications
Please insert --BRINK, J.H.K., et al., Micro Imaging for the Determination of Bone Structure, OGO MDP; 2002-2003--.

Signed and Sealed this

Twenty-fourth Day of July, 2007

JON W. DUDAS
*Director of the United States Patent and Trademark Office*